US007960562B2

(12) United States Patent
Hirano et al.

(10) Patent No.: US 7,960,562 B2
(45) Date of Patent: Jun. 14, 2011

(54) PROPANE-1,3-DIONE DERIVATIVE OR SALT THEREOF

(75) Inventors: Masaaki Hirano, Tokyo (JP); Isao Kinoyama, Tokyo (JP); Shunichiro Matsumoto, Tokyo (JP); Eiji Kawaminami, Tokyo (JP); Kei Ohnuki, Tokyo (JP); Hirofumi Yamamoto, Tokyo (JP); Kazuhiko Osoda, Tokyo (JP); Tatsuhisa Takahashi, Tokyo (JP); Takashi Shin, Tokyo (JP); Takanori Koike, Tokyo (JP); Itsuro Shimada, Tokyo (JP); Hiroyuki Hisamichi, Tokyo (JP); Toshiyuki Kusayama, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 527 days.

(21) Appl. No.: 11/887,384

(22) PCT Filed: Mar. 30, 2006

(86) PCT No.: PCT/JP2006/306641

§ 371 (c)(1),
(2), (4) Date: Sep. 28, 2007

(87) PCT Pub. No.: WO2006/106812

PCT Pub. Date: Oct. 12, 2006

(65) Prior Publication Data

US 2009/0181964 A1 Jul. 16, 2009

(30) Foreign Application Priority Data

Mar. 31, 2005 (JP) ............................ P. 2005-101437
Dec. 7, 2005 (JP) ............................ P. 2005-353577

(51) Int. Cl.
*A61K 31/4184* (2006.01)
*C07D 235/12* (2006.01)

(52) U.S. Cl. .................................... 548/310.1; 514/394

(58) Field of Classification Search ................ 548/310.1
See application file for complete search history.

(56) References Cited

U.S. PATENT DOCUMENTS

| | | | |
|---|---|---|---|
| 4,062,686 | A | 12/1977 | Van Allan et al. |
| 4,119,466 | A | 10/1978 | Van Allan et al. |
| 4,263,393 | A | 4/1981 | Chen |
| 4,636,509 | A | 1/1987 | Phillipps et al. |
| 4,946,960 | A | 8/1990 | Wade et al. |
| 4,950,640 | A | 8/1990 | Evans et al. |
| 4,966,828 | A | 10/1990 | Doenges et al. |
| 5,055,579 | A | 10/1991 | Pawlowski et al. |
| 5,064,747 | A | 11/1991 | Imai et al. |
| 5,104,783 | A | 4/1992 | Shimada et al. |
| 5,112,743 | A | 5/1992 | Kamiya et al. |
| 5,141,841 | A | 8/1992 | Wade |
| 5,202,221 | A | 4/1993 | Imai et al. |
| 5,385,807 | A | 1/1995 | Okamoto et al. |
| 5,445,930 | A | 8/1995 | Harada et al. |
| 5,519,136 | A | 5/1996 | Wade |
| 5,593,818 | A | 1/1997 | Kawamoto |
| 5,616,537 | A | 4/1997 | Yokota et al. |
| 5,738,982 | A | 4/1998 | Harada et al. |
| 5,747,235 | A | 5/1998 | Farid et al. |
| 5,747,236 | A | 5/1998 | Farid et al. |
| 5,770,544 | A | 6/1998 | Yokota et al. |
| 5,817,819 | A | 10/1998 | Furuya et al. |
| 5,994,051 | A | 11/1999 | Gould et al. |
| 6,051,359 | A | 4/2000 | Ohkawa et al. |
| 6,087,503 | A | 7/2000 | Furuya et al. |
| 6,140,384 | A | 10/2000 | Sorori et al. |
| 6,153,371 | A | 11/2000 | Farid et al. |
| 6,162,813 | A | 12/2000 | Goulet et al. |
| 6,346,534 | B1 | 2/2002 | Zhu et al. |
| 6,395,733 | B1 | 5/2002 | Arnold et al. |
| 6,413,503 | B1 | 7/2002 | Habeck et al. |
| 6,468,711 | B1 | 10/2002 | Sorori et al. |
| 6,960,591 | B2 | 11/2005 | Hirano et al. |
| 7,569,688 | B2 | 8/2009 | Hirano et al. |
| 2002/0177556 | A1 | 11/2002 | Engel et al. |
| 2003/0191164 | A1 | 10/2003 | Hirano et al. |
| 2004/0029040 | A1 | 2/2004 | Watanabe et al. |
| 2005/0267110 | A1 | 12/2005 | Hirano |

FOREIGN PATENT DOCUMENTS

| | | | |
|---|---|---|---|
| CA | 2415010 | A1 | 1/2002 |
| CN | 1440391 | A | 9/2003 |
| CN | A 1440391 | | 9/2003 |
| DE | 224422 | A1 | 3/1985 |
| EP | 333156 | A2 | 9/1989 |
| EP | 713143 | A2 | 5/1996 |
| EP | 780730 | A2 | 6/1997 |
| EP | 1 300 398 | A1 | 4/2003 |

(Continued)

OTHER PUBLICATIONS

Office Action dated Sep. 1, 2009 issued in corresponding Indian Application No. 3481/KOLNP/2006.
Office Action dated Sep. 1, 2009 issued in Indian Application No. 3481/KOLNP/2006 corresponding to co-pending U.S. Appl. No. 10/588,485.
Simone, Oncology: Introduction, Cecil Textbook of Medicine, 20.sup.th Edition, vol. 1, pp. 1004-1010, 1996.
Huirne et al., PubMed Abstract (Lancet 358(9295):1793-803), Nov. 2001. . Gonadotropin-releasing-hormone-receptor antagonists.
Jaro Komenda et al., Electrochemical Behavior and ESR Spectra of Nitro Substituted Mono-to and Debenzoylmethylenebenzthiazolines and Selenazolies, Collect. Czech. Chem. Commun. (1979), vol. 44(5), pp. 1540-1551.

(Continued)

*Primary Examiner* — Laura L. Stockton
(74) *Attorney, Agent, or Firm* — Sughrue Mion, PLLC

(57) ABSTRACT

It is intended to provide a compound useful as a GnRH receptor antagonist. The inventors further investigated propane-1,3-dione derivatives. As a result, they confirmed that a compound having a benzene ring or a thiophene ring substituted with a group represented by —$SO_2$—$R^3$ in a propane-1,3-dione derivative having 2-(1,3-dihydro-2H-benzimidazol-2-ylidene) has an excellent GnRH receptor antagonistic effect and accomplished the present invention. Because the compound of the present invention has a potent GnRH receptor antagonistic effect, it is useful for the treatment of sex hormone-dependent diseases, particularly GnRH-related diseases. Further, because the compound of the present invention has an excellent metabolic stability in human and few drug interactions, therefore it has preferable characteristics as a pharmaceutical used for the above-mentioned diseases.

19 Claims, No Drawings

FOREIGN PATENT DOCUMENTS

| | | | |
|---|---|---|---|
| EP | 1 752 452 | A1 | 2/2007 |
| JP | 56-161538 | A | 12/1981 |
| JP | 59-064840 | A | 4/1984 |
| JP | 62-006254 | A | 1/1987 |
| JP | 63-032542 | A | 2/1988 |
| JP | 63-271341 | A | 11/1988 |
| JP | 01-205130 | A | 8/1989 |
| JP | 1-248682 | | 10/1989 |
| JP | 01-249792 | A | 10/1989 |
| JP | 02-054268 | A | 2/1990 |
| JP | 02-079007 | A | 3/1990 |
| JP | 02-189547 | A | 7/1990 |
| JP | 03-164722 | A | 7/1991 |
| JP | 03-259150 | A | 11/1991 |
| JP | 04-334369 | A | 11/1992 |
| JP | 09-061992 | A | 3/1997 |
| JP | 2000-95767 | | 4/2000 |
| JP | 2002-088284 | A | 3/2002 |
| JP | 2002-241758 | A | 8/2002 |
| JP | 2002-268239 | A | 9/2002 |
| JP | 2004-061583 | A | 2/2004 |
| WO | WO 9804562 | A1 | 2/1998 |
| WO | WO 99/52888 | | 10/1999 |
| WO | WO 02/02533 | A1 | 1/2002 |
| WO | WO 02/102401 | A1 | 12/2002 |
| WO | WO 2005/030736 | A1 | 4/2005 |
| WO | WO 2005/097090 | A2 | 10/2005 |
| WO | WO 2005/118556 | A1 | 12/2005 |

OTHER PUBLICATIONS

A. Mistr et al., Organische Lichtempfindliche Stoffe V. Aclmethylenderivate Heterocyclischer Stickstoffhaltiger Basen ALS Sensibilisatoren Lichtempfindlicher Polymerer, Organic light-sensitive substances. Acylmethylene derivatives of heterocyclic nitrogen-containing bases as sensitizers for light-sensitive polymers, Collect. Czech. Chem. Commun. (1973), vol. 38(12), pp. 3616-3622, Abstract.

A. Mistr et al., Organische Lichtempfindliche Stoffee II. Benzoylmethylenderivate Heretocyclischer Stickstoffhaltiger Basen ALS Sensibilisatoren Fur Lichtempfindliche Polymere, Collect. Czech. Commun. (1971), vol. 36(1), pp. 150-163, Abstract.

Dzvinchuk LB., The Chemistry and Biological Activity of Synthetic and Natural Compounds: Nitrogen-Containing Heterocycles, vol. 1 (2006), pp. 243-248.

Manoj P. Samant., *Bioorganic & Medicinal Chemistry Letters*, vol. 15, Issue 11, Jun. 2, 2005, pp. 2894-2897 "Synthesis, in vivo and in vitro biological activity of novel azaline B analogs".

G.I. Gaeva and K.S. Liadikov, Sensitization of poly(vinyl cinnamate) by derivatives of benzoyl- and dibenzoylmethylenebenzothiazoline and -benzoselenazoline, Zh. Nauch. Prikl. Fotogr. Kinematogr. (1971) vol. 16(4), pp. 282-288, Abstract.

GH. Ciurdaru et al.,"The Acylation of 2-Methylbenzazoles" Journal fuer Praktische Chemie (Leipzig) (1979), 321(2), 320-2.

Mioslav Holik et al., "H-NMR Study of Transfer of substituent effects in 2-dibenzoylmethlylene-3-ethylbenzothiazolines and—senlenazolines." Collection of Czechoslovak Chemical Communications (1978), 43(3), 739-45.

Jisong Cui et al., "Identification of $Phe^{313}$ of the Gonadotropin-Releasing Hormone (GnRH) Receptor as a Site Critical for the Binding of Nonpeptide GnRH Antagonists" Molecular Endocrinology 14 671-681, 2000.

B. Byrne et al., "Functional analysis of GnRH receptor ligand binding using biotinylated GnRH derivatives" Molecullar and Cellular Endocrin. 144 11-19, 1998.

Tetsu Yano et al. "Effect of microcapsules of luteinizing hormone-releasing hormone antagonist SB-75 and somatostatin analog RC-160 on endocrine status and tumor growth in the Dunning R-3327H rat prostate cancer model."The Prostate 20 297-310, 1992.

Jacek Pinski et al., "Chronic administration of the luteinizing hormone-releasing hormone (LHRH) antagonist cetrorelix decreases gonadotrope responsiveness and pituitary LHRH receptor messenger ribonucleic acid levels in rats." Endocrinology 137 3430-3436, 1996.

Martin W. Rowbottom et al., "Synthesis and structure-activity relationships of (*R*)-1-alkyl-3-[2-(2-amino)phenethyl]-5-(2-fluorophenyl)-6-methyluracils as human GnRH receptor antagonists. Bioorg. Med. Chem. Lett." 14(9) 2269-2274, 2004.

Zhiqiang Guo et al., "Uracils as potent antagonists of the human gonadotropin-releasing hormone receptor without atropisomers." Bioorg. Med. Chem. Lett. 15(10) 2519-252, 2005.

Fabio C. Tucci et al., "Synthesis of orally active small-molecule gonadotropin-relea sing hormone antagonists." Curr.Opin. Drug Discovery Dev. 7, 832-847, 2004.

Joseph Pontillo et al., "Efficient synthesis of bicyclic oxazolino- and thiazolino[3,2-*c*]pyrimidine-5,7-diones and its application to the synthesis of GnRH antagonists". Bioorg. Med. Chem. Lett. 15(5) 1407-1411, 2005.

Miyuki Tatsuta et al., "Benzimidazoles as non-peptide luteinizing hormone-releasing hormone (LHRH) antagonists. Part 3: Discovery of 1-(1H-benzimidazol-5-yl)-3-tert-butylurea derivatives." Bioorg. Med. Chem. Lett. 15(9) 2265-2269, 2005.

Fabio Tucci et al., "3-(2-Aminoalkyl)-1-(2,6-difluorobenzyl)-5-(2-fluoro-3-methoxyphenyl)-6-methyl-uracils as Orally Bioavailable Antagonists of the Human Gonadotropin Releasing Hormone Receptor." J. Med. Chem. 2004, 47, 3483-3486.

Jinlong Jiang et al., "Syntheses and structure-activity relationship studies of piperidine-substituted quinolones as nonpeptide gonadotropin releasing hormone antagonists." Bioorg. Med. Chem. Lett. 14 1795-1798, 2004.

John T. Randolph et al. "Elimination of antibacterial activities of non-peptide luteinizing hormone-releasing hormone (LHRH) antagonists derived from erythromycin A" .Bioorg. Med. Chem. Lett. 14 1599-1602, 2004.

Zhiqiang Guo et al., "Synthesis and Structure-Activity Relationships of 1-Arylmethyl-5-aryl-6-methyluracils as Potent Gonadotropin-Releasing Hormone Receptor Antagonists." J. Med.Chem. 2004, 47, 1259-1271.

Fabio C. Tucci et al.,"Synthesis and Structure-activity relationships of 1-arylmethyl-3-(1-methyl-2-amino)ethyl-5-aryl-6-methyluracils as antagonists of the human GnRH Receptor." Bioorg. Med. Chem. Lett. 13 3317-3322, 2003.

Zhiqiang Guo et al., "Synthesis and structure-Activity relationships of thieno[2,3-*d*]pyrimidine-2,4-dione derivatives as potent GnRH receptor antagonists".Bioorg. Med. Chem. Lett. 13 3617-3622, 2003.

John T. Randolph "Nonpeptide Luteinizing Hormone-Releasing Hormone Antagonists Derived from Erythromycin A: Design, Synthesis, and Biological Activity of Cladinose Replacement Analogues." J.Med.Chem. 2004, 47, 1085-1097.

Kenna L. Anderes et al., "Gonadotropin-releasing hormone (GnRH) receptor antagonists have potential in treating numerous hormone-dependent pathologies including cancers of the prostate, breast, and ovary, endometriosis, and fertility disorders." J. Pharmaco. Experi. Ther. 305 688-695, 2003.

Takahito Hara et al., "Suppression of Pituitary-Ovarian Axis by Chronic Oral Administration of a Novel Nonpeptide Gonatropin-Releasing Hormone Antagonist, TAK-013, in Cynomolgus Monkeys"J. Clin. Endocri. Metab. 88 1697-1704, 2003.

Zhiqiang Guo., et al ,"Synthesis and Structure—Activity relationships of 1-arylmethyl-3-(2-aminopropyl)-5-aryl-6-methyluracils as potent GnRH receptor antagonists" Bioorg. Med. Chem. Lett. 13 3311-3315, 2003.

Yun-Fei Zhu et al., "Identification of 1-Arylmethyl-3-(2-aminoethyl)-5-aryluracil as Novel Gonadotropin-Releasing Hormone Receptor Antagonists." J.Med.Chem. 2003, 46, 2023-2026.

Keith M. Wilcoxen et al., "Synthesis and initial structure—Activity relationships of a novel series of imidazolo[1,2-*a*]pyrimid-5-ones as potent GnRH receptor antagonists" Bioorg. Med. Chem. Lett. 12 2179-2183, 2002.

Timothy D. Gross et al., "Design, synthesis and structure—Activity relationships of novel imidazolo[1,2-*a*]pyrimid-5-ones as potent GnRH receptor antagonists." Bioorg. Med. Chem. Lett. 12 2185-2187 2002.

Satoshi Sasaki et al., "Discovery of a Thieno[2,3 -d] pyrimidine -2,4-dione Bearing a p-Methoxyureidophenyl Moiety at the 6-position: A Highly Potent and Orally Bioabvailabel Non-Peptide Antagonist for the Human Luteinizing Hormone-Releasing Hormone Receptor" J.Med.Chem. 2003, 46, 113-124.

Satoshi Sasaki et al., "A new class of potent nonpeptide luteinizing hormone-releasing hormone (LHRH) antagonists: design and synthesis of 2-phenylimidazo[1,2-*a*]pyrimidin-5-ones." Bioorg. Med. Chem. Lett. 12 2073-2077, 2002.
Drugs of the Future "TAK-013" 2003, 28, 121.
David R. Luthin et al.,"Characterization of mono- and diaminopyrimidine derivatives as novel, nonpeptide gonadotropin releasing hormone (GnRH) receptor antagonists" Bioorg. Med. Chem. Lett. 12 3635-3639, 2002.
Joseph P. Simeone et al., "Modification of the pyridine moiety of non-peptidyl indole GnRH receptor antagonists" Bioorg. Med. Chem. Lett. 12 3329-3332, 2002.
David R. Luthin et al., "The discovery of novel small molecule non-peptide gonadotropin releasing hormone (GnRH) receptor antagonists." Bioorg. Med. Chem. Lett. 12 3467-3470, 2002.
Fabio C. Tucci et al., "A novel synthesis of 7-aryl-8-fluoro-pyrrolo[1,2-*a*]pyrimid-4-ones as potent, stable GnRH receptor antagonists." Bioorg. Med. Chem. Lett. 12 3491-3495, 2002.
Robert J. Devita et al., "A Potent, Nonpeptidyl 1*H*-Quinolone Antagonist for the Gonadotropin-Releasing Hormone Receptor." J.Med.Chem. 2001, 44, 917-922.
Yun-Fei Zhu et al., "Initial Structure-Activity Relationship Studies of a Novel Series of Pyrrolo[1,2-*a*]pyrimid-7-ones as GnRH Receptor Antagonists." Bioorg. Med. Chem. Lett. 12 399-402, 2002.
Yun-Fei Zhu et al., "A Novel Synthesis of 2-Arylpyrrolo[1,2-*a*]pyrimid-7-ones and Their Structure-Activity Relationships as Potent GnRH Receptor Antagonists." Bioorg. Med. Chem. Lett. 12 403-406 2002.
Feroze Ujjainwalla et al., "Total syntheses of 6- and 7-azaindole derived GnRH antagonists." Tetraherdron Lett. 42 6441-6445, 2001.
Joseph P. Simeone et al., "Synthesis of chiral β-methyl tryptamine-derived GnRH antagonists."Tetraherdron Lett. 42 6459-6461, 2001.
Wallace T. Ashton et al., "Orally bioavailable, indole-based nonpeptide GnRH receptor antagonists with high potency and functional activity." Bioorg. Med. Chem. Lett. 11 2597-2602, 2001.
Wallace T. Ashton et al., "Substituted Indole-5-carboxamides and -acetamides as Potent Nonpeptide GnRH Receptor Antagonists." Bioorg. Med. Chem. Lett. 11 1723-1726 2001.
Wallace T. Ashton et al., "Potent nonpeptide GnRH receptor antagonists derived from substituted indole-5-carboxamides and -acetamides bearing a pyridine side-chain terminus." Bioorg. Med. Chem. Lett. 11 1727-1731, 2001.
Thomas F. Walsh et al., "A convergent synthesis of (*S*)(β-methyl-2-aryltryptamine based gonadotropin releasing hormone antagonists." Tetraherdron 57 5233-5241, 2001.
Zhiqiang Guo et al., "Uracils as potent antagonists of the human gonadotropin-releasing hormone receptor without atropisomers." Bioorg. Med. Chem. Lett. 15 2519-2522, 2005.
Joseph Pontillo et al., "Synthesis of aryl-1,2,4-triazine-3,5-diones as antagonists of the gonadotropin-releasing hormone receptor." Bioorg. Med. Chem. Lett. 15 4363-4366 2005.
Zhiqiang Guo et al., "Structure-activity relationships of 1,3,5-triazine-2,4,6-triones as human gonadotropin-releasing hormone receptor antagonists." Bioorg. Med. Chem. Lett. 15 3685-3690, 2005.
Kentaro Hashimoto et al., "Benzimidazole derivatives as novel nonpeptide luteinizing hormone-releasing hormone (LHRH) antagonists. Part 1: Benzimidazole-5-sulfonamides c." Bioorg. Med. Chem. Lett. 15 799-803, 2005.
Yingfu Li et al., "Benzimidazole derivatives as novel nonpeptide luteinizing hormone-releasing hormone (LHRH) antagonists. Part 2: Benzimidazole-5-sulfonamides." Bioorg. Med. Chem. Lett. 15 805-807 2005.
Martin W. Rowbottom et al., "Synthesis and structure-activity relationships of (*R*)-1-alkyl-3-[(2-amino)phenethyl]-5-(2-fluorophenyl)-6-methyluracils as human GnRH receptor antagonists." Bioorg. Med. Chem. Lett. 14 2269-2274 2004.
Robert J. Devita et al., "Identification of neutral 4-*O*-alkyl quinolone nonpeptide GnRH receptor antagonists. Bioorg." Med. Chem. Lett. 14 5599-5603 2004.
Robert J. Devita et al., "Identification and Initial Structure-Activity Relationships of a Novel Non-Peptide Quinolone GnRH Receptor Antagonist." Bioorg. Med. Chem. Lett. 9 2615-2620 1999.
Robert J. Devita et al., "Investigation of the 4-O-Alkylamine Substituent of Non-Peptide Quinolone GnRH Receptor Antagonists." Bioorg. Med. Chem. Lett. 9 2621-2624 1999.
Jonathan R. Young et al., "Quinolones as Gonadotropin Releasing Hormone (GnRH) Antagonists : Simultaneous Optimization of the C(3)-Aryl and C(6)-Substituents" Bioorg. Med. Chem. Lett. 10 1723-1727 2000.
Yun-Fei Zhu et al., "Nonpeptide Gonadotropin Releasing Hormone Antagonists" Annual Reports in Medicinal Chemistry vol. 39 99-110 (2004).
Nobuo Cho et al., "Discovery of a Novel, Potent, and Orally Active Nonpeptide Antagonist of the Human Luteinizing Hormone-Releasing Hormone (LHRH) Receptor." J.Med.Chem. 1998, 41, 4190-4195.
Bernhard Kutscher et al., "Chemistry and Molecular Biology in the Search for New LHRH Antagonists." Angew. Chem. Int. Ed. Engl. 1997 36 2148-2161.
Robin D. Clark et al., "LH-RH Antagonists: Design and Synthesis of a Novel Series of Peptidomimetics" J.Med.Chem. 1989, 32, 2036-2038.
Tetsu Yano et al., "Effect of Microcapsules of Luteinizing Hormone-Releasing Hormone Antagonist SB-75 and Somatostatin Analog RC-160 on Endocrine Status and Tumor Growth in the Dunning R-3327H Rat Prostate Cancer Model" The Prostate(1992) 20 297-310.
Lin Chu et al., : "SAR Studies of Novel 5- Substituted 2 Arylindoles as Nonpeptidyl GnRH Receptor Antagonists" Bioorg. Med. Chem. Lett. 11 515-517, 2001.
Lin Chu et al., "Initial Structure-Activity Relationship of a Novel Class of Nonpeptidyl GnRH Receptor Antagonists: 2-Arylindoles" Bioorg. Med. Chem. Lett. 11 509-513, 2001.
Christopher A. Willoughby et al., "Combinatorial Synthesis of 3-(Amidoalkyl) and 3-(Aminoalkyl) -2- arylindole Derivatives: Discovery of Potent Ligands for a Variety of G-protein Coupled Receptors" Bioorg. Med. Chem. Lett. 12 93-96 2002.
Jonathan R. Young et al., "2-Aeylindoles as Gonadotropin Releasing Hormone (GnRH) Antagonists: Optimization of Tryptamine Side Chain." Bioorg. Med. Chem. Lett. 12 827-832 2002.
Takashi Imada et al., "Design, Synthesis, and Structure-Activity Relationships of Thieno [2,3-*b*] pyridine-4-one Derivatives as a Novel Class of Potent , Orally Active, Non-Peptide Luteinizing Hormone Releasing Hormone Receptor Antagonist" J.Med.Chem. (2006), 49, 3809-3825.
"GnRH Antagonist Treatment of Female Infertility" Drug of the Future(1999) 24(4) 393-403.
M.P. Samant et al., "Synthesis and biological activity of GnRH antagonists modified at position 3 with 3-(2-methoxy-5-pyridyl)-alanine" J. Peptide Res.(2005)65 284-291.
Sandor Bajusz et al.,"New Antagonist of LHRH" Int. J. Peptide Protein Res.(1988) 32 425-435.
Hermann M. Behre et al., "High Loading and Low Maintenance Doses of a Gonadotropin-Releasing Hormone Antagonist Effectively Suppress Serum Luteinizing Hormone, Follicle-Stimulating Hormone, and Testosterone Normal Men." J. Clinical Endocrinology and Metabolism(1997) 82 5 1403-1408.
Hermann M. Behre et al., "Effective Suppression of Luteinizing Hormone and Testosterone by Single Doses of New Gonadotropin-Releasing Hormone Antagonist Cetrorelix (SB-75) in Normal Men." J. Clinical Endocrinology and Metabolism(1992) 75 2 393-398.
Samuel M. McCann et al., "The Role of Nitric Oxide (NO) in Control of LHRH Release that Mediates Gonadotropin Release and Sexual Behavior." Current Pharma. Design(2003) 9 381-390.
Silke H. Hoffmann et al., "Residues with Transmembrane Helices 2 and 5 of the Human Gonadotropin-Releasing Hormone Receptor Contribute to Agonist and Antagonist Binding." Mol. Endocrinology(2000) 14(7) 1099-1115.
Guangcheng Jiang, et al., "GnRH Antagonists: A New Generation of Long Acting Analogues Incorporating ρ-Ureido-phenylalanines at Positions 5 and 6" J. Med. Chem. 2001, 44 453-467.
JM Matsoukas, et al. "Structure Elucidation and Conformational Analysis of Gonadotropin Releasing Hormone and Its Novel Synthetic Analogue [Tyr(OMe)$^5$, D-Lys$^6$, Aze$^9$NGHEt]GnRH: The Importance of Aromatic Clustering in the Receptor Binding Activity" Eur J Med Chem (1997) 32 927-940.
Dror Yahalom, et al. "Design and Synthesis of Potent Hexapeptide and Heptapeptide GondotropinRelasing Hormone Antagonists by Truncation of a Decapeptide Analogue Sequence", J. Med Chem. (2000) 43 2831-2836.
Joanne T. Blanchfield, et al. "The Stability of Lipidic Analogues of GnRH in Plasma and Kidney Preparations: The Steroselective Release of the Parent Peptide," Bioorganic & Medicinal Chemistry Letters (2005) 15 1609-1612.
Gabor Halmos, et al. "Changes in Subcellular Distribution of Pituitary Receptors for Luteinizing Hormone-Releasing Hormone (LH-RH) After Treatment with the LH-RH Antogonist Cetrorelix," Proceedings of the National Academy of Sciences of the United States of America (2002) 99 961-965.
Guangcheng Jiang, et al. "Betidamino Acid Scan of the GnRH Antagonist Acyline," J. Med. Chem. (1997) 40 3739-3748.
Jean E. Rivier, et al. "Design of Potent Dicyclic (4-10/5-8) Gonadotropin Releasing Hormone (GnRH) Antagonists," J. Med. Chem. (2000) 43 784-796.
Jean E. Rivier, et al. "Design of Monocyclic (1-3) and Dicyclic (1-3/4-10) Gonadotropin Releasing Hormone (GnRH) Antogonists," J. Med. Chem. (2000) 43 797-806.
Jean E. Rivier, et al. "Design of Dicyclic (1-5/4-10) Gonadotropin Releasing Hormone (GnRH) Antagonists," J. Med. Chem. (2000) 43 807-818.
Steven C. Koerber, et al. "Consensus Bioactive Conformation of Cyclic GnRH Antogonists Defined by NMR and Molecular Modeling," J. Med. Chem. (2000) 43 819-828.
Renate Petry, et al. "Secondary Structure of the Third Extracellular Loop Responsible for Ligand Selectivity of a Mammalian Gonadotropin-Releasing Hormone Receptor," J. Med. Chem. (2002) 45 1026-1034.
Manoj P. Samant, et al. "Iterative Approach to the Discovery of Novel Degarelix Analogues: Substitutions at Positions 3, 7, and 8. Part II," J. Med. Chem. (2005) 48 4851-4860.
K.-L. Kolho, et al. "Sexual Maturation of Male Rats Treated Postnatally With a Gonadotrophin-Releasing Hormone Antagonist," J. Endocrinol., Feb. 1988; 116: 241-246.
Marvin J. Karten, et al. "Gonadotropin-Releasing Hormone Analog Design. Structure-Function Studies Toward the Development of Agonists and Antagonists: Rationale and Perspective," Endocrine Rev.(1986) 7 (1) 44-66.
T. Kurian, et al. "Effect of Human Chorionic Gonadotrophin on Methallibure Inhibited Spermatogenesis in RANA TIGRINA During the Preparatory Period," Current Sci.(1987) 56 7 325-327.
M. A. Rea, et al. "Testosterone Maintains Pituitary and Serum FSH and Spermatogenesis in Gonadotrophin-Releasing Hormone Antagonist-Suppressed Rats," J Endocrinol 1986 108: 101-107.
Rosemary R. Grady, et al. "Differential Suppression of Follicle-Stimulating Hormone and Luteinizing Hormone Secretion in Vivo by a Gonadotropin-Releasing Hormone Antagonist," Neuroendocrinology(1985) 40 246-252.
K. Kato, et al. "Inhibition of Implantation and Termination of Pregnancy in the Rat by a Human Chorionic Gonadotrophin Antagonist," Endocrinology 1983 113: 195-199.
H.M. Fraser, et al. "Luteal Regression in the Primate: Different Forms of Cell Death During Natural and Gonadotrophin-Releasing Hormone Antagonist or Prostaglandin Analogue-Induced Luteolysis," Biology of Reproduction(1999) 61 1468-1479.
Yutaka Osuga, et al. "Derivation of Functional Antagonists Using N-Terminal Extracellular Domain of Gonadotrophin and Thyrotropin Receptors," Mol. Endocrinology(1997) 11 1659-1668.
A. M. Wolfe, et al. "Blockade of Singular Follicle-Stimulating Hormone Secretion and Testicular Development in Photostimulated Djungarian Hamsters (*Phodopus sungorus*) by a Gonadotropin-Releasing Hormone Antagonist," Biology of Reproduction(1995) 53 724-731.
W. Popek, et al. "The Effects of Bicuculline (a $GABA_A$ receptor antagonist) on LHRH-A and Pimozide Stimulated Gonadotropin (GtH2) Release in Female Carp (*Cyrinus carpio* L.)," Comp. Biochem. Physiol.(1994) 108C 1 129-135.
Margo R. Fluker, MD, "Gonadotropin-Releasing Hormone Antagonist," Current Opinion in Endocrinology & Diabetes(2000) 7 350-356.
A. S. McNeilly, et al. "Supressions of Pulsatile Luteinizing Hormone Secretion by Gonadotrophin-Releasing Hormone Antagonist Does Not Affect Episodic Progesteron Secretion or Corpus Luteum Function in Ewes," J Reprod. Fert.(1992) 96 865-874.
J. Rabinovici, et al. "Endocrine Effects and Pharmacokinetic Characteristics of a Potent New Gonadotropin-Releasing Hormone Antagonist (Ganirelix) with Minimal Histamine-Releasing Properties: Studies in Postmenopausal Women," J. Clin. Endocrinol. Metab. (1992) 75: 1220-1225.
K. Gordan, et al. "Evolving Role of Gonadotropin-Releasing Hormone Antagonists," TEM(1992) 3 (7) 259-263.
H. M. Fraser, et al. "Gonadotropin-Releasing Hormone Antagonist for Postpartum Contraception: Outcome for the Mother and Male Offspring in the Marmoset," J. Clin. Endocrinol. Metab.(1994) 78: 121-125.
R. J. Santen, et al. "Gonadotropin-Releasing Hormone: Physiological and Therapeutic Aspects, Angonists and Antagonists," Hormone Res.(1987) 28 88-103.
A. J. Rao, et al. "Effect of Constant Infusion of Gonadotropin Releasing Hormone (GnRH) Agonist Buserelin and Antagonist CDB 2085 A Using Osmotic Minipumps on Testicular Function in Adult Male Bonnet Monkey," andrologia(1990) 22 567-573.
E. S. Hiatt, et al. "Supression of Basal and GnRH-Stimulated Gonadotropin Secretion Rate in vitro by GnRH Antagonist: Differential Effects on Metestrous and Proestrous Pituitaries," Neuroendocrinology(1989) 50 158-164.
Notice of Allowance dated Dec. 18, 2009 issued in U.S. Appl. No. 10/588,485.
Mexican Office Action dated May 26, 2009 issued in a counterpart Mexican application for U.S. Appl. No. 10/588,485.
Canadian Office Action dated May 28, 2009 issued in a counterpart Canadian application for U.S. Appl. No. 10/588,485.
Masaaki Hirano et al., U.S. Appl. No. 10/588,485, entitled "Propane-1,3-dione Derivative or Salt Thereof," filed Aug. 4, 2006.
Election of Species Requirement issued in Corresponding case U.S. Appl. No. 10/588,845 on Mar. 18, 2009.
Response to Election of Species Requirement and Third Preliminary Amendment filed in U.S. Appl. No. 10/588,845, filed May 18, 2009.
Non-Final Office Action dated Jul. 28, 2009, issued in U.S. Appl. No. 10/588,485.
New Zealand Office Action dated Aug. 27, 2009 issued in corresponding New Zealand Application No. 561387.
Amendment under 37 C.F.R. § 1.111 and Statement of Substance of Interview dated Oct. 28, 2009, filed in U.S. Appl. No. 10/588,485.
Supplemental Amendment Under 37 C.F.R. § 1.111 filed Nov. 10, 2009 in the co-pending U.S. Appl. No. 10/588,485.
Russian Office Action issued in corresponding Russian Application No. 2007140244/04(044048) dated Oct. 15, 2009, English translation.
Horumon to Rinsyo (Hormones and Clinical Medicine), spring extra No. 46, 46-57 (1998).
Charles Huggins et al., "Studies on Prostatic Cancer", Cancer Research, 1, 293-297 (1941).
L. Bokser et al., "Prolonged Inhibition of Luteinizing Hormone and Testosterone Levels in Male Rats with the Luteinizing Hormone-Releasing Hormone Antagonist SB-75", Proc. Natl. Acad. Sci. USA, 87, pp. 7100-7104, Sep. 1990.
S. Bajusz et al., "Highly potent antagonists of luteinizing hormone-releasing hormone free of edematogenic effects", Proc. Natl. Acad. Sci. USA, 85, pp. 1637-1641, Mar. 1988.
John Trachtenberg et al., "A Phase 3, Multicenter, Open Label, Randomized Study of Abarelix Versus Leuprolide Plus Daily Antiandrogen in men with Prostate Cancer", The Journal of Urology, vol. 167, 1670-1674, Apr. 2002.
Ana Maria Comaru-Schally et al., "Efficacy and Safety of Luteinizing Hormone-Releasing Hormone Antagonist Cetrorelix in the Treatment of Symptomatic Benign Prostatis Hyperplasia," Journal of Clinical Endocrinology and Metabolism, vol. 83, No. 11, pp. 3826-3831 (1998).

Fabio C. Tucci et al., "3-[(2*R*)-Amino-2-phenylethyl]-1-(2,6-difluorobenzyl)-5-(2-fluoro-3-methoxyphenyl)-6-methylpyrimidin-2,4-dione(NBI 42902) as a Potent and Orally Active Antagonist of the Human Gonadotropin-Releasing Hormone Receptor, Design, Synthesis, and in Vitro and in Vivo Characterization", J. Med. Chem. 48, 1169-1178, (2005).
Science of Synthesis, 24, 571-705 (2005).
I.B. Dzvinchuk et al., Formation of Unsymmetrical 2-(Diacylmethylene)-2,3-Dihydro-1H-Benzimidazoles During Acidotysis of 1-Benzoyl-2-(β-Benzoyloxy-β-Phenylvinyl)-1H-Benzimidazole), Chemistry of Heterocyclic Compounds, 37(5), 554-559 (2001).
Sema Öztürk et al., "Crystal Structure of 2-Dibenzoylmethyl Benzimidazole", Analytical Sciences, vol. 17, pp. 1133-1134, (2001).
Dzvinchuk, I.B. et al., "C-Monobenzoylation and dibenzoylation of 2-methylbenzimidazole by benzoyl chloride", Zhurnal Organicheskoi Khimii, 30(6), 909-914 (1994).
Manfred Augustin et al., "Synthesis and reactions of 2,2-diacylketene heteroacetals", Zeitschrift fuer Chemie (1980), 20(3), 96-7.
Jean Bourson, Benzimidazole series V. Behavior of 2-methylene-1,3-dimethylbenimidazoline. Alkylation and acylation reaction, Bulletin de la Societe Chimique de France (1974), (3-4, Pt. 2), 525-8.
Junko Ishida et al., "Antitumor Agents. Part 214: Synthesis and Evaluation of Curcumin Analogues as Cytotoxic Agents," Bioorganic & Medicinal Chemistry 10 (2002) 3481-3487.
Chinese Office Action dated Dec. 4, 2009 issued in the corresponding Chinese Application No. 200680008358.2.
Office Action issued on Feb. 25, 2010 in the counterpart Israeli Application No. 179437 of the co-pending U.S. Appl. No. 12/726,506, English Translation.
Office Action issued from Canadian Intellectual Property Office on May 5, 2010 in the counterpart Canadian Application No. 2,568,590 of co-pending U.S. Appl. No. 12/726,506.
Office Action issued from the Japanese Patent Office on Jun. 30, 2010, in the counterpart Japanese Application No. 2006-514134 of the co-pending U.S. Appl. No. 12/726,506.
Office Action issued from the Taiwanese Patent Office on Aug. 5, 2010, in the counterpart Taiwanese Application No. 94118378 of the co-pending U.S. Appl. No. 12/726,506.
Office Action issued Aug. 27, 2010 in counterpart Korean Application No. 10-2007-7025090.
Office Action issued Oct. 12, 2010 in counterpart Canadian Application No. 2,603,185.
Office Action issued on Nov. 26, 2010 from European Patent Office in corresponding European Application No. 06 730 589.6.

PROPANE-1,3-DIONE DERIVATIVE OR SALT THEREOF

TECHNICAL FIELD

The present invention relates to a novel propane-1,3-dione derivative useful as pharmaceuticals, especially as a therapeutical agent for sex hormone-dependent diseases.

BACKGROUND ART

It is known that hypothalamic hormone or pituitary hormone takes part in a control system of secretion of peripheral hormones. In general, secretion of anterior pituitary hormone is regulated by secretion stimulating hormones or secretion suppressing hormones secreted from its higher center, hypothalamus, or peripheral hormones secreted from the target organs of the respective hormones.

Gonadotropin releasing hormone (hereinafter, abbreviated as GnRH; also, GnRH is referred to as luteinizing hormone releasing hormone; LHRH) is known as a hormone which controls the secretion of sex hormones at the highest position, and regulates the secretion of luteinizing hormone (hereinafter, abbreviated as LH), follicle stimulating hormone (hereinafter, abbreviated as FSH), and sex hormones in the gonads through its specific receptor (hereinafter, abbreviated as GNRH receptor) which is present in anterior pituitary (Horumon to Rinsyo (Hormones and Clinical Medicine), spring extra number, 46, 46-57 (1998)). A specific and selective antagonist to the GnRH receptor is expected to be a drug for preventing and treating sex hormone-dependent diseases (e.g., prostate cancer, breast cancer, endometriosis, uterine fibroid, etc.), since it regulates the action of GnRH and controls the secretion of lower LH, FSH and sex hormones (Horumon to Rinsyo (Hormones and Clinical Medicine), spring extra number, (1998), ibid.; Cancer Res. 1, 293-297 (1941); Proc. Natl. Acad. Sci. USA 87, 7100-7104 (1990)).

At present, peptide compounds, cetrorelix (Proc. Natl. Acad. Sci. USA, 85, 1637-1641, 1988) and abarelix (J. Urol. 167, 1670-1674, 2002) are put on the market as GnRH receptor antagonists, and from these information, pharmaceuticals capable of controlling the secretion of sex hormones are also expected as therapeutical agents for benign prostatic hyperplasia (J. Clinical Endocrinology and Metabolism (1998) 83, 11, 3826-3831).

On the other hand, as non-peptidic compounds having a GNRH receptor antagonistic effect, for example, an uracil derivative, NBI-42902 (J. Med. Chem., 48, 1169-1178, 2005) was under clinical trials, but its development was stopped.

Patent Reference 1 discloses that a propane-1,3-dione derivative has a GnRH receptor antagonistic effect.

[Formula 1]

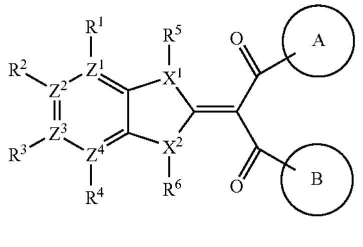

(In the formula, A and B are the same or different, each representing optionally substituted aryl or optionally substituted heterocyclic ring; for the details, referred to the above publication.)

However, there is no description of a substituted sulfonyl group ($-SO_2-R^3$) as the substituent on the ring A or the ring B or disclosure of specific compounds having such a group.

Further, Patent Reference 2 published after the priority date of the present application discloses that a propane-1,3-dione derivative has a GNRH receptor antagonistic effect.

[Formula 2]

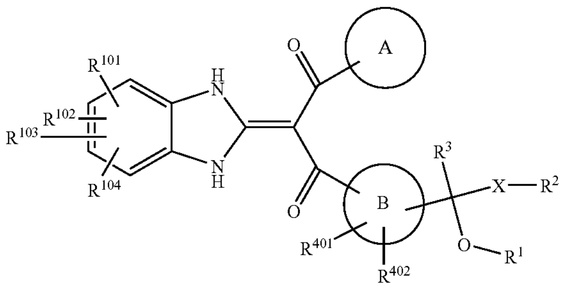

(In the formula, the ring A represents optionally substituted benzene, optionally substituted pyridine, or thiophene ring, and the ring B represents benzene or thiophene ring; for the details, referred to the above publication.)

However, the structure differs from the compound of the present invention in that the former has a substituent derived from a 1-hydroxyalkyl group on the ring B.

Patent Reference 1: International publication No. 02/02533 pamphlet

Patent Reference 2: International publication No. 05/118556 pamphlet

DISCLOSURE OF THE INVENTION

Problems to be Solved by the Invention

An object of the present invention is to provide a novel compound useful as a pharmaceutical that exhibits an excellent in vivo GnRH receptor antagonistic effect, especially as a therapeutical agent for prostate cancer, benign prostatic hyperplasia, etc.

Means for Solving Problems

The present inventors have further studied propane-1,3-dione derivatives. As a result, they have confirmed that 2-(1,3-dihydro-2H-benzimidazol-2-ylidene)-having propane-1,3-dione derivatives having a benzene ring or a thiophene ring substituted with a group of $-SO_2-R^3$ have an excellent GnRH receptor antagonistic effect and an excellent activity through oral administration, and have accomplished the present invention.

Specifically, the present invention relates to the following:

[1] A propane-1,3-dione derivative represented by the general formula (I) or a pharmaceutically acceptable salt thereof:

[Formula 3]

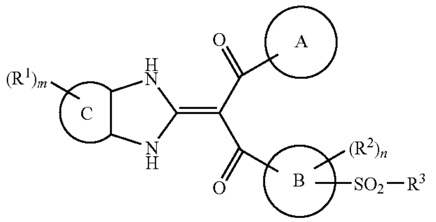

(I)

(wherein the symbols in the formula have the following meanings:

A: optionally substituted aryl or optionally substituted heteroaryl, ring B: benzene ring or thiophene ring, ring C: benzene ring or 5- to 7-membered aliphatic hydrocarbon ring optionally having a double bond in the ring, $R^1$: the same or different, each representing halogen, optionally substituted hydrocarbon group, —O-(optionally substituted hydrocarbon group), optionally substituted heterocyclic group, —S-(optionally substituted hydrocarbon group), —CO-(optionally substituted hydrocarbon group), —$CO_2$— (optionally substituted hydrocarbon group), —O—CO-(optionally substituted hydrocarbon group), —SO-(optionally substituted hydrocarbon group), —$SO_2$— (optionally substituted hydrocarbon group), —$NO_2$, —CN, —$CO_2H$, optionally substituted carbamoyl, optionally substituted sulfamoyl, or optionally substituted amino group, $R^2$: the same or different, each representing halogen, $R^0$, —O—$R^0$ or halogeno lower alkyl, m, n: the same or different, each indicating 0, 1 or 2, $R^3$: $R^0$, —OH, —O-optionally substituted heteroaryl, —N($R^{51}$)($R^{52}$), —N($R^{73}$)-N($R^{74}$)($R^{75}$),

[Formula 4]

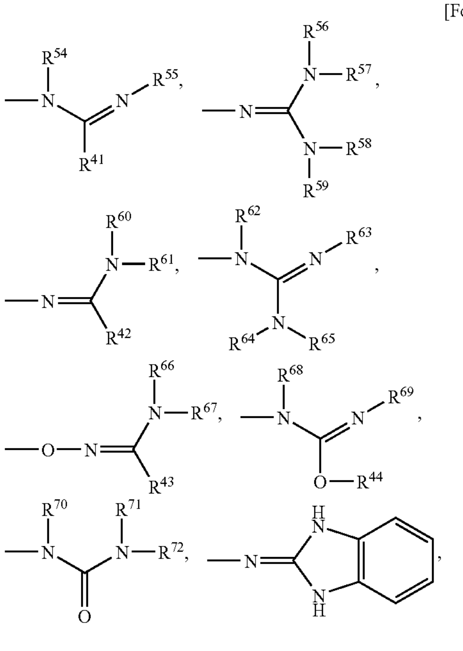

-continued

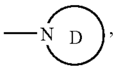

or, taken together with $R^2$, —N═C($R^{45}$)—NH— or —NH—C($R^{45}$)═N—, ring D: optionally substituted heterocyclic ring selected from the following group:

[Formula 5]

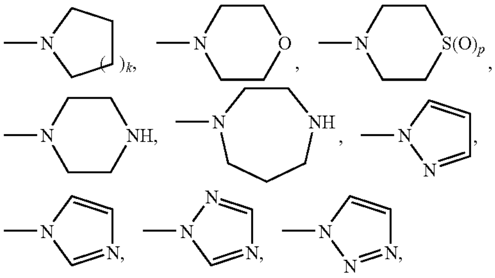

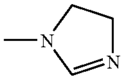

or

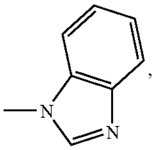

$R^0$: the same or different, each representing lower alkyl, $R^{00}$: the same or different, each representing lower alkylene, k: 1, 2, 3, or 4, p: 0, 1 or 2, $R^{41}$, $R^{42}$ and $R^{43}$: the same or different, each representing H, optionally substituted lower alkyl, —CHO, —CO-(optionally substituted lower alkyl), optionally substituted cycloalkyl, —$CO_2H$, —$CO_2$—$R^0$, —$CONH_2$, —CO—NH($R^0$), —CO—N($R^0$)$_2$, —$R^{00}$—CONH($R^0$), —$R^{00}$—CON($R^0$)$_2$, optionally substituted aryl, optionally substituted heterocyclic group, —$R^{00}$—O-aryl, —$R^{00}$—SO—$R^0$, —$R^{00}$—$SO_2$—$R^0$, —$R^{00}$—N(OH)—$R^0$ or —$R^{00}$—N(O—$R^0$)—$R^0$, $R^{44}$ and $R^{45}$: the same or different, each representing $R^0$ or —$R^{00}$-aryl, $R^{51}$ and $R^{52}$: the same or different, each representing H, optionally substituted lower alkyl, —$R^{00}$-(optionally substituted cycloalkyl), —$R^{00}$-(optionally substituted aryl), optionally substituted heteroaryl, —CO—$R^0$, —$CO_2$—$R^0$, —OH, —O—$R^0$, —O-benzyl, —$R^{00}$—O—$R^{00}$—OH or optionally substituted cycloalkyl, $R^{54}$, $R^{55}$, $R^{57}$, $R^{58}$, $R^{61}$, $R^{64}$, $R^{67}$, $R^{68}$, $R^{70}$, $R^{72}$, $R^{73}$ and $R^{74}$: the same or different, each representing H or $R^0$, $R^{56}$, $R^{59}$, $R^{66}$, $R^{69}$ and $R^{71}$: the same or different, each representing H, $R^0$ or —CO—$R^0$, $R^{60}$: H, $R^0$, —$R^{00}$—OH or —CO—$R^0$, $R^{62}$: H, $R^0$, —O—$R^0$ or —O-benzyl, $R^{63}$: H, $R^0$, —$NH_2$ or —CO—$R^0$, $R^{65}$: H, $R^0$, —$R^{00}$—OH, —$CONH_2$ or —CO—$R^0$, $R^{75}$: H, $R^0$, —$R^{00}$-aryl, aryl or heteroaryl, and $R^{54}$ and $R^{41}$, $R^{57}$ and $R^{58}$, $R^{61}$ and $R^{42}$, $R^{68}$ and $R^{44}$, $R^{62}$ and $R^{63}$, $R^{62}$ and $R^{65}$, and $R^{63}$ and $R^{65}$, each taken together, may form lower aklene optionally substituted with oxo group; provided that, when A is phenyl substituted with —CH(OH)—$CH_2$—OH, and when m and n are both 0, then $R^3$ means a group except —N($CH_3$)$_2$ the same shall be applied hereinafter);

[2] The compound of [1], wherein the ring C is benzene ring;

[3] The compound of [2], wherein the ring B is benzene ring;

[4] The compound of [3], wherein A is optionally substituted phenyl, optionally substituted naphthyl, optionally substituted thienyl, optionally substituted pyridyl, optionally substituted thiazolyl, benzofuranyl, or dihydrobenzofuranyl;

[5] The compound of [4], wherein $R^3$ is —N($R^{51}$)($R^{52}$) or a group selected from the following:

[Formula 6]

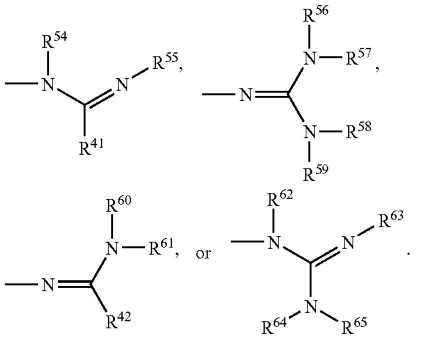

or

[6] The compound of [5], wherein m is 0;

[7] A propane-1,3-dione derivative of the general formula (Ia) or a pharmaceutically acceptable salt thereof:

[Formula 7]

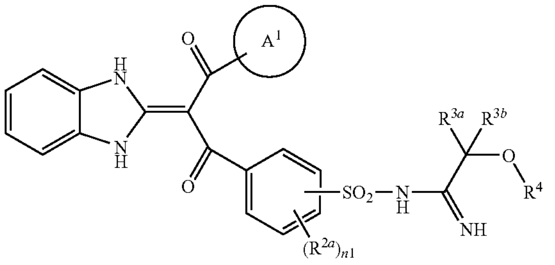

(Ia)

(wherein the symbols in the formula have the following meanings:

$A^1$: phenyl or thienyl, each of which is optionally substituted with the same or different one to three substituents selected from the following group G:

Group G: halogen, lower alkyl or —O-lower alkyl, $R^{2a}$: halogen, lower alkyl or —O-lower alkyl, $R^{3a}$, $R^{3b}$: the same or different, each representing H or lower alkyl, $R^4$: H, —C(═O)-lower alkyl or —C(═O)-heteroaryl, n1: 0 or 1);

[8] The compound of [1] selected from the following group:

(2R)-N-({3-[2-(1,3-dihydro-2H-benzimidazol-2-ylidene)-3-(3-fluorophenyl)-3-oxopropanoyl]phenyl}sulfonyl)-2-hydroxypropanimidamide, N-({3-[2-(1,3-dihydro-2H-benzimidazol-2-ylidene)-3-(3-fluorophenyl)-3-oxopropanoyl]phenyl}sulfonyl)-2-hydroxy-2-methylpropanimidamide, N-({5-[2-(1,3-dihydro-2H-benzimidazol-2-ylidene)-3-(3-fluorophenyl)-3-oxopropanoyl]-2-fluorophenyl}sulfonyl)-2-hydroxy-2-methylpropanimidamide, (2R)-N-({5-[2-(1,3-dihydro-2H-benzimidazol-2-ylidene)-3-(3-fluorophenyl)-3-oxopropanoyl]-2-fluorophenyl}sulfonyl)-2-hydroxypropanimidamide, (2R)-N-({5-[2-(1,3-dihydro-2H-benzimidazol-2-ylidene)-3-(3-methylphenyl)-3-oxopropanoyl]-2-fluorophenyl}sulfonyl)-2-hydroxypropanimidamide, N-({5-[3-(3,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide, (2R)-N-({5-[3-(3,5-difluorophenyl)-2-(1,3-dihydro-2H-benzimidazol-2-ylidene)-3-oxopropanoyl]-2-fluorophenyl}sulfonyl)-2-hydroxypropanimidamide, (2R)-N-({5-[3-(3-chlorophenyl)-2-(1,3-dihydro-2H-benzimidazol-2-ylidene)-3-oxopropanoyl]-2-fluorophenyl}sulfonyl)-2-hydroxypropanimidamide, N-({5-[2-(1,3-dihydro-2H-benzimidazol-2-ylidene)-3-oxo-3-(2,4,5-trifluorophenyl)propanoyl]-2-fluorophenyl}sulfonyl)-2-hydroxy-2-methylpropanimidamide, (2R)-N-({5-[2-(1,3-dihydro-2H-benzimidazol-2-ylidene)-3-oxo-3-(2,4,5-trifluorophenyl)propanoyl]-2-fluorophenyl}sulfonyl)-2-hydroxypropanimidamide, (2R)-N-({5-[2-(1,3-dihydro-2H-benzimidazol-2-ylidene)-3-(3-fluoro-4-methylphenyl)-3-oxopropanoyl]-2-fluorophenyl}sulfonyl)-2-hydroxypropanimidamide, (2R)-N-({5-[3-(2,5-difluorophenyl)-2-(1,3-dihydro-2H-benzimidazol-2-ylidene)-3-oxopropanoyl]-2-fluorophenyl}sulfonyl)-2-hydroxypropanimidamide, N-({5-[3-(2,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide, (2R)-N-({5-[3-(5-chloro-2-thienyl)-2-(1,3-dihydro-2H-benzimidazol-2-ylidene)-3-oxopropanoyl]-2-fluorophenyl}sulfonyl)-2-hydroxypropanimidamide, N-({5-[3-(5-chloro-2-thienyl)-2-(1,3-dihydro-2H-benzimidazol-2-ylidene)-3-oxopropanoyl]-2-fluorophenyl}sulfonyl)-2-hydroxy-2-methylpropanimidamide;

[9] A pharmaceutical composition comprising the compound of [1] as an active ingredient;

[10] The pharmaceutical composition of [9], which is a gonadotropin releasing hormone (GnRH) receptor antagonist;

[11] The pharmaceutical composition of [10], which is a therapeutical agent for prostate cancer, benign prostatic hyperplasia, breast cancer, endometriosis and/or uterine fibroid;

[12] Use of the compound of [1], for the manufacture of a gonadotropin releasing hormone (GNRH) receptor antagonist or a medicament for treating prostate cancer, benign prostatic hyperplasia, breast cancer, endometriosis and/or uterine fibroid;

[13] A method for treating prostate cancer, benign prostatic hyperplasia, breast cancer, endometriosis and/or uterine fibroid, comprising administering a therapeutically effective amount of the compound of [1] to a patient.

OUTCOMES OF THE INVENTION

The compounds of the present invention have a potent GnRH receptor antagonistic effect and additionally an excellent oral activity, and therefore are useful for treatment of sex hormone-dependent diseases, especially GnRH-related diseases, for example, prostate cancer, benign prostatic hyperplasia, breast cancer, endometriosis, uterine fibroid, etc. In addition, the compounds of the present invention have an excellent metabolic stability in human and few drug interactions, and therefore have preferable characteristics as pharmaceuticals for use for the above diseases.

BEST MODE FOR CARRYING OUT THE INVENTION

The present invention is described in detail hereinafter.

In this description, "alkyl" and "alkylene" mean linear or branched saturated hydrocarbon chains. "Lower alkyl" is an alkyl group having 1 to 6 carbon atoms, preferably methyl, ethyl, propyl, isopropyl, butyl, hexyl, etc. "Lower alkylene" means a divalent group derived from the above "lower alkyl" by removing any one hydrogen atom, preferably an alkylene having 1 to 4 carbon atoms, more preferably methylene, ethylene, methylmethylene, and propylene. "Lower alkenylene" is an alkenylene having 2 to 6 carbon atoms and having at least one double bond, concretely including vinylene, propenylene, 1-butenylene, 2-butenylene, etc. "Lower alkynylene" is an alkynylene having 2 to 6 carbon atoms and having at least one triple bond.

"Halogen" includes F, Cl, Br and I, preferably F, Cl. "Halogeno lower alkyl" means an alkyl having 1 to 6 carbon atoms and substituted with at least one halogen, preferably a $C_{1-6}$ alkyl substituted with at least one F, more preferably fluoromethyl, difluoromethyl, trifluoromethyl, and trifluoroethyl.

"Cycloalkyl" is a cycloalkyl having 3 to 10 carbon atoms, which may be bridged. Preferably, it is a cycloalkyl having 3 to 7 carbon atoms, more preferably cyclopropyl, cyclobutyl, cyclopentyl, cyclohexyl, and cycloheptyl. "Aryl" means a monocyclic, bicyclic or tricyclic aromatic hydrocarbon group having 6 to 14 carbon atoms, and includes a phenyl group fused with "cycloalkyl", for example, indanyl, tetrahydronaphthyl, fluorenyl. Preferably, it is phenyl or naphthyl, more preferably phenyl.

"Hydrocarbon group" is a group having 1 to 15 carbon atoms with hydrogen atoms, and includes the above-mentioned alkyl, cycloalkyl and aryl, as well as aryl-lower alkylene-, aryl-lower alkenylene-, aryl-lower alkynylene-, cycloalkyl-lower alkylene-, cycloalkyl-lower alkenylene- and cycloalkyl-lower alkynylene-.

"5- to 7-membered aliphatic hydrocarbon ring" means a saturated hydrocarbon ring having 5 to 7 carbon atoms with hydrogen atoms, and concretely includes cyclopentane, cyclohexane, and cycloheptane.

"Heteroaryl" is a generic term for a 5- or 6-membered monocyclic aromatic group having 1 to 4 hetero atoms selected from O, S and N (monocyclic heteroaryl), and a bicyclic heteroaryl formed through condensation of monocyclic heteroaryls or benzene ring and monocyclic heteroaryl, in which the ring atom, S or N may be oxidized to form an oxide or dioxide. The monocyclic aryl concretely includes pyridyl, pyrrolyl, pyrazinyl, pyrimidinyl, pyridazinyl, triazinyl, imidazolyl, triazolyl, tetrazolyl, thienyl, furyl, thiazolyl, pyrazolyl, isothiazolyl, oxazolyl, isoxazolyl, thiadiazolyl, oxadiazolyl. It further includes an tautomer of 2-hydroxypyridyl such as 2-oxo-1H-pyridyl. Preferred are thienyl, furyl, pyrrolyl, thiazolyl, pyridyl, pyrazinyl. The bicyclic heteroaryl concretely includes benzothienyl, benzofuryl, indazolyl, indolyl, benzimidazolyl, benzothiazolyl, benzoxazolyl, quinazolyl, quinoxalinyl, quinolyl, isoquinolyl, phthalazinyl. Preferred are benzofuryl and benzothienyl.

"Heterocyclic group" is a 3- to 7-membered, monocyclic or bicyclic heterocyclic group having 1 to 4 hetero atoms selected from O, S and N; and it includes a saturated cyclic group, the above-mentioned heteroaryl and a partially-hydrogenated cyclic group thereof. For example, it includes pyridyl, pyrazinyl, pyrimidinyl, pyridazinyl, imidazolyl, benzimidazolyl, benzofuranyl, benzothienyl, benzothiadiazolyl, benzothiazolyl, benzisothiazolyl, benzoxazolyl, benzisoxazolyl, pyrrolyl, pyrrolidinyl, thienyl, furyl, dioxanyl, dioxolanyl, triazinyl, triazolyl, tetrazolyl, thiazolyl, thiadiazolyl, oxadiazolyl, pyrazolyl, pyrazolidinyl, isothiazolyl, oxazolyl, isoxazolyl, quinolyl, isoquinolyl, tetrahydroquinolyl, tetrahydroisoquinolyl, quinazolinyl, quinoxalinyl, phthalazinyl, piperidyl, piperazinyl, azepanyl, diazepanyl, tetrahydrofuranyl, morpholinyl, methylenedioxyphenyl, ethylenedioxyphenyl, trithianyl, indolyl, isoindolyl, indolinyl, indazolyl, tetrahydrobenzimidazolyl, chromanyl, chromonyl (4-oxo-4H-1-benzopyranyl), benzimidazolonyl (2,3-dihydro-2-oxobenzimidazolyl), 2-oxo-1H-pyridyl. Preferred is a 5- to 6-membered monocyclic heteroaryl; and more preferred are furyl, thienyl, imidazolyl, thiazolyl, or pyridyl.

"Acyl" includes HCO—, hydrocarbon group-CO—, heterocyclic group-CO—, heterocyclic group-alkylene-CO—, heterocyclic group-alkenylene-CO—, heterocyclic group-alkynylene-CO—, hydrocarbon group-CS—, heterocyclic group-CS—, heterocyclic group-alkylene-CS—, heterocyclic group-alkenylene-CS—, heterocyclic group-alkynylene-CS—. Preferred are HCO—, hydrocarbon group-CO— and heterocyclic group-CO—; and more preferred are HCO—, acetyl, propionyl, benzoyl, nicotinoyl, thenoyl, pyrrolidinylcarbonyl or piperidylcarbonyl.

"Optionally substituted" means "unsubstituted" or "having the same or different one to five substituents". In case where the group has plural substituents, the substituents may be the same or different. Similarly, when m and/or n is 2, then two $R^1$'s and/or two $R^2$'s may be the same or different.

The substituent in "optionally substituted hydrocarbon group" is preferably —OH, —$NO_2$, —$CO_2H$, halogen, aryl, heterocyclic group, $R^{101}{}_3SiO$—, $R^{101}$-$T^{101}$-.

In this, $R^{101}$ is (1) H, (2) $C_{3-8}$ cycloalkyl, (3) heterocyclic group, (4) $C_{1-10}$ alkyl optionally substituted with [$C_{6-14}$ aryl optionally substituted with a group of $R^{102}$, —OH, —$NO_2$, —$CO_2H$, halogen, heterocyclic group, —CO—$C_{1-10}$ alkyl, —O—$C_{1-10}$ alkyl or —CO—O—$C_{1-10}$ alkyl], (5) $C_{6-14}$ aryl optionally substituted with [—OH, —CN, —$NO_2$, halogen or —$NR^{103}$—CO—$C_{1-10}$alkyl];

$R^{102}$ is halogen, —$NO_2$, —OH, —$CO_2H$, —O—$C_{1-10}$ alkyl or —CO—O—$C_{1-10}$ alkyl;

$R^{103}$ is (a) H, (b) $C_{3-8}$ cycloalkyl, (c) heterocyclic group, (d) $C_{1-10}$ alkyl optionally substituted with [$C_{6-14}$ aryl optionally substituted with a group of $R^{102}$, heterocyclic group optionally substituted with a group of $R^{102}$, —OH, —$NO_2$, —$CO_2H$, halogen, heterocyclic group, —CO—$C_{1-10}$ alkyl, —O—$C_{1-10}$ alkyl or —CO—O—$C_{1-10}$ alkyl], (e) $C_{6-14}$ aryl optionally substituted with [—OH, —CN, —$NO_2$, halogen or —$NR^{104}$—CO—$C_{1-10}$alkyl];

$R^{104}$ is (a) H, (b) $C_{3-8}$ cycloalkyl, (c) heterocyclic group, (d) $C_{1-10}$ alkyl optionally substituted with [—$CO_2H$, —CO—O—$C_{1-10}$ alkyl, $C_{6-14}$ aryl or heterocyclic group], (e) $C_{6-14}$ aryl optionally substituted with [—OH, —CN, —$NO_2$ or halogen];

$T^{101}$ is —O—, —CO—, —CO—O—, —O—CO—, —CO—$NR^{103}$—, —$NR^{103}$—CO— or —$NR^{103}$—. The same shall be applied hereinafter.

Of those, the substituent in "optionally substituted lower alkyl" is more preferably halogen, —OH, —O—$R^0$, —O—CO—$R^0$, —S—$R^0$, —CO—$R^0$, —O—CO-aryl, —O—$SO_2$—$R^0$, —O—$SO_2$-aryl, —O—$SO_2$-tolyl, —$N_3$, —$NH_2$, —NH($R^0$), —N($R^0$)$_2$, —CN, —$CO_2H$, —$CO_2$—$R^0$, —$CONH_2$, cycloalkyl, aryl; even more preferably halogen, —OH, —O—$R^0$, —S—$R^0$, cycloalkyl, aryl. The substituent in "optionally substituted aryl" is more preferably halogen, $R^0$, —OH, —O—$R^0$, —S—$R^0$, halogeno lower alkyl. The substituent in "optionally substituted cycloalkyl" is more preferably $R^0$, —OH, —O—$R^0$.

The substituent in "optionally substituted heterocyclic ring" is preferably (1) $C_{3-8}$ cycloalkyl, (2) $C_{6-14}$ aryl optionally substituted with $C_{1-10}$ alkyl-O—, (3) heterocyclic group, (4) $C_{1-10}$ alkyl optionally substituted with [$C_{6-14}$ aryl optionally substituted with a group of $R^{106}$, —OH, —$NO_2$, halogen, heterocyclic group, —$NR^{101}R^{103}$, —O—$C_{1-10}$ alkyl, —CO-hydrocarbon group or —CO-heterocyclic group]. More preferably, it is halogen, $R^0$, —OH, —O—$R^0$, —$R^{00}$—OH, —CO—$R^0$, —$CO_2$—$R^0$, halogeno lower alkyl, —O—$R^{00}$-aryl, —$CO_2$—$R^{00}$-aryl, aryl, heteroaryl; even more preferably halogen, $R^0$, —OH, —O—$R^0$, $R^{00}$—OH, halogeno lower alkyl, —O-benzyl, heteroaryl. The substituent in "optionally substituted heterocyclic ring" for the ring D is preferably —OH, $R^0$, —$NH_2$, —$R^{00}$—OH, halogeno lower alkyl.

"Optionally substituted carbamoyl", "optionally substituted sulfamoyl" or "optionally substituted amino group" means that one or two hydrogen atoms on the nitrogen atom therein may be substituted with any other group, in which the substituents may be the same or different. For the substituents, preferred are the group described for the substituents in "optionally substituted heterocyclic ring".

The substituent in "optionally substituted aryl" and "optionally substituted heteroaryl" for the ring A is preferably (1) —CN, (2) —$NO_2$, (3) halogen, (4) —OH, (5) —$CO_2H$, (6)-$T^{104}$-[$C_{1-10}$ alkyl optionally substituted with (—OH, halogen, heterocyclic group, $C_{6-14}$ aryl optionally substituted with halogen, —$NR^{101}R^{103}$, —CO—$R^{101}$, —CO-$T^{101}$-$R^{101}$ or -$T^{101}$-$R^{101}$)], (7) —CO-[hydrocarbon group optionally substituted with a group of $R^{105}$], (8) —CO-[heterocyclic group optionally substituted with a group of $R^{105}$], (9) —O-[acyl optionally substituted with a group of $R^{105}$], (10) —$NR^{106}R^{107}$, or (11) —CO—$NR^{106}R^{107}$.

In this, $T^{104}$ is a bond, —O—, —CO—O— or —O—CO—;

$R^{105}$ is —OH, —$CO_2H$, —CN, —$NO_2$, halogen, heterocyclic group, —$NR^{101}R^{103}$, $C_{1-10}$ alkyl optionally substituted with halogen, —O—$C_{1-10}$ alkyl, —CO—O—$C_{1-10}$ alkyl, $C_{6-14}$ aryl optionally substituted with [$C_{1-10}$ alkyl, —O—$C_{1-10}$ alkyl or —$NR^{101}$ acyl], acyl, —$NR^{101}$-acyl, or —$NR^{101}$—$SO_2$—($C_{6-14}$ aryl optionally substituted with $C_{1-10}$ alkyl);

$R^{106}$ and $R^{107}$ are the same or different, each representing H or a group of $R^{105}$. The same shall be applied hereinafter.

In addition, preferred embodiments of the present invention are described below.

(1) The ring A is preferably, optionally substituted, phenyl, naphthyl, pyridyl, pyrazyl, thiazolyl, dihydrobenzofuranyl, benzofuranyl or thienyl; more preferably, optionally substituted, phenyl, naphthyl, pyridyl, thiazolyl, dihydrobenzofuranyl, benzofuranyl or thienyl; even more preferably, optionally substituted, phenyl, naphthyl, pyridyl or thienyl. The substituent on the ring A is preferably halogen, $R^0$, —O—$R^0$, —OH, —O-aryl, —S—$R^0$, —$SO_2$—$R^0$, —CO—$R^0$, aryl, heteroaryl, —CN, halogeno lower alkyl; more preferably halogen, $R^0$, —O—$R^0$, —OH, —S—$R^0$, aryl, halogeno lower alkyl; even more preferably F, Cl, $R^0$, —O—$R^0$, halogeno lower alkyl.

(2) m is preferably 0 or 1, more preferably 0. $R^1$ is preferably halogen, optionally substituted hydrocarbon group, —O-(optionally substituted hydrocarbon group), —S-(optionally substituted hydrocarbon group), —CO-(optionally substituted hydrocarbon group), —$NO_2$, optionally substituted amino group; more preferably halogen, $R^0$, —O—$R^0$; even more preferably halogen.

(3) n is preferably 0 or 1. $R^2$ is preferably halogen, $R^1$, —O—$R^0$; more preferably halogen, $R^0$; even more preferably F. Regarding its position, the substituent $R^2$ is preferably at the ortho- or para-position relative to the group —$SO_2$—$R^3$; more preferably at the ortho-position.

(4) —$SO_2$—$R^3$ preferably bonds to the meta-position relative to the propanoyl chain.

(5) $R^3$ is preferably $R^0$, —N($R^1$)($R^2$),

[Formula 8]

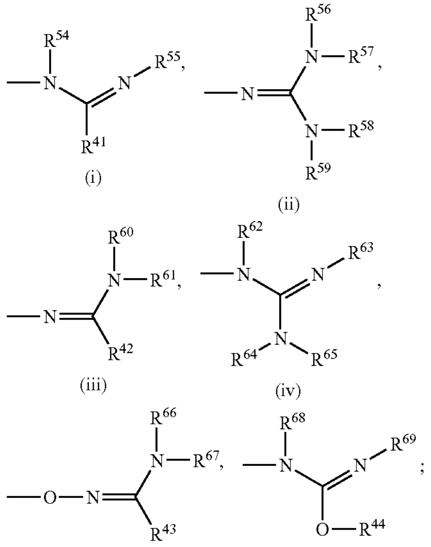

(i) (ii) (iii) (iv) (v) (vi)

more preferably, $R^0$, —N($R^{52}$)($R^{52}$), formula (i), formula (ii), formula (iii), formula (Iv); even more preferably formula (i), formula (iii).

Another preferred embodiment of $R^3$ is the following heterocyclic ring, and the ring may be substituted with a group selected from —OH, $R^0$, —$NH_2$, —$R^{00}$—OH, halogeno lower alkyl.

[Formula 9]

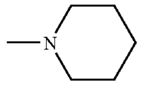

(6) $R^{41}$ and $R^{42}$ are preferably H, optionally substituted lower alkyl, —CO-(optionally substituted lower alkyl), optionally substituted cycloalkyl, —$CONH_2$, optionally substituted heterocyclic ring, —$R^{00}$—N(OH)—$R^0$, —$R^{00}$—N(O—$R^0$)—$R^0$; more preferably H, optionally substituted lower alkyl, —CO-(optionally substituted lower alkyl), optionally substituted cycloalkyl; even more preferably optionally substituted lower alkyl. The substituent in "optionally substituted lower alkyl" for $R^{41}$ and $R^{42}$ is preferably —$NH_2$, —N($R^0$)$_2$, —OH, —O—$R^0$, —O—CO—$R^0$, —O—CO-heteroaryl; more preferably —OH, —O—CO—$R^0$ or —O—CO-heteroaryl; even more preferably —OH. The heterocyclic ring is preferably pyridyl, pyrimidyl, thienyl, furyl, pyrrolyl.

(7) $R^{43}$ is preferably $R^0$; more preferably methyl.

(8) $R^{51}$ and $R^{52}$ are preferably H, optionally substituted lower alkyl, optionally substituted heteroaryl, —O—$R^0$;

more preferably H, optionally substituted lower alkyl. In this, the substituent in the lower alkyl and heteroaryl is preferably —OH or —O—$R^0$, more preferably —OH. The heteroaryl is preferably pyridyl or thiazolyl.

(9) $R^{54}$, $R^{55}$, $R^{60}$ and $R^{61}$ are preferably H, methyl; more preferably H.

(10) $R^{56}$, $R^{57}$, $R^{58}$ and $R^{59}$ are preferably H, methyl, —CO—$R^0$; more preferably H or acetyl; even more preferably H.

(11) $R^{62}$ is preferably H, —O—$R^0$; more preferably H.

(12) $R^{63}$ is preferably H, —$NH_2$, —CO—$R^0$; more preferably H.

(13) $R^{64}$ and $R^{65}$ are preferably H, methyl, —$R^{00}$—OH, —$CONH_2$, acetyl; more preferably H, methyl; even more preferably H.

(14) $R^{66}$, $R^{67}$, $R^{68}$, $R^{69}$, $R^{70}$ and $R^{72}$ are preferably H.

(15) $R^{44}$ is preferably $R^0$, more preferably methyl.

(16) $R^{71}$ is preferably H, $R^0$.

Especially preferred embodiments of the present invention are the compounds that comprise a combination of preferred groups of the above (1) to (16).

The compound (I) of the present invention includes geometric isomers via tautomers, and geometric isomers relative to the double bond at the 2-position of propane, as described below. Further, depending on the type of the substituent therein, the compound may include any other tautomers and geometric isomers. In this description, only one type of such isomers may be described, but the present invention encompasses these isomers, as well as isolated isomers or a mixtures thereof.

[Formula 10]

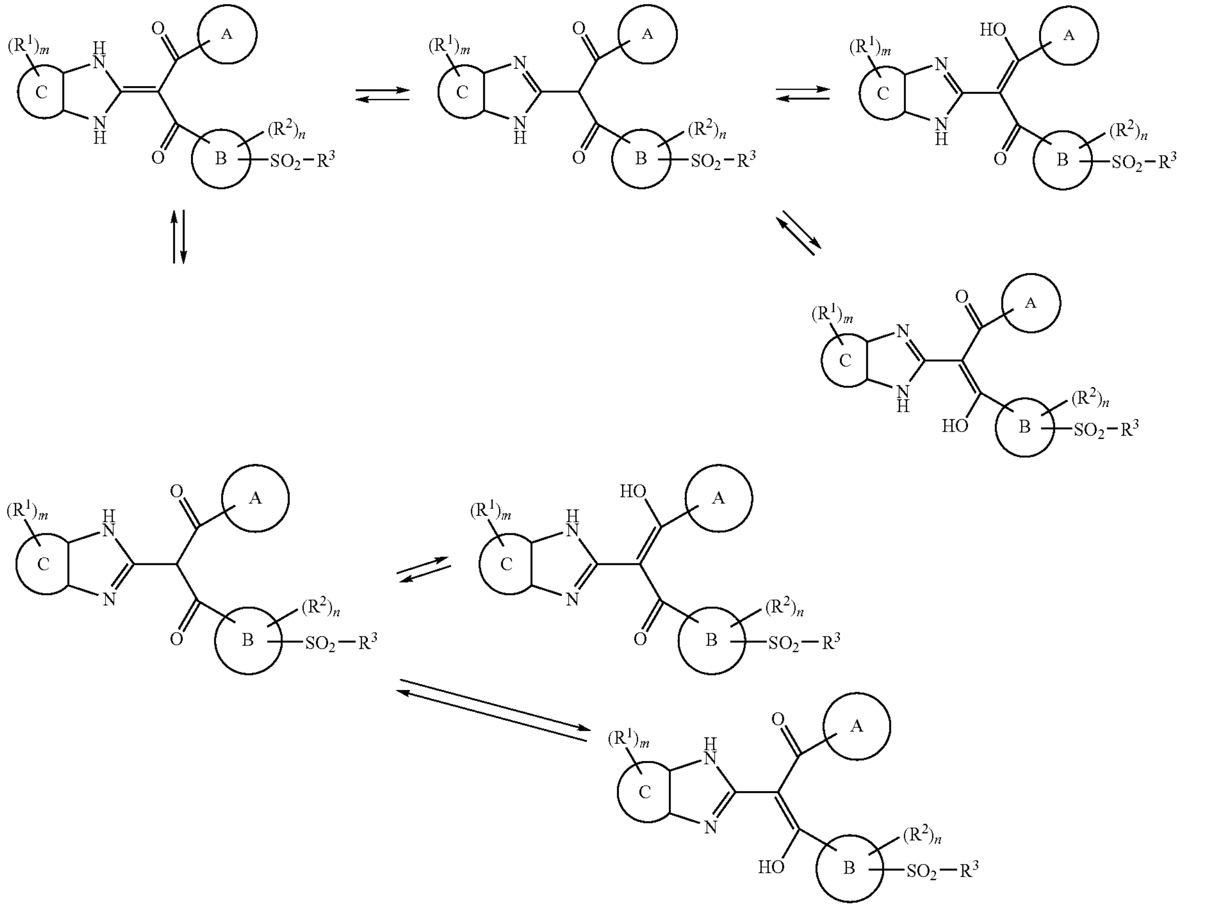

[Formula 11]

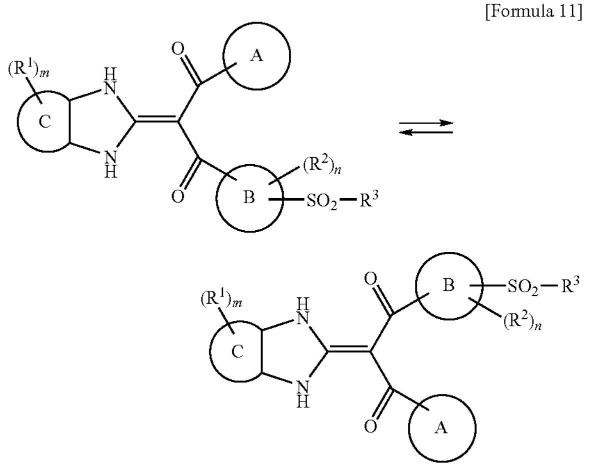

The compound (I) may have asymmetric carbon atoms or axial asymmetry, and based on it, the compound may includes optical isomers such as (R) form and (S) form, etc. The present invention includes all of mixtures of these isomers and isolated isomers.

Further, the present invention includes pharmaceutically acceptable prodrugs of compound (I). The pharmaceutically acceptable prodrugs are compounds having a group capable of being converted to amino group, OH, $CO_2H$ or the like of the present invention by solvolysis or under a physiological condition. Examples of a group to forms a prodrug are those described in Prog. Med., 5, 2157-2161 (1985), and those described in "PHARMACEUTICAL RESEARCH AND DEVELOPMENT" (Hirokawa Publishing, 1990), Vol. 7, Drug Design, pp. 163-198.

Further, the compound of the present invention may form acid-addition salts, or salts with bases depending on the type of the substituent therein. So far as the salts are pharmaceutically acceptable salts, they are within the scope of the present invention. Concretely, they includes acid-addition salts with an inorganic acid such as hydrochloric acid, hydrobromic acid, hydroiodic acid, sulfuric acid, nitric acid, phosphoric acid, etc.; or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, etc.; as well as salts with an inorganic base such as sodium, potassium, magnesium, calcium, aluminium, etc.; or an organic base such as methylamine, ethylamine, ethanolamine, lysine, ornithine, etc.; and ammonium salts or the like.

The present invention encompasses various hydrates, solvates and crystalline polymorphs of a compound of the present invention, as well as pharmaceutically acceptable salts thereof.

(Production Methods)

Utilizing characteristics based on the basic skeleton thereof or on the type of the substituent therein, the compound of the present invention and the pharmaceutically acceptable salt thereof can be produced by applying various known synthetic methods. Depending on the type of functional group, the functional group in the starting compounds-to-intermediate stage may be substituted with a protected group (group that may be readily converted to said functional group), and this may be technically effective in producing the compounds. The functional group includes, for example, an amino group, a hydroxyl group and a carboxyl group. Their protective groups are described, for example, in "Protective Groups in Organic Synthesis, (3rd Ed., 1999)" by Greene & Wuts, which can be appropriately selected and used according to the reaction condition. In this method, the protective group is removed if necessary after it has been introduced and the reaction carried out, to obtain the desired compound.

Prodrugs of compound (I) can be produced by introducing a specific group into the starting compounds-to-intermediate stage, as with the above-mentioned protective group thereinto, or by further processing the obtained compound (I). The reaction may be attained by applying methods known to persons skilled in the art, such as common esterification, amidation, dehydration, etc.

Typical production methods for the compounds of the present invention are described below. However, the production methods of the present invention should not be limited to the examples shown below.

Production Method 1:

[Formula 12]

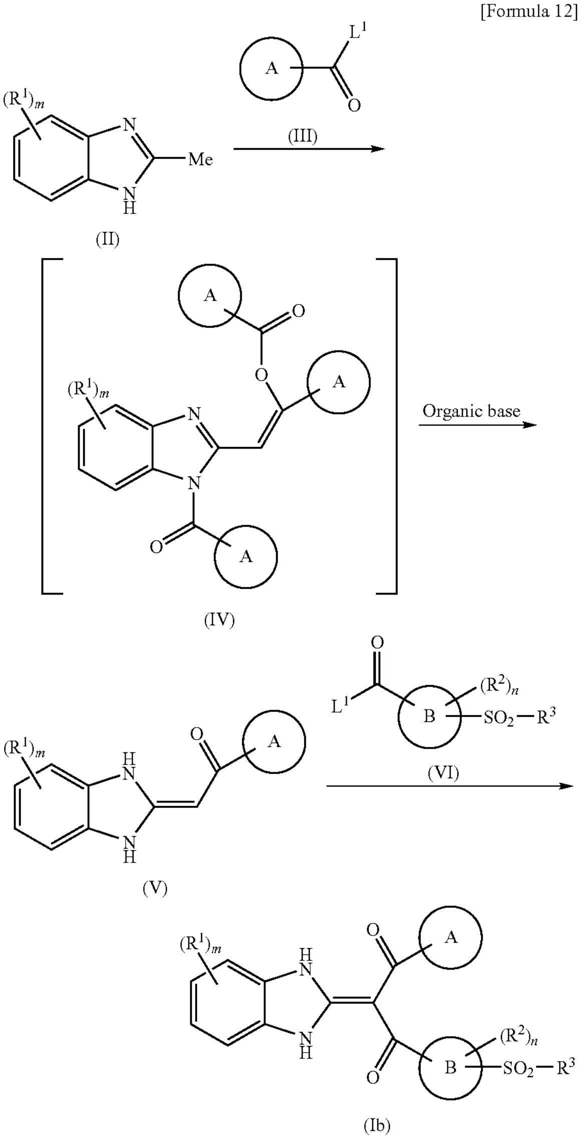

(II)
(IV)
(V)
(Ib)

(In the Formula, $L^1$ Represents a Leaving Group; and the Same Shall be Applied Hereinafter.)

This production method is a method for obtaining a compound of the general formula (Ib) of the present invention by reacting a 2-methylbenzimidazole compound (II) with a compound (III) and then with a phenylsulfonyl compound (VI). The leaving group for $L^1$ includes an organic sulfonic acid group such as methanesulfonyloxy or p-toluenesulfonyloxy, a halogen, or the like. Various acid anhydrides may be used as (III).

The reaction may be attained in no solvent or in a solvent inert to the reaction, under cooling to reflux conditions. The reaction temperature can be suitably determined depending on the compounds. The solvent for use includes aromatic hydrocarbons such as benzene, toluene, xylene; ethers such as diethyl ether, tetrahydrofuran (THF), dioxane, diglyme, 1,2-dimethoxyethane, 2-methoxydiethyl ether; halogenohydrocarbons such as dichloromethane, 1,2-dichloroethane, chloroform; acetonitrile, ethyl acetate, or the like; and one or more of these may be used either singly or as combined. The compound (II), the compound (III) and the compound (VI) may be used each in an equimolar amount or an excess amount, depending on the reaction and the compounds. With some compounds, it may be often advantageous to carry out the reaction in the presence of an organic base (preferably diisopropylethylamine, N-methylmorpholine, 4-(N,N-dimethylamino)pyridine, triethylamine, pyridine, collidine, morpholine, 2,6-lutidine) or an inorganic base (preferably sodium hydride, potassium carbonate, sodium carbonate, sodium hydrogencarbonate, sodium hydroxide, potassium hydroxide). The basic solvent may serve also as a base.

After isolated or without isolation, the compound (IV) may be reacted in the next step.

In this description, for convenience' sake, the structure of compounds (IV), compound (V) and the compounds in Reference Example corresponding to them, are expressed as a single configuration with respect to the geometric isomerism thereof to be caused by the double bond existing in these compounds; but some compounds may have geometric isomers relative to the double bond therein, and therefore the present invention includes those geometric isomers and their mixtures.

Production Method 2:

[Formula 13]

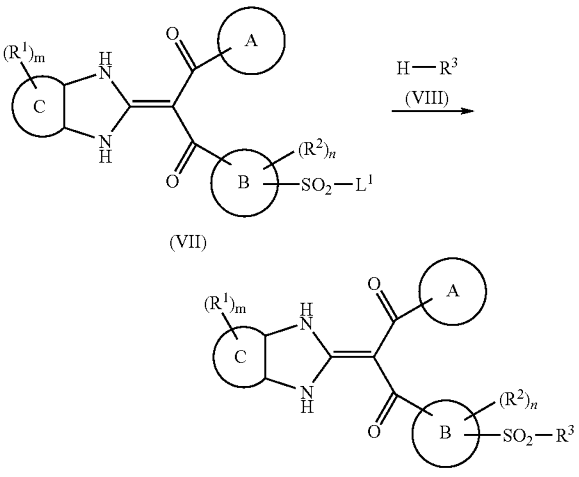

(VII)

(I)

This production method is for reaction of introducing a group corresponding to $R^3$ into a starting compound (VII); and for the compound (VIII), usable are various basic nitrogen-having compounds and hydroxyl group-having compounds.

The reaction can be attained in no solvent or in a solvent inert to the reaction, under cooling to reflux conditions. The reaction temperature can be suitably determined depending on the compounds. The solvent for use includes aromatic hydrocarbons, ethers, halogenohydrocarbons, N,N-dimethylformamide (DMF), N,N-dimethylacetamide (DMA), N-methylpyrrolidone (NMP), ethyl acetate, acetonitrile, pyridine, or the like; and one or more of these may be used either singly or as combined. The compound (VIII) can be used in an equimolar amount or an excessive amount. Depending on the type of the compound, it may be often advantageous to carry out the reaction in the presence of an organic base or an inorganic base.

The starting compound (VII) can be produced according to the above-mentioned production method 1. It may also be produced by preparing a sulfonic acid compound ($L^1$=OH) according to the production method 1, and processing it with a halogenating reagent such as thionyl chloride, oxalyl chloride, phosphorus oxychloride, or the like.

Production Method 3:

Compounds of general formula (I) having various substituent on the group $R^1$, $R^2$ or $R^3$ or on the ring A can be readily produced through reaction obvious to persons skilled in the art or modified methods thereof, starting from the compounds (I) of the present invention. For example, the following reaction is applicable thereto.

(1) Amidation, Sulfonamidation and Esterification:

Starting from a compound of the present invention having a hydroxyl group or an amino group and using a carboxylic acid or sulfonic acid compound or its reactive derivative, various amide compounds or ester compounds can be produced. Alternatively, starting from a compound of the present invention having a carboxylic acid or a sulfonic acid, it may be reacted with a compound having a hydroxyl group or an amino group.

The reaction is as follows: Using a reactive derivative (e.g., acid halide, acid anhydride, active ester) of a carboxylic acid or sulfonic acid compound, the method described for the above-mentioned production method 1 and production method 2 can be applied thereto. The reaction can also be attained in the presence of a condensing agent (e.g., dicyclohexylcarbodiimide (DCC), diisopropylcarbodiimide (DIPC), 3-ethyl-1-(3-dimethylaminopropyl)carbodiimide (WSC), 1,1'-carbonylbis-1H-imidazole (CDI), or as the case may be, further an additive (e.g., N-hydroxysuccinimide (HONSu), 1-hydroxybenzotriazole (HOBt), dimethylaminopyridine (DMAP)). The reaction can also be attained, for example, according to the method described in "Jikken Kagaku Koza (Courses in Experimental Chemistry, 4th Ed.)", Vol. 22 (1992) (Maruzen) edited by the Chemical Society of Japan.

The acylation on the nitrogen atom of sulfonamide can also be attained in the same manner.

(2) Oxidation:

A compound having a primary or secondary hydroxyl group can be oxidized to obtain a compound of the present invention having the corresponding aldehyde or ketone.

The reaction may be effected in a well-known method (ADVANCED ORGANIC CHEMISTRY (John WILEY & SONS (1992) by J. March), in which, for example, usable is an oxidizing agent such as m-chloroperbenzoic acid, hydrogen peroxide, tetrapropylammonium perruthenate, Dess-Martin reagent, in an solvent inert to the reaction such as halogenohydrocarbons.

(3) Ureide Formation:

A compound of the present invention having an amino group or a sulfonamido group may be reacted with an isocyanate compound or potassium cyanate to give the corresponding urea derivative as a compound of the present invention.

The reaction can be attained in a solvent inert to the reaction such as aromatic hydrocarbons, halogenohydrocarbons, DMF, NMP, acetonitrile, from room temperature to refluxing temperature. Adding an organic base or an inorganic base, or an acid such as acetic acid may be advantageous for the reaction.

The isocyanate compound can be obtained from its starting material, that is, a carboxylic acid or its reactive derivative, through well-known rearrangement (e.g., ADVANCED ORGANIC CHEMISTRY (John WILEY & SONS (1992) by J. March).

(4) Hydrolysis:

Hydrolysis of a carboxylate ester may give a compound of the present invention having a carboxyl group. The hydrolysis can be attained in any ordinary manner, to which, for example, applicable is the method of carboxyl deprotection described in the above-mentioned "Protective Groups in Organic Synthesis (3rd Ed.)".

(5) Reduction:

Well-known reduction reaction is applicable to reduction of nitro group to amino group, reduction of azido group to amino group and dehalogenation of halogen-substituted aromatic compounds (COMPREHENSIVE ORGANIC SYNTHESIS 8 REDUCTION (Pergamon Press (1991)).

For example, it includes (1) catalytic reduction to be attained under hydrogen atmosphere or in the presence of a hydrogen donor such as ammonium formate, using a catalyst such as palladium, platinum or nickel, in a solvent such as alcohols, e.g., methanol, ethanol, or chloroform, ethyl acetate or acetic acid, under cooling to heating conditions; (2) reaction using a metal such as iron or tin dichloride, in the presence of acetic acid or hydrochloric acid; or (3) reaction using a reducing agent such as sodium hydrosulfite, in a mixed solvent of water, alcohols, THF, under cooling to heating conditions.

(6) Amination or N-alkylation:

A compound having an alkyl halide or sulfonyloxy group may be reacted with various amines to give a compound of the present invention having an amino group. The amino group-having compound of the present invention may be reacted with any other alkylating agent whereby an alkyl group may be introduced thereinto. The alkylating agent is preferably alkyl halides, and organic sulfonates with alcohols.

The reaction may be attained in a solvent inert to the reaction such as aromatic hydrocarbons, halogenohydrocarbons, ethers, ketones (acetone, 2-butanone, etc.), acetonitrile, ethyl acetate, DMF, DMA or NMP, under cooling to heating conditions. The reaction in the presence of an organic base or an inorganic base may be advantageous to promote the reaction smoothly.

(7) Amidino Group and Guanidino Group:

A compound having an amidino group or a guanidino group can be obtained according to a well-known production method. For example, an amidino group-having compound can be produced according to the method described in "Jikken Kagaku Koza (Courses in Experimental Chemistry, 4th Ed.)", Vol. 20 (1992) (Maruzen) edited by the Chemical Society of Japan; and a guanidino group-having compound can be produced according to the method described in "COMPREHENSIVE ORGANIC FUNCTIONAL GROUP TRANSFORMATIONS" (Pergamon Press (1995)) by A. R. Katritzky, et al., Production Method 4:

[Formula 14]

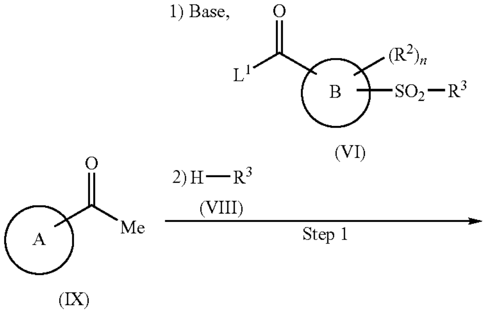

(VI)

(IX)

-continued

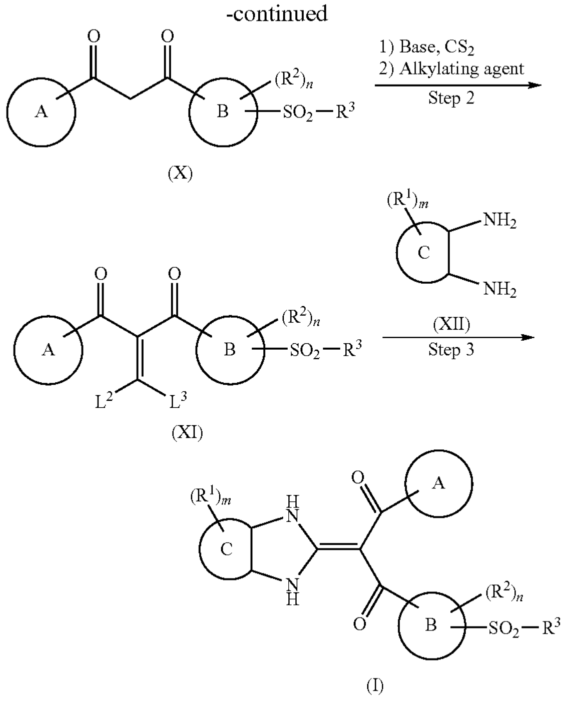

(X)

(XI)

(I)

(In the Formula, $L^2$ Represents —S-Lower Alkyl, and $L^3$ Represents —S-Lower Alkyl or Imidazole.)

Step 1:

This step is to obtain a 1,3-diketone derivative (X) through reaction of a methyl ketone derivative (IX) and a compound (VI) in the presence of a base followed by processing it with various compounds (VIII) having a basic nitrogen. The reaction can be attained in the presence of a strong base such as lithium diisopropylamide (LDA) in a solvent inert to the reaction such as ethers, e.g., tetrahydrofuran (THF), under cooling to reflux conditions.

Step 2:

This step is to obtain a compound (XI) in which $L^2$ and $L^3$ are both —S-lower alkyl through reaction of the 1,3-diketone derivative (X) with carbon disulfide ($CS_2$) in the presence of a base followed by processing it with a lower alkyl halide such as methyl iodide. The reaction can be attained in the presence of a base such as sodium hydride (NaH), in a solvent inert to the reaction, for example, an aprotic polar solvent such as N,N-dimethylformamide (DMF), under cooling to heating conditions. In this step, adding an additive such as potassium fluoride may be advantageous, as the case may be. In the series of reaction mentioned above, 1,1'-thiocarbonyldiimidazole may be used in place of carbon disulfide ($CS_2$) to give a compound (XI) where $L^2$ is —S-lower alkyl, and $L^3$ is imidazole.

Step 3:

This step is to obtain the compound of general formula (I) through reaction of the compound (XI) having two leaving groups with a diamine compound (XII).

The reaction can be attained in a solvent inert to the reaction, for example, alcohols such as ethanol, or an aprotic polar solvent such as dimethylsulfoxide (DMSO), under cooling to reflux conditions.

Compounds of the present invention are isolated and purified as free compounds, pharmaceutically acceptable salts, hydrates, solvates or crystalline polymorphorous substances thereof. Pharmaceutically acceptable salts of the compounds (I) of the present invention can be produced through ordinary salt formation reaction.

Isolation and purification can be attained through ordinary chemical operations such as extraction, fractional crystallization, various fractional chromatography.

Various kind of isomers can be isolated by selecting suitable starting compounds, or by separating them based on the difference between the isomers in the physicochemical properties thereof. For example, an optical isomer can be led into stereochemically-pure isomer through ordinary racemic resolution (for example by fractional crystallization to convert the compound into a diastereomer salt with an optically active base or acid; or by chromatography using a chiral column, etc.). It can also be produced from a suitable, optically active starting compound.

The pharmacological activities of the compounds of the present invention were confirmed by the tests mentioned below.

Test Example 1

Test for GnRH Receptor Antagonistic Effect

The GnRH receptor antagonistic effects of the compounds of the present invention were evaluated by calculating their concentration that inhibit 50% of the binding of $^{125}$I-D-Trp$^{6}$-LHRH to a human GnRH receptor ($IC_{50}$), according to the description in Patent Reference 1, page 56 "1. Test for GNRH Receptor Antagonistic Effect". The results are shown in Table 1.

TABLE 1

| Compound | $IC_{50}$ (nM) |
|---|---|
| Example 211 | 0.094 |
| Example 245 | 0.058 |
| Example 302 | 0.092 |
| Example 482 | 0.16 |
| Example 662 | 0.24 |
| Example 696 | 0.18 |

Patent Reference 1 mentioned above discloses a carbonyl group as the substituent on the phenyl group of propanoylphenyl, but does not disclose a sulfonyl group thereon. Accordingly, for confirming the usefulness of "group of —$SO_2$—$R^3$", the activities of the compounds of the present invention was compared with those of the comparative compounds having —CO—$R^3$ group. The results are shown in Table 2.

TABLE 2

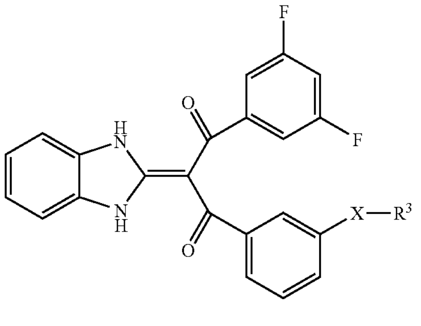

| Compound | X | $R^3$ | $IC_{50}$ (nM) |
|---|---|---|---|
| Example 73 | $SO_2$ | —NH—C(=NH)—Me | 0.053 |
| Comparative Example 1 | CO | | 7.1 |
| Example 89 | $SO_2$ | —N=C($NH_2$)$_2$ | 0.022 |

TABLE 2-continued

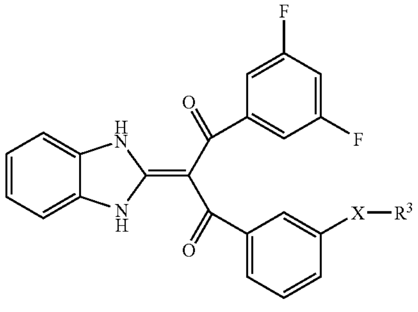

| Compound | X | $R^3$ | $IC_{50}$ (nM) |
|---|---|---|---|
| Comparative Example 2 | CO | | 5.0 |
| Example 74 | $SO_2$ | 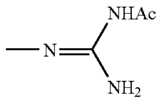 | 0.56 |
| Comparative Example 3 | CO | | 16 |
| Example 77 | $SO_2$ | —NH($CH_2$)$_2$OH | 0.066 |
| Comparative Example 4 | CO | | 9.6 |

As shown above, the compounds of the present invention having "group of —$SO_2$—$R^3$" exhibited an extremely more potent GNRH receptor antagonistic activities than the comparative compounds having —CO—$R^3$ group.

Test Example 2

Test for Antagonistic Effect to GnRH-Induced Blood Testosterone Increase Reaction The in vivo gonadotropin releasing hormone (GNRH) antagonistic effect of the compounds were evaluated by their inhibitory effects to blood testosterone increase reaction induced by GnRH administration in rats (Patent Reference 1, page 57). In the experiment, 9-week old Wistar male rats (Nippon SLC) were used. GNRH (Peptide Institute, LH-RH (human)) was administered intramuscularly in the hip of each rat (30 ng/rat). The test compounds were dissolved or suspended in an aqueous 0.5% methyl cellulose (MC) solution, and orally administered at a dose of 3 mg/kg, 2 or 6 hours prior to the GnRH administration. One hour after the GnRH administration, the blood was collected and the testosterone concentration in the serum was measured by specific radioimmunoassay (Iatron's RIA kit).

The inhibitory activity (%) (IA) of the test compounds were calculated according to a formula: $IA=(Tc-Ts)/(Tc-Tn)\times100$ (when lowered to Tn, IA=100%). In this formula, Tn indicates the serum testosterone concentrations of the rats without GnRH administration; Tc indicates those with the solvent instead of the test compounds administration; Ts indicates those with the test compounds administration. As a result, for example, the inhibitory activities of the compounds of Examples 211, 302, 662 and 696 were at least 90% at a dose of 3 mg/kg.

From the test results above, it is obvious that the compounds of the present invention are useful as a preventive/therapeutical agents for various sex hormone-dependent diseases such as prostate cancer, breast cancer, endometriosis, uterine fibroid, benign prostatic hyperplasia, etc., as having a potent GnRH receptor antagonistic effect.

A composition containing, as an active ingredient thereof, one or more of the compounds (I) of the present invention or the salts thereof can be prepared according to a method generally used in the art, using pharmaceutical carriers and excipients generally used in the art.

Therapeutic administration can be accomplished either by oral administration via tablets, pills, capsules, granules, powders, liquids, etc., or parenteral administration via intraarticular, intravenous or intramuscular injections, suppositories, eye drops, eye ointments, transdermal liquids, ointments, transdermal plasters, transmucosal solutions, transmucosal plasters, inhalers, etc.

According to the present invention, solid compositions for oral administration include tablets, powders or granules, etc., in which one or more active ingredients are mixed with at least one inactive excipient, such as lactose, mannitol, glucose, hydroxypropyl cellulose, microcrystalline cellulose, starch, polyvinylpyrrolidone and/or magnesium aluminometasilicate. According to standard methods, the composition may contain inactive additives, such as lubricants (e.g., magnesium stearate), disintegrators (e.g., carboxymethyl starch sodium), stabilizers, solubilization assisting agents. The tablets or pills may be coated with sugar or a film of a gastric or enteric substance, if necessary.

Liquid compositions for oral administration include pharmaceutically acceptable emulsions, solutions, suspensions, syrups, and elixirs, and contain a commonly used inert diluent such as purified water or ethanol. The liquid composition may contain, in addition to the inert diluent, auxiliary agents such as solubilization assisting agents, moistening agents, and suspending agents, as well as sweeteners, flavors, aromatics, and antiseptics.

Injections for parenteral administration include aseptic aqueous or non-aqueous solutions, suspensions or emulsions. Diluents for use in aqueous solutions include, for example, distilled water for injection use and physiological saline. Diluents for use in non-aqueous solutions include, for example, propylene glycol, polyethylene glycol, vegetable oil such as olive oil, alcohols such as ethanol, Polysorbate 80 (the name in the Japanese Pharmacopeia). Such compositions may further contain tonicity agents, antiseptics, moistening agents, emulsifiers, dispersants, stabilizers, or solubilization assisting agents. These compositions are sterilized by filtration through a bacteria-trapping filter, or by addition of germicide, or through irradiation. Furthermore, they may also be produced in the form of sterile solid compositions and dissolved or suspended in sterile solvent for injection prior to their use.

Transmucosal compositions, such as inhalers and transnasal agents, are used in solid, liquid or semi-solid, and can be produced according to conventional known methods. For example, known excipients and further pH adjusters, antiseptics, surfactants, lubricants, stabilizers and thickeners, etc. can be added if necessary. For administration, suitable devices for inhalation or insufflation can be used. For example, using known devices or sprayers such as a metered dose inhalers, the compound can be administered independently, or in the form of prescribed mixture powders. Furthermore, the compounds combined with pharmaceutically acceptable carriers can also be administered in the form of solutions or suspensions. Dry powder inhalers and the like may be devices for single or multiple administrations, Dry powders or capsules containing powders can also be used. Still further, the devices can be in the form of a pressure aerosol spray or the like using a suitable propellant, such as chlorofluoroalkane or hydrofluoroalkane, or a suitable gas such as carbon dioxide.

In the case of oral administration, a daily dose per body weight is usually about 0.001 to 100 mg/kg, preferably 0.1 to 30 mg/kg, more preferably 0.1 to 10 mg/kg. A dose can be administered once daily or by dividing it into from 2 to 4 doses. In the case of intravenous administration, the daily dose per body weight is appropriately about 0.0001 to 10 mg/kg and is administered once daily, or divided into multiple doses. In the case of transmucosal administration, the daily dose per body weight is appropriately about 0.001 to 100 mg/kg and is administered once daily, or it is divided into multiple doses. Doses are determined for each case according to symptom, age, sex, etc.

EXAMPLES

The production methods for the compounds (I) of the present invention are described in more detail with reference to the following Examples. The compounds of the present invention should not be limited to those described in the following Examples. The production methods for the starting compounds are shown in Reference Examples.

The abbreviations in Reference Examples, Examples and Tables mentioned below are as follows:

Ex: Number of Example
REx: Number of Reference Example
No.: Number of Compound
Dat: Physicochemical data (FA: FAB-MS $(M+H)^+$, FN: FAB-MS $(M-H)^-$, ES+: ESI-MS $(M+H)^+$, ES−: ESI-MS $(M-H)^-$, EI: EI-MS $(M^+)$, AP+: APCI-MS $(M+H)^+$, AP−: APCI-MS$(M-H)^-$, N1: δ (ppm) of characteristic peaks in $^1H$ NMR in DMSO-$d_6$, N2: δ (ppm) of characteristic peaks in $^1H$ NMR in $CDCl_3$)
Sal: Salt (HCl: hydrochloride, no mark: free form)
Str: Structural formula
pos: Substituent position
Syn: Production method (Numeral alone means the number of Example as referred to in producing the compound in the same manner; numeral with R means the number of Reference Example as referred to in producing the compound in the same manner. For example, R1 means that the compound is produced in the same manner as in Reference Example 1.)
Not Isolated Not isolated
Me: methyl
Et: ethyl
Pr: propyl
iPr: 2-propyl
cPr: cyclopropyl
Bu: butyl
tBu: tert-butyl
Boc: tert-butoxycarbonyl
cBu: cyclobutyl
Ms: methanesulfonyl
Ts: p-toluenesulfonyl
Ph: phenyl
2Py: 2-pyridyl
3Py: 3-pyridyl
4Py: 4-pyridyl
1Naph: 1-naphthyl
2Naph: 2-naphthyl
Ac: acetyl
Piv: pivaloyl
Bn: benzyl
2Fur: 2-furyl
3Fur: 3-furyl
4THP: tetrahydropyran-4-yl
2THF: tetrahydrofuran-2-yl Pyra: pyrazin-2-yl
2Thi: 2-thienyl
3Thi: 3-thienyl The numeral before the substituent indicates the substituent position; and plural numerals indicate substitution with plural substituents. For example, 3,5-diMe-Ph means 3,5-dimethylphenyl.

Reference Example 1

3-Fluorobenzoyl chloride was added to a mixture of 2-methylbenzimidazole, triethylamine and dioxane, followed by heating under reflux for 3 hours and cooling to room temperature. Morpholine was added, followed by stirring under heat at 70° C. for 1 hour and work-up to obtain 1-(3-fluorophenyl)-2-(1,3-dihydro-2H-benzimidazol-2-ylidene)ethanone.

Reference Example 2

1-(3,5-Difluorophenyl)-2-(1,3-dihydro-2H-benzimidazol-2-ylidene)ethanone and 3-(chlorosulfonyl)benzoyl chloride were heated under reflux in dioxane for 1 hour, followed by cooling. After dilution with ethyl acetate, the insoluble matter was separated by filtration. The filtrate was concentrated under reduced pressure, and the resulting residue was purified by silica gel column chromatography. This was further diluted with ethyl acetate, washed with an aqueous saturated sodium hydrogencarbonate solution and water successively, dried over anhydrous magnesium sulfate, and the solvent was evaporated under reduced pressure to obtain 3-[3-(3,5-difluorophenyl)-2-(1,3-dihydro-2H-benzimidazol-2-ylidene)-3-oxopropanoyl]benzenesulfonyl chloride.

Reference Example 3

A chloroform solution of tetrahydro-2H-thiopyran-4-carbonitrile was dropwise added to a chloroform solution of 77% m-chloroperbenzoic acid at 0° C., followed by stirring at room temperature for 3 hours. An excess amount of an aqueous saturated sodium sulfite solution was added, followed by work-up to obtain tetrahydro-2H-thiopyran-4-carbonitrile 1,1-dioxide.

Reference Example 4

The compound obtained in Reference Example 3 was suspended in ethanol and diethyl ether, and hydrogen chloride was bubbled thereto at 0° C. for 30 minutes. After further stirring at 0° C. for 15 hours, the insoluble matter was separated by filtration, and the filtrate was concentrated under reduced pressure to obtain ethyl tetrahydro-2H-thiopyran-4-*carboximidate 1,1-dioxide hydrochloride.

Reference Example 5

An ethanol suspension of the compound obtained in Reference Example 4 was added to a saturated ammonia/ethanol solution at 0° C., followed by stirring at room temperature for 13 hours. The insoluble matter was separated by filtration, and the filtrate was concentrated under reduced pressure to obtain tetrahydro-2H-thiopyran-4-carboximidamide 1,1-dioxide hydrochloride.

Reference Example 6

3,3,3-Trifluoropropanal was added to a mixture of sodium hydrogensulfate and water, with vigorously stirring at 0° C., followed by further stirring for 10 minutes. An aqueous solution of potassium cyanide was dropwise added, followed by reaction with stirring at 0° C. for 1 hour and then work-up and purification to obtain 4,4,4-trifluoro-2-hydroxybutanenitrile.

Reference Example 7

Iron powder was added to an acetic acid solution of benzyl 2-methyl-3-nitrobenzoate, followed by stirring at room temperature for 1.5 hours. The insoluble matter was separated by filtration, and the filtrate was concentrated under reduced pressure. This was diluted with ethyl acetate, neutralized with an aqueous saturated sodium hydrogencarbonate solution, and the insoluble matter was separated by filtration. The filtrate was extracted with ethyl acetate. The organic layer was washed with saturated brine, dried over anhydrous magnesium sulfate, and the solvent was evaporated under reduced pressure. Ethyl acetate was added and a solution of 4 M hydrogen chloride/ethyl acetate was dropwise added thereto at 0° C. The precipitate was collected by filtration to obtain benzyl 3-amino-2-methylbenzoate.

Reference Example 8

An aqueous solution (15 mL) of sodium nitrite (2.19 g) was dropwise added to an acetic acid (40 mL)/concentrated hydrochloric acid (12.5 mL) suspension of the compound obtained in Reference Example 7 at 0° C., followed by stirring for 30 minutes. To an acetic acid suspension of copper(II) chloride dihydrate, into which sulfur dioxide had been bubbled for 10 minutes, dropwise added was the reaction mixture previously prepared, at 0° C., followed by stirring at room temperature for 19 hours. The reaction mixture was poured into water with ice, followed by work-up and purification to obtain benzyl 3-(chlorosulfonyl)-2-methylbenzoate.

Reference Example 9

A trifluoroacetic acid solution of the compound obtained in Reference Example 8 was reacted with stirring under heat at 60° C. for 17 hour to obtain 3-(chlorosulfonyl)-2-methylbenzoic acid.

Reference Example 10

An aqueous 50% hydroxylamine solution was added to a methanol solution of 3-cyanobenzoic acid, followed by heating under reflux for 11 hours. The reaction liquid was concentrated, diluted with water, adjusted with 1 M hydrochloric acid to have a pH of from 2 to 3, and the precipitate was collected by filtration to obtain 3-[(hydroxyamino)(imino)methyl]benzoic acid. ES+: 181.

Reference Example 11

A mixture of the compound obtained in Reference Example 10, p-toluenesulfonic acid and triethoxymethane was heated under reflux for 30 minutes. After cooling, this was diluted with acetonitrile, and the insoluble matter was collected by filtration to obtain 3-(1,2,4-oxadiazol-3-yl)benzoic acid. FA: 191.

Reference Example 71

At room temperature, 3-(chlorosulfonyl)-4-fluorobenzoyl chloride (3.19 g) was added to a dioxane (75 mL) suspension of 2-(1,3-dihydro-2H-benzimidazol-2-ylidene)-1-(3-fluorophenyl)ethanone (1.50 g), followed by heating up to 110° C. and stirring for 1 hour. The reaction mixture was cooled to room temperature, the insoluble matter was separated by filtration, and then this was evaporated under reduced pressure. The residue was purified by silica gel column chromatography (hexane/ethyl acetate=3/1) to obtain 5-[2-(1,3-dihydro-2H-benzimidazol-2-ylidene)-3-(3-fluorophenyl)-3-oxopropanoyl]-2-fluorobenzenesulfonyl chloride (2.10 g).

Reference Example 207

1.58 M n-butyllithium/hexane solution (13.8 mL) was dropwise added to an anhydrous THF (30 mL) solution of diisopropylamine (3.08 mL) cooled to −78° C. under Ar gas atmosphere, thereby preparing a LDA solution. This solution was warmed up to −20° C., and then again cooled to −78° C., and thereafter 3-fluoroacetophenone (2.07 g) was dropwise added thereto, followed by stirring at −78° C. for 30 minutes. Then, 3-(chlorosulfonyl)benzoyl chloride (2.44 g) was dropwise added, followed by stirring for 15 minutes. Separately, 2-hydroxy-2-methylpropanimidamide hydrochloride (3.05 g) was added to a THF (40 mL) solution of sodium hydride (60% purity, 0.88 g) at room temperature, followed by stirring for 30 minutes and cooling to 0° C. Then, the previous solution was added thereto all at once, followed by stirring at room temperature for 1 hour. An aqueous saturated ammonium chloride solution was added, followed by extraction with ethyl acetate. The organic layer was washed with water, dried, and evaporated under reduced pressure. The residue was purified by silica gel column chromatography (chloroform/methanol=50/1) to obtain N-({3-[3-(3-fluorophenyl)-3-oxopropanoyl]phenyl}sulfonyl)-2-hydroxy-2-methylpropanimidamide (2.17 g).

Reference Example 208

Potassium fluoride (3.30 g) was added to a DMF (20 mL) solution of N-({3-[3-(3-fluorophenyl)-3-oxopropanoyl]phenyl}sulfonyl)-2-hydroxy-2-methylpropanimidamide (1.13 g), followed by cooling to 0° C. Then, carbon disulfide (1.06 g) was dropwise added thereto. Then, a DMF (4 mL) solution containing methyl iodide (0.95 g) was dropwise added, warmed up to room temperature, followed by stirring for 15 minutes. Water was added, followed by extraction with ethyl acetate. The organic layer was washed with water, dried, and evaporated under reduced pressure. The residue was purified by silica gel column chromatography (hexane/ethyl acetate=1/2) to obtain N-({3-[2-(3-fluorobenzoyl)-3,3-bis(methylthio)acryloyl]phenyl}sulfonyl)-2-hydroxy-2-methylpropanimidamide (1.32 g).

Reference Example 209

At room temperature, benzyl bromide (8.85 mL) and potassium carbonate (10.3 g) were added to a DMF (150 mL) solution of 2-methoxy-3-nitrobenzoic acid (9.80 g), followed by stirring for 70 minutes. The insoluble matter was separated by filtration, followed by evaporation under reduced pressure. This was subjected to liquid-liquid separation with ethyl acetate, aqueous sodium hydrogencarbonate solution, and hexane added thereto. The organic layer was washed with water and saturated brine in that order, dried, and then evaporated under reduced pressure to obtain benzyl 2-methoxy-3-nitrobenzoate (14.3 g).

N2: 3.92 (3H, s), 5.39 (2H, s), 7.23-7.47 (6H, m), 7.90 (1H, dd, J=8 Hz, 2 Hz), 8.05 (1H, dd, J=8 Hz, 2 Hz).

Iron (13.9 g) was added to an acetic acid (150 mL) solution of benzyl 2-methoxy-3-nitrobenzoate (14.3 g), followed by stirring at room temperature for 17.5 hours. The insoluble matter was separated by filtration, followed by evaporation under reduced pressure. An aqueous sodium hydrogencarbonate solution, ethyl acetate and Celite were added, the insoluble matter was separated by filtration, and then this was subjected to liquid-liquid separation to collect the organic layer. At room temperature, 4 N hydrogen chloride/ethyl acetate solution (12.5 mL) was added, followed by stirring for 30 minutes and then evaporation under reduced pressure. This was azeotroped with toluene to obtain benzyl 3-amino-2-methoxybenzoate hydrochloride (14.4 g). FA: 258.

An aqueous solution (20 mL) of sodium nitrite (3.55 g) was dropwise added to an acetic acid (110 mL)/hydrochloric acid (35 mL) suspension of benzyl 3-amino-2-methoxybenzoate hydrochloride (14.4 g), with its inner temperature kept at 0° C., followed by stirring for 30 minutes. Separately, sulfur dioxide gas was bubbled into acetic acid (125 mL) at 0° C., and then copper(II) chloride dihydrate (2.09 g) was added to prepare a solution. The above diazonium salt suspension was added to this solution, followed by stirring at 0° C. for 35 minutes and at room temperature for 17 hours. This was poured into water with ice, then subjected to liquid-liquid separation with ethyl acetate/hexane (1/1) added thereto. The organic layer was washed with water and saturated brine, and then evaporated under reduced pressure. The residue was purified by silica gel column chromatography (hexane/ethyl acetate=4/1) to obtain benzyl 3-(chlorosulfonyl)-2-methoxybenzoate (12.9 g).

N1: 3.77 (3H, s), 5.34 (2H, s), 7.15 (1H, t, J=8 Hz), 7.35-7.50 (5H, m), 7.68 (1H, dd, J=8 Hz, 2 Hz), 7.93 (1H, dd, J=8 Hz, 2 Hz).

A trifluoroacetic acid (95 mL) solution of benzyl 3-(chlorosulfonyl)-2-methoxybenzoate (12.9 g) was stirred at 70° C. for 5 hours. The solution part was decanted and evaporated under reduced pressure. Toluene was added to the residue, and this was again evaporated. The resulting solid was collected by filtration, washed with toluene and dried to obtain 3-(chlorosulfonyl)-2-methoxybenzoic acid (6.52 g).

N1: 3.84 (3H, s), 7.13 (1H, t, J=8 Hz), 7.67 (1H, dd, J=8 Hz, 2 Hz), 7.91 (1H, dd, J=8 Hz, 2 Hz), 13.86 (1H, brs).

Three drops of N,N-dimethylformamide were added to a thionyl chloride (4.37 mL) suspension of 3-(chlorosulfonyl)-2-methoxybenzoic acid (3.00 g), followed by stirring at 60° C. for 2 hours. The solvent was evaporated, and this was azeotroped with toluene to obtain 3-(chlorosulfonyl)-2-methoxybenzoyl chloride (3.22 g).

Reference Example 210

At 10° C., cesium carbonate (5.81 g) was added to a DMF (30 mL) solution of 3-fluoro-5-nitrobenzoic acid (2.20 g), followed by stirring for 30 minutes. Then, benzyl bromide (2.07 g) was dropwise added with taking 30 minutes, and then followed by further stirring for 10 minutes. The insoluble matter was separated by filtration, followed by evaporation under reduced pressure. This was subjected to liquid-liquid separation with ether and water added thereto, and the organic layer was dried and then evaporated to obtain benzyl 3-fluoro-5-nitrobenzoate (3.11 g). EI: 275.

Iron (3.16 g) was added to an acetic acid (31 mL) solution of benzyl 3-fluoro-5-nitrobenzoate (3.11 g), followed by stirring at room temperature for 1 hour. (This reaction was exothermic and its temperature reached 40° C.) The insoluble matter was separated by filtration, followed by evaporation under reduced pressure. An aqueous sodium hydrogencarbonate solution, ethyl acetate and Celite were added, and the insoluble matter was separated by filtration. Then this was subjected to liquid-liquid-separation, and the organic layer was collected. At room temperature, a 4 N hydrogen choloride/ethyl acetate solution (4 mL) was added, followed by stirring for 30 minutes. Then, the resulting solid was collected by filtration to obtain benzyl 3-amino-5-fluorobenzoate hydrochloride (2.18 g). FA: 246.

An aqueous sodium nitrite (561 mg) solution was dropwise added to an acetic acid (17 mL)/concentrated hydrochloric acid (0.65 mL) suspension of benzyl 3-amino-5-fluorobenzoate hydrochloride (2.18 g), with its inner temperature being kept at 5 to 110° C., followed by stirring for 1 hour. Separately, sulfur dioxide gas was bubbled into acetic acid (100 mL) at 0° C., and then copper (II) chloride dihydrate (330 mg) was added to prepare a solution. The above diazonium salt suspension was added to this solution all at once, followed by stirring at 0° C. for 1 hour and at room temperature for 14 hours. This was poured into water with ice, then subjected to liquid-liquid separation with ethyl acetate added thereto. The organic layer was washed with water and saturated brine, and then evaporated under reduced pressure. The residue was purified by silica gel column chromatography (hexane/ethyl acetate=6/1) to obtain benzyl 3-(chlorosulfonyl)-5-fluorobenzoate (2.30 g).

N1: 5.37 (2H, s), 7.36-7.50 (5H, m), 7.58 (1H, m), 7.68 (1H, m), 8.03 (1H, m).

A trifluoroacetic acid (18 mL) solution of benzyl 3-(chlorosulfonyl)-5-fluorobenzoate (2.30 g) was stirred at 60° C. for 18 hours. The oily substance floating on the liquid surface was removed, and the solution part was decanted and evaporated under reduced pressure. Hexane was added to the residue, then this was sonicated for 10 minutes. The resulting solid was collected by filtration to obtain 3-(chlorosulfonyl)-5-fluorobenzoic acid (1.37 g). EI: 238

One drop of N,N-dimethylformamide was added to a thionyl chloride (2.03 g) suspension of 3-(chlorosulfonyl)-5-fluorobenzoic acid (1.36 g), followed by stirring at 75° C. for 1 hour. The solvent was evaporated, and this was azeotroped with toluene to obtain 3-(chlorosulfonyl)-5-fluorobenzoyl chloride (1.47 g).

Reference Example 211

Benzyl N,N'-dicyclohexylimidocarbamate (0.82 g) was added to a DMF (3 mL) solution of 2-amino-3-nitrobenzoic acid (0.36 g), followed by heating up to 70° C. and stirring for 2 hours. The reaction mixture was cooled to room temperature, then an ethyl acetate/ether (1/1) solution was poured into it, and the insoluble matter was separated by filtration. The filtrate was washed with aqueous sodium hydrogencarbonate solution and water in that order, and the solvent was evaporated under reduced pressure. The residue was purified by silica gel column chromatography (hexane/ethyl acetate=3/1) to obtain benzyl 2-amino-3-nitrobenzoate (0.42 g). FA: 273.

Iron powder (0.78 g) and ammonium chloride (0.15 g) were added in that order to an ethanol/water (4/1) solution (40 mL) of benzyl 2-amino-3-nitrobenzoate (0.38 g), and this was heated under reflux for 20 minutes with vigorous stirring. The insoluble matter was separated by filtration while hot, and the filtrate was evaporated under reduced pressure to about ⅕, and then aqueous sodium hydrogencarbonate solution was added, followed by extraction with ethyl acetate. The organic layer was washed with water, dried, and evaporated under reduced pressure to obtain benzyl 2,3-diaminobenzoate (0.33 g).

In the same manner as in Reference Examples 1 to 11, 71 and 207 to 211, compounds of other Reference Examples shown in Tables 3 to 18 below were produced, using the corresponding starting materials. The structure, the production method and the physicochemical data of the compounds of Reference Examples are shown in the Tables.

Example 1

60% Sodium hydride (809 mg) was added to a DMF (30 mL) solution of formamidine hydrochloride (1.92 g), followed by stirring at room temperature for 15 minutes. A DMF (10 mL) solution of 3-[3-(3,5-difluorophenyl)-2-(1,3-dihydro-2H-benzimidazol-2-ylidene)-3-oxopropanoyl]benzenesulfonyl chloride (hereinafter referred to as starting compound A, 1.13 g) was added, followed by stirring at room temperature for 1.5 hours. The reaction mixture was poured into an excess amount of aqueous ammonium chloride solution, followed by extraction with ethyl acetate. The organic layer was washed with water, concentrated under reduced pressure, purified by silica gel column chromatography (chloroform/methanol=10/1), and crystallized from diethyl ether/n-hexane to obtain 3-[3-(3,5-difluorophenyl)-2-(1,3-dihydro-2H-benzimidazol-2-ylidene)-3-oxopropanoyl]-N-(iminomethyl)benzenesulfonamide (81 mg).

Example 2

A DMF (3 mL) solution of the starting compound A (300 mg) was added to a DMF (10 mL) solution of glycine ethyl ester hydrochloride (733 mg) and triethylamine (0.73 mL), followed by stirring at room temperature for 30 minutes. This was diluted with water, the precipitate was collected by filtration, and dried under reduced pressure to obtain ethyl [({3-[3-(3,5-difluorophenyl)-2-(1,3-dihydro-2H-benzimidazol-2-ylidene)-3-oxopropanoyl]phenyl}sulfonyl)amino]acetate (505 mg).

Example 3

Aminoacetonitrile (177 mg) was added to a DMF (10 mL) solution of the starting compound A (300 mg) at 0° C., followed by stirring at room temperature for 1.5 hours. An excess amount of an aqueous saturated ammonium chloride solution was added, and the precipitate was collected by filtration, and dried under reduced pressure to obtain N-(cyanomethyl)-3-[3-(3,5-difluorophenyl)-2-(1,3-dihydro-2H-benzimidazol-2-ylidene)-3-oxopropanoyl]benzenesulfonamide (242 mg).

Example 4

2-Aminopyridine (248 mg) was added to a pyridine (10 mL) solution of the starting compound A (250 mg), followed by stirring at room temperature for 1 hour, and then the reaction mixture was concentrated under reduced pressure. The resulting residue was purified by silica gel column chromatography (n-hexane/ethyl acetate=1/2), and then recrystallized from ethyl acetate/n-hexane to obtain 3-[3-(3,5-difluorophenyl)-2-(1,3-dihydro-2H-benzimidazol-2-ylidene)-3-oxopropanoyl]-N-pyridin-2-ylbenzenesulfonamide (36 mg).

Example 5

A mixture of 3-[3-(3,5-difluorophenyl)-2-(1,3-dihydro-2H-benzimidazol-2-ylidene)-3-oxopropanoyl]benzenesulfonamide (hereinafter referred to as starting compound B, 500 mg), acetic anhydride (5 mL), pyridine (10 mL) and DMF (20 mL) was heated with stirring at 55° C. for 2 hours. The reaction mixture was concentrated under reduced pressure, diluted with ethyl acetate and washed with aqueous saturated sodium hydrogencarbonate solution and water successively. The solvent was evaporated under reduced pressure. The resulting residue was purified by silica gel column chromatography (chloroform/methanol=10/1), and recrystallized from ethyl acetate/n-hexane to obtain N-({3-[3-(3,5-difluorophenyl)-2-(1,3-dihydro-2H-benzimidazol-2-ylidene)-3-oxopropanoyl]phenyl}sulfonyl)acetamide (58 mg).

Example 6

60% Sodium hydride (21 mg) was added to a 1-methyl-2-pyrrolidone (6 mL) solution of the starting compound B (240 mg) and isopropyl isocyanate (0.4 mL), followed by stirring at room temperature for 1.5 hours. This was diluted with 1 M hydrochloric acid, followed by extraction with ethyl acetate. The organic layer was washed with water, and the solvent was evaporated under reduced pressure. The residue was purified by silica gel column chromatography (n-hexane/ethyl acetate=1/1), and recrystallized from ethyl acetate/n-hexane to obtain 3-[3-(3,5-difluorophenyl)-2-(1,3-dihydro-2H-benzimidazol-2-ylidene)-3-oxopropanoyl]-N-[(isopropylamino)carbonyl]benzenesulfonamide (14 mg).

Example 7

A mixture of the starting compound B (797 mg), potassium cyanate (994 mg), acetic acid (10 mL), water (25 mL) and N-methylpyrrolidinone (30 mL) was heated with stirring at 100° C. for 31 hours. After cooling to room temperature, water was added. The insoluble matter was collected by filtration, purified by silica gel column chromatography (chloroform/methanol=10/1), and further washed with diethyl ether to obtain N-(aminocarbonyl)-3-[3-(3,5-difluorophenyl)-2-(1,3-dihydro-2H-benzimidazol-2-ylidene)-3-oxopropanoyl]benzenesulfonamide (15 mg).

Example 8

An aqueous 1 M sodium hydroxide solution (3.1 mL) was added to a THF (10 mL) solution of the compound (300 mg) obtained in Example 2, followed by stirring at room temperature for 3.5 hours. THF was evaporated under reduced pressure, and 1 M hydrochloric acid was excessively added. The precipitate was collected by filtration and dried under reduced pressure to obtain [({3-[3-(3,5-difluorophenyl)-2-(1,3-dihydro-2H-benzimidazol-2-ylidene)-3-oxopropanoyl]phenyl}sulfonyl)amino]acetic acid (250 mg).

Example 9

Dimethylamine hydrochloride (31 mg), triethylamine (0.05 mL), HOBt (51 mg) and WSC.HCl (73 mg) were added to a DMF (5 mL) solution of [({3-[3-(3,5-difluorophenyl)-2-(1,3-dihydro-2H-benzimidazol-2-ylidene)-3-oxopropanoyl]phenyl}sulfonyl)amino](imino)acetic acid (40 mg), followed by stirring at room temperature for 1.5 hours. Water was added to the reaction mixture, followed by extraction with ethyl acetate. The organic layer was washed with saturated brine, dried over anhydrous magnesium sulfate, and concentrated under reduced pressure. The residue was recrystallized from ethyl acetate/n-hexane to obtain 2-[({3-[3-(3,5-difluorophenyl)-2-(1,3-dihydro-2H-benzimidazol-2-ylidene)-3-oxopropanoyl]phenyl}sulfonyl)amino]-2-imino-N,N-dimethylacetamide (28 mg).

Example 10

At 0° C., benzyl piperazine-1-carboxylate (1.37 g) was added to an acetonitrile (5 mL) solution of N-({3-[3-(3,5-difluorophenyl)-2-(1,3-dihydro-2H-benzimidazol-2-ylidene)-3-oxopropanoyl]phenyl}sulfonyl)-3,5-dimethyl-1H-pyrazole-1-carboximidamide (205 mg), and heated under reflux for 3 days. After cooling, ethyl acetate was added, then washed with aqueous saturated ammonium chloride solution, water and saturated brine in that order, and dried over anhydrous magnesium sulfate. The solvent was evaporated under reduced pressure, and the resulting residue was purified by silica gel column chromatography (n-hexane/ethyl acetate=1/4) to obtain benzyl 4-[[({3-[3-(3,5-difluorophenyl)-2-(1,3-dihydro-2H-benzimidazol-2-ylidene)-3-oxopropanoyl]phenyl}sulfonyl)amino](imino)methyl]piperazine-1-carboxylate (76 mg).

Example 11

10% Pd—C (210 mg) was added to an ethanol (20 mL) solution of the compound (205 mg) obtained in Example 10, followed by stirring at room temperature for 19 hours under hydrogen atmosphere (1 atom). The insoluble matter was separated by filtration, and the filtrate was concentrated under reduced pressure. The residue was purified by silica gel column chromatography (chloroform/methanol=50/1), and recrystallized from ethyl acetate/n-hexane to obtain N-({3-[3-(3,5-difluorophenyl)-2-(1,3-dihydro-2H-benzimidazol-2-ylidene)-3-oxopropanoyl]phenyl}sulfonyl)piperazine-1-carboximidamide (46 mg).

Example 12

Dess-Martin reagent (15 wt. % dichloromethane solution, 0.73 mL) was added to a dichloromethane (2 mL) solution of N-({3-[3-(3,5-difluorophenyl)-2-(1,3-dihydro-2H-benzimidazol-2-ylidene)-3-oxopropanoyl]phenyl}sulfonyl)-2-hydroxypropanimidamide (90 mg), followed by stirring at room temperature for 4 hours. Ethyl acetate was added to the reaction mixture, washed with water, dried over anhydrous magnesium sulfate, and the organic layer was concentrated under reduced pressure. The resulting residue was purified by silica gel column chromatography (n-hexane/ethyl acetate=2/1), and recrystallized from ethyl acetate/n-hexane to obtain N-({3-[3-(3,5-difluorophenyl)-2-(1,3-dihydro-2H-benzimidazol-2-ylidene)-3-oxopropanoyl]phenyl}sulfonyl)-2-oxopropanimidamide (57 mg).

Example 13

2 M dimethylamine/THF solution (0.85 mL) was added to a DMF (5 mL) solution of 2-chloro-N-({3-[3-(3,5-difluorophenyl)-2-(1,3-dihydro-2H-benzimidazol-2-ylidene)-3-oxopropanoyl]phenyl}sulfonyl)ethanimidamide (181 mg), followed by stirring at room temperature for 1 hour. Water was added to the reaction mixture, followed by extraction with ethyl acetate. The organic layer was washed with saturated brine, concentrated under reduced pressure, and the residue was purified by silica gel column chromatography (chloroform/methanol=50/1), and recrystallized from ethyl acetate/n-hexane to obtain N-({3-[3-(3,5-difluorophenyl)-2-

(1,3-dihydro-2H-benzimidazol-2-ylidene)-3-oxopropanoyl] phenyl}sulfonyl)-2-(dimethylamino)ethanimidamide (76 mg).

Example 14

3-[(dimethylamino)sulfonyl]benzoyl chloride (1.97 g) was added to a mixture of 1-(3,5-difluorophenyl)-2-(1,3-dihydro-2H-benzimidazol-2-ylidene)ethanone (865 mg), triethylamine (1.6 mL) and 2-methoxyethyl ether (10 mL), followed by heating with stirring at 110° C. for 30 minutes. Water (0.06 mL) was added, followed by further heating under reflux for 30 minutes. After cooling, water was added, followed by extraction with ethyl acetate. The organic layer was washed with water, concentrated under reduced pressure, and the residue was purified by silica gel column chromatography (n-hexane/ethyl acetate=1/1), and recrystallized from ethyl acetate/n-hexane to obtain 3-[3-(3,5-difluorophenyl)-2-(1,3-dihydro-2H-benzimidazol-2-ylidene)-3-oxopropanoyl]-N,N-dimethylbenzenesulfonamide (391 mg).

Example 15

The starting compound B (500 mg) was added to a DMF (20 mL) suspension of 60% sodium hydride, followed by stirring at room temperature. N,N-dimethylacetamide dimethyl acetal (0.48 mL) was added, followed by further stirring at room temperature for 15 hours. An aqueous saturated ammonium chloride solution was added to the reaction mixture, and the resulting precipitate was collected by filtration to obtain (1E)-N'-({3-[3-(3,5-difluorophenyl)-2-(1,3-dihydro-2H-benzimidazol-2-ylidene)-3-oxopropanoyl] phenyl}sulfonyl)-N,N-dimethylethanimidamide (267 mg).

Example 16

Acetic anhydride (90 mg) was added to a pyridine (5 mL) solution of N-({3-[3-(3,5-difluorophenyl)-2-(1,3-dihydro-2H-benzimidazol-2-ylidene)-3-oxopropanoyl] phenyl}sulfonyl)-2-hydroxyethanimidamide (225 mg), followed by stirring at room temperature for 2 hours. An excess amount of an aqueous saturated ammonium chloride solution was added, followed by extraction with ethyl acetate. The organic layer was washed with water, concentrated under reduced pressure, and the residue was purified by silica gel column chromatography (chloroform/methanol=80/1) and crystallized from ethyl acetate/n-hexane to obtain 2-[({3-[3-(3,5-difluorophenyl)-2-(1,3-dihydro-2H-benzimidazol-2-ylidene)-3-oxopropanoyl]phenyl}sulfonyl)amino]-2-iminoethylacetic acid (150 mg).

Example 17

10% Pd—C (85 mg) was added to an ethyl acetate (150 mL) suspension of N-({3-[3-(3,5-difluorophenyl)-2-(5-nitro-1,3-dihydro-2H-benzimidazol-2-ylidene)-3-oxopropanoyl] phenyl}sulfonyl)ethanimidamide (845 mg), followed by stirring at room temperature for 22 hours under hydrogen atmosphere (1 atm). The insoluble matter was separated by filtration, washed with ethanol, and the filtrate was concentrated under reduced pressure. The residue was purified by silica gel column chromatography (chloroform/methanol=30/1), and recrystallized from ethyl acetate/n-hexane to obtain N-({3-[2-(5-amino-1,3-dihydro-2H-benzimidazol-2-ylidene)-3-(3,5-difluorophenyl)-3-oxopropanoyl] phenyl}sulfonyl)ethanimidamide (667 mg).

Example 18

At −20° C., 77% m-chloroperbenzoic acid (132 mg) was added to a dichloromethane (10 mL) suspension of N-[(3-{2-(1,3-dihydro-2H-benzimidazol-2-ylidene)-3-[3-(methylsulfanyl)phenyl]-3-oxopropanoyl}phenyl)sulfonyl]ethanimidamide (100 mg), followed by stirring for 3 hours. An excess amount of an aqueous saturated ammonium chloride solution was added, followed by extraction with ethyl acetate. The organic layer was washed with water, concentrated under reduced pressure, and the residue was purified by silica gel column chromatography (chloroform/methanol=60/1) and crystallized from ethyl acetate/n-hexane to obtain N-[(3-{2-(1,3-dihydro-2H-benzimidazol-2-ylidene)-3-[3-(methanesulfonyl)phenyl]-3-oxopropanoyl}phenyl)sulfonyl]ethanimidamide (64 mg).

Example 19

Ammonium formate (260 mg) and 10% Pd—C (250 mg) were added to a DMF (25 mL) solution of N-({3-[3-(2-chloropyridin-4-yl)-2-(1,3-dihydro-2H-benzimidazol-2-ylidene)-3-oxopropanoyl]phenyl})ethanimidamide (500 mg), followed by stirring at room temperature for 3 hours. The insoluble matter was separated by filtration, the filtrate was concentrated under reduced pressure, and the residue was washed with ethyl acetate to obtain N-({3-[2-(1,3-dihydro-2H-benzimidazol-2-ylidene)-3-oxo-3-pyridin-4-ylpropanoyl]phenyl}sulfonyl)ethanimidamide (372 mg).

Example 532

1,2-Phenylenediamine (81 mg) was added to an EtOH (20 mL) solution of N-[(3-{2-[(2,4-dimethyl-1,3-thiazol-5-yl) carbonyl]-3,3-bis(methylthio)acryloyl}phenyl)sulfonyl]-2-hydroxy-2-methylpropanimidamide (370 mg), followed by heating under reflux for 13 hours. After cooling, the reaction mixture was concentrated under reduced pressure. The resulting residue was purified by silica gel column chromatography (chloroform/methanol=50/1), and recrystallized from ethyl acetate/n-hexane to obtain N-({3-[2-(1,3-dihydro-2H-benzimidazol-2-ylidene)-3-(2,4-dimethyl-1,3-thiazol-5-yl)-3-oxopropanoyl]phenyl}sulfonyl)-2-hydroxy-2-methylpropanimidamide (310 mg).

Example 533

Under ice cooling, 4 N—HCl/ethyl acetate (0.09 mL) was added to an EtOH/dioxane (2/1) mixed solution (4 mL) of N-({3-[2-(1,3-dihydro-2H-benzimidazol-2-ylidene)-3-(2-methoxypyridin-4-yl)-3-oxopropanoyl]phenyl}sulfonyl)-2-hydroxy-2-methylpropanimidamide (127 mg), followed by stirring for 1 hour. The reaction mixture was concentrated under reduced pressure. An aqueous sodium hydrogencarbonate solution was added to the resulting residue, followed by extraction with ethyl acetate and concentration under reduced pressure. The resulting residue was purified by silica gel column chromatography (chloroform/methanol=10/1) to obtain N-({3-[2-(1,3-dihydro-2H-benzimidazol-2-ylidene)-3-oxo-3-(2-oxo-1,2-dihydropyridin-4-yl)propanoyl] phenyl}sulfonyl)-2-hydroxy-2-methylpropanimidamide (18 mg).

Example 696

At room temperature, sodium hydride (579 mg) was added to a THF (70 mL) suspension of (2R)-2-hydroxypropanimidamide hydrochloride (1.65 g), followed by heating up to 60° C. and stirring for 30 minutes. The reaction mixture was cooled to room temperature, and a THF (35 mL) solution of 5-[2-(1,3-dihydro-2H-benzimidazol-2-ylidene)-3-(3-fluorophenyl)-3-oxopropanoyl]-2-fluorobenzenesulfonyl chloride (2.10 g) was added, followed by stirring for 20 minutes. Then, this was subjected to liquid-liquid separation with water and ethyl acetate added thereto, the organic layer was washed with saturated brine, and the solvent was evaporated under reduced pressure. The residue was purified by silica gel column chromatography (chloroform/methanol=50/1) to obtain (2R)-N-({5-[2-(1,3-dihydro-2H-benzimidazol-2-ylidene)-3-(3-fluorophenyl)-3-oxopropanoyl]-2-fluorophenyl}sulfonyl)-2-hydroxypropanimidamide (1.95 g).

In the same manner as in Examples 1 to 19, 532, 533 and 696, compounds of other Examples shown in Tables 19 to 57 below were synthesized, using the corresponding starting materials. The structure, the production method and the physicochemical data of the compounds of those Examples are shown in the Tables.

Tables 58 to 70 show the structures of other compounds of the present invention. These can be readily synthesized according to the above-mentioned production methods, the methods described in Examples and methods obvious to persons skilled in the art, or modified methods thereof. In Tables 58 to 70, the following abbreviations are used for the group $R^3$:

C2: $-NH(CH_2)_2OH$, C3: $-NH(CH_2)_3OH$, GN: $-N=C(NH_2)_2$,

[Formula 15]

RM: 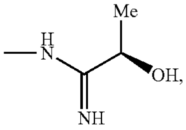 SM: 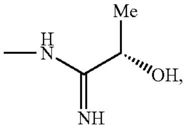

DM: 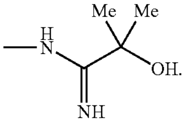

TABLE 3

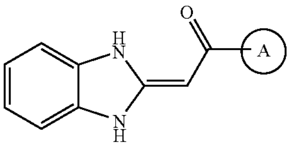

| REx | Syn | A | Dat |
|---|---|---|---|
| 1 | R1 | 3-F-Ph | FA: 255 |
| 12 | R1 | 2-F-Ph | FA: 255 |
| 13 | R1 | 4-F-Ph | ES+: 255 |
| 14 | R1 | 2-Cl-Ph | ES+: 271 |
| 15 | R1 | 3-Cl-Ph | ES+: 271 |
| 16 | R1 | 2-OMe-Ph | ES+: 267 |
| 17 | R1 | 3-OMe-Ph | ES−: 265 |
| 18 | R1 | 3-OH-Ph | ES+: 253 |
| 19 | R1 | 3-OEt-Ph | ES+: 281 |
| 20 | R1 | 3-OiPr-Ph | ES+: 295 |
| 21 | R1 | 3-OPr-Ph | ES+: 295 |
| 22 | R1 | 3-OPh-Ph | ES+: 329 |
| 23 | R1 | 2-Me-Ph | ES+: 251 |
| 24 | R1 | 3-Me-Ph | ES+: 251 |

TABLE 3-continued

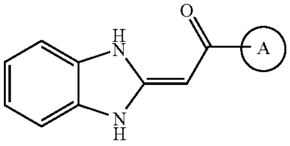

| REx | Syn | A | Dat |
|---|---|---|---|
| 25 | R1 | 4-Me-Ph | ES+: 251 |
| 26 | R1 | 3-CN-Ph | ES+: 262 |
| 27 | R1 | 2-$CF_3$-Ph | FA: 305 |
| 28 | R1 | 3-$CF_3$-Ph | ES+: 305 |
| 29 | R1 | 4-$CF_3$-Ph | FA: 305 |
| 30 | R1 | 2,3-diF-Ph | FA: 273 |
| 31 | R1 | 3,4-diF-Ph | FA: 273 |
| 32 | R1 | 2,5-diF-Ph | ES+: 273 |
| 33 | R1 | 3-Cl-4-F-Ph | ES+: 289 |
| 34 | R1 | 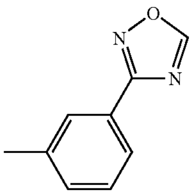 | ES+: 305 |
| 35 | R1 | 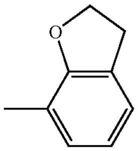 | ES+: 279 |
| 36 | R1 | 3,4-diCl-Ph | ES−: 303 |
| 37 | R1 | 3,5-diCl-Ph | FA: 305 |
| 38 | R1 | 2,3-diCl-Ph | ES−: 303 |
| 39 | R1 | 2,5-diCl-Ph | ES−: 303 |
| 40 | R1 | 3,5-diMe-Ph | ES+: 265 |
| 41 | R1 | 2,3-diMe-Ph | ES+: 265 |
| 42 | R1 | 3,4-diMe-Ph | FA: 265 |
| 43 | R1 | 2-Me-3-F-Ph | ES+: 269 |
| 44 | R1 | 2-Me-5-F-Ph | ES+: 269 |
| 45 | R1 | 3-F-4-OMe-Ph | FA: 285 |
| 46 | R1 | 2-OMe-5-Cl-Ph | FA: 301 |
| 47 | R1 | 3-Cl-4-OMe-Ph | FA: 301 |
| 48 | R1 | 3,4,5-triF-Ph | FA: 291 |
| 49 | R1 | 2-Cl-4,5-diF-Ph | FA: 307 |
| 50 | R1 | 2-Ph-Ph | ES+: 313 |
| 51 | R1 | 3-Ph-Ph | AP+: 313 |
| 52 | R1 | 2Naph | ES+: 287 |
| 53 | R1 | 1Naph | ES+: 287 |
| 54 | R1 | 4-F-1Naph | AP+: 305 |
| 55 | R1 | 6-Cl-3Py | ES+: 272 |
| 56 | R1 | 2-Cl-4Py | ES+: 272 |
| 57 | R1 | Pyra | ES+: 239 |
| 58 | R1 | 2Thi | ES+: 243 |
| 59 | R1 | 3Thi | ES+: 243 |
| 60 | R1 | 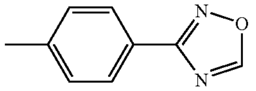 | ES+: 305 |
| 61 | R1 | 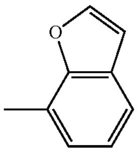 | ES+: 277 |

TABLE 4

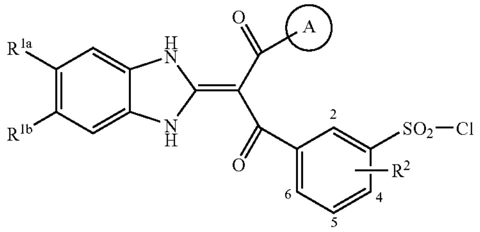

| REx | Syn | A | $R^{1a}$ | $R^{1b}$ | $R^2$ | Dat |
|---|---|---|---|---|---|---|
| 2 | R2 | 3,5-diF-Ph | H | H | H | ES+: 475 |
| 62 | R2 | Ph | H | H | H | ES+: 439 |
| 63 | R2 | Ph | H | H | 2-Me | Not Isolated |
| 64 | R2 | Ph | BnS | H | H | ES+: 561 |
| 65 | R2 | 2-F-Ph | H | H | H | ES+: 457 |
| 66 | R2 | 3-F-Ph | H | H | H | ES+: 457 |
| 67 | R2 | 3-F-Ph | H | H | 2-Me | FA: 471 |
| 68 | R2 | 3-F-Ph | H | H | 6-Me | FA: 471 |
| 69 | R2 | 3-F-Ph | H | H | 4-Me | FA: 471 |
| 70 | R2 | 3-F-Ph | H | H | 2-Cl | FA: 491 |
| 71 | R2 | 3-F-Ph | H | H | 4-F | FA: 475 |
| 72 | R2 | 3-F-Ph | H | H | 4-Cl | FA: 491 |
| 73 | R2 | 3-F-Ph | PhCO | H | H | ES+: 561 |
| 74 | R2 | 3-F-Ph | MeO | MeO | H | ES+: 517 |
| 75 | R2 | 4-F-Ph | H | H | H | Not Isolated |
| 76 | R2 | 2-Cl-Ph | H | H | H | ES+: 473 |
| 77 | R2 | 2-Cl-Ph | H | H | 2-Me | Not Isolated |
| 78 | R2 | 3-Cl-Ph | H | H | H | ES+: 473 |
| 79 | R2 | 3-Cl-Ph | H | H | 2-Me | Not Isolated |
| 80 | R2 | 3-Cl-Ph | H | H | 4-Me | Not Isolated |
| 81 | R2 | 4-Cl-Ph | H | H | H | ES+: 473 |
| 82 | R2 | 4-Cl-Ph | H | H | 2-Me | Not Isolated |
| 83 | R2 | 3-Br-Ph | H | H | H | ES+: 519 |
| 84 | R2 | 2-OMe-Ph | H | H | H | ES+: 469 |
| 85 | R2 | 3-OMe-Ph | H | H | H | Not Isolated |
| 86 | R2 | 4-OMe-Ph | H | H | H | ES+: 469 |
| 87 | R2 | 3-SMe-Ph | H | H | H | ES+: 485 |
| 88 | R2 | 3-Ac-Ph | H | H | H | ES+: 481 |

TABLE 5

| | | | | | | |
|---|---|---|---|---|---|---|
| 89 | R2 | 2-Me-Ph | H | H | H | Not Isolated |
| 90 | R2 | 3-Me-Ph | H | H | H | ES+: 453 |
| 91 | R2 | 3-Me-Ph | H | H | 2-Me | Not Isolated |

TABLE 5-continued

| | | | | | | |
|---|---|---|---|---|---|---|
| 92 | R2 | 3-Me-Ph | H | H | 6-Me | ES+: 467 |
| 93 | R2 | 3-Me-Ph | H | H | 4-Me | ES+: 467 |
| 94 | R2 | 3-Me-Ph | H | H | 2-Cl | FA: 487 |
| 95 | R2 | 4-Me-Ph | H | H | H | FA: 453 |
| 96 | R2 | 3-OH-Ph | H | H | H | ES+: 455 |
| 97 | R2 | 3-OEt-Ph | H | H | H | Not Isolated |
| 98 | R2 | 3-OPr-Ph | H | H | H | Not Isolated |
| 99 | R2 | 3-OiPr-Ph | H | H | H | Not Isolated |
| 100 | R2 | 3-OPh-Ph | H | H | H | ES+: 531 |
| 101 | R2 | 2-$CF_3$-Ph | H | H | H | Not Isolated |
| 102 | R2 | 3-$CF_3$-Ph | H | H | H | Not Isolated |
| 103 | R2 | 4-$CF_3$-Ph | H | H | H | Not Isolated |
| 104 | R2 | 3-CN-Ph | H | H | H | Not Isolated |
| 105 | R2 | 3,5-diF-Ph | H | H | 2-Me | FA: 489 |
| 106 | R2 | 3,5-diF-Ph | H | H | 4-Me | FN: 487 |
| 107 | R2 | 3,5-diF-Ph | H | H | 6-Me | ES+: 489 |
| 108 | R2 | 3,5-diF-Ph | H | H | 4-Me | ES+: 489 |
| 109 | R2 | 3,5-diF-Ph | H | H | 2-Cl | FA: 509 |
| 110 | R2 | 3,5-diF-Ph | H | H | 6-OMe | Not Isolated |
| 111 | R2 | 2,3-diF-Ph | H | H | H | Not Isolated |
| 112 | R2 | 2,3-diF-Ph | H | H | 2-Me | ES+: 489 |
| 113 | R2 | 3,4-diF-Ph | H | H | H | Not Isolated |
| 114 | R2 | 2,5-diF-Ph | H | H | H | FA: 475 |
| 115 | R2 | 2,5-diF-Ph | H | H | 2-Me | ES+: 489 |
| 116 | R2 | 2-Cl-3-F-Ph | H | H | H | FN: 489 |
| 117 | R2 | 3-Cl-4-F-Ph | H | H | H | ES+: 491 |
| 118 | R2 | 2-Cl-5-F-Ph | H | H | H | ES+: 491 |
| 119 | R2 | 3-Cl-5-F-Ph | H | H | H | ES+: 491 |
| 120 | R2 | 2-Cl-4,5-diF-Ph | H | H | H | FA: 509 |
| 121 | R2 | 3,4-diCl-Ph | H | H | H | Not Isolated |
| 122 | R2 | 3,5-diCl-Ph | H | H | H | Not Isolated |
| 123 | R2 | 2,3-diCl-Ph | H | H | H | Not Isolated |
| 124 | R2 | 2,5-diCl-Ph | H | H | H | Not Isolated |

TABLE 6

| | | | | | | |
|---|---|---|---|---|---|---|
| 125 | R2 | 2-Me-3-F-Ph | H | H | H | ES+: 471 |
| 126 | R2 | 2-Me-5-F-Ph | H | H | H | Not Isolated |
| 127 | R2 | 2-Me-5-F-Ph | H | H | 2-Me | N1: 2.10 (3H, s), 2.42 (3H, s), 6.62-6.86 (4H, m), 6.89-6.98 (1H, m), 7.26-7.38 (2H, m), 7.47 (1H, dd, J = 7.7 Hz, 1.5 Hz), 7.73-7.82 (2H, m), 13.32 (2H, s) |
| 128 | R2 | 3-F-4-Me-Ph | H | H | H | FN: 469 |
| 129 | R2 | 3,5-diMe-Ph | H | H | H | Not Isolated |
| 130 | R2 | 3,4-diMe-Ph | H | H | H | FA: 467 |
| 131 | R2 | 3,4-diMe-Ph | H | H | 2-Me | FA: 481 |
| 132 | R2 | 2,3-diMe-Ph | H | H | H | Not Isolated |
| 133 | R2 | 3-F-4-OMe-Ph | H | H | H | FA: 487 |
| 134 | R2 | 2-OMe-5-F-Ph | H | H | H | ES+: 487 |
| 135 | R2 | 2-OMe-5-Cl-Ph | H | H | H | FA: 503 |
| 136 | R2 | 3-Cl-4-OMe-Ph | H | H | H | FA: 503 |
| 137 | R2 | 2-Me-3-Cl-Ph | H | H | H | FA: 487 |
| 138 | R2 | 3,4,5-triF-Ph | H | H | H | FA: 491 |
| 139 | R2 | 3,4,5-triF-Ph | H | H | 2-Me | Not Isolated |
| 140 | R2 | 3,4,5-triF-Ph | H | H | 4-Me | Not Isolated |
| 141 | R2 | 2-Ph-Ph | H | H | H | Not Isolated |
| 142 | R2 | 3-Ph-Ph | H | H | H | ES+: 515 |

TABLE 6-continued

| | | | | | | |
|---|---|---|---|---|---|---|
| 143 | R2 | 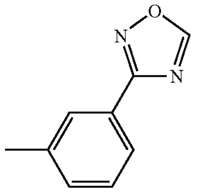 | H | H | H | Not Isolated |
| 144 | R2 | 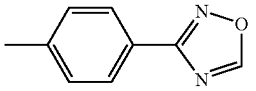 | H | H | H | ES+: 507 |
| 145 | R2 | 2Naph | H | H | H | Not Isolated |
| 146 | R2 | 2Naph | H | H | 2-Me | FA: 503 |
| 147 | R2 | 1Naph | H | H | H | Not Isolated |
| 148 | R2 | 1Naph | H | H | 2-Me | FA: 503 |
| 149 | R2 | 1Naph | H | H | 4-Me | Not Isolated |
| 150 | R2 | 4-F-1Naph | H | H | H | ES+: 507 |

TABLE 7

| | | | | | | |
|---|---|---|---|---|---|---|
| 151 | R2 | 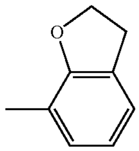 | H | H | H | ES+: 481 |
| 152 | R2 | 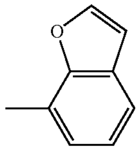 | H | H | H | Not Isolated |
| 153 | R2 | 6-Cl-3Py | H | H | H | Not Isolated |
| 154 | R2 | 6-Cl-3Py | H | H | 2-Me | Not Isolated |
| 155 | R2 | 6-Cl-3Py | H | H | 4-Me | Not Isolated |
| 156 | R2 | 5,6-diCl-3Py | H | H | H | Not Isolated |
| 157 | R2 | 2-Cl-4Py | H | H | H | ES+: 474 |
| 158 | R2 | Pyra | H | H | H | Not Isolated |
| 159 | R2 | 2Thi | H | H | H | ES+: 445 |
| 160 | R2 | 3Thi | H | H | H | Not Isolated |
| 161 | R2 | 3,5-diF-Ph | Me | Me | H | Not Isolated |
| 162 | R2 | 3,5-diF-Ph | F | F | H | Not Isolated |
| 163 | R2 | 3,5-diF-Ph | F | H | H | FA: 493 |
| 164 | R2 | 3,5-diF-Ph | Cl | H | H | Not Isolated |
| 165 | R2 | 3,5-diF-Ph | Me | H | H | Not Isolated |
| 166 | R2 | 3,5-diF-Ph | $O_2N$ | H | H | ES+: 520 |
| 167 | R2 | 3,5-diOMe-Ph | H | H | H | FA: 499 |

TABLE 8

| REx | Syn | Str | Dat |
|---|---|---|---|
| 3 | R3 | 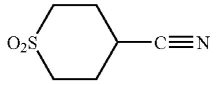 | ES+: 160 |
| 4 | R4 | 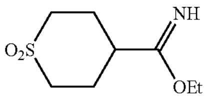 | Not Isolated Sal: HCl |
| 5 | R5 | 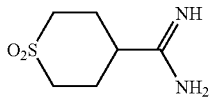 | ES+: 177 Sal: HCl |

TABLE 8-continued

| REx | Syn | Str | Dat |
|---|---|---|---|
| 6 | R6 | 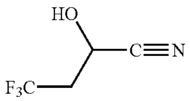 | ES+: 140 |
| 7 | R7 | 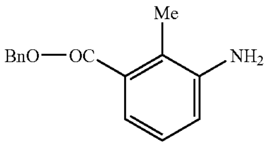 | FA: 242 Sal: HCl |
| 8 | R8 | 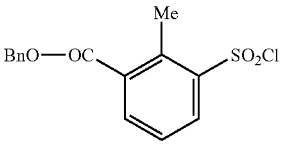 | EI: 324 |
| 9 | R9 | 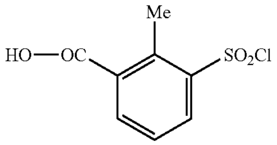 | FN: 233 |
| 168 | R9 | 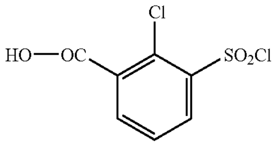 | FN: 253 |
| 169 | R7 | 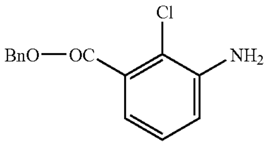 | FA: 261 Sal: HCl |

TABLE 8-continued

| REx | Syn | Str | Dat |
|---|---|---|---|
| 170 | 9 | 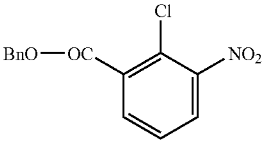 | Not Isolated |
| 171 | R5 | 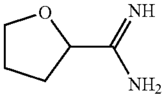 | FA: 115<br>Sal: HCl |
| 172 | R5 | 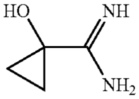 | FA: 101<br>Sal: HCl |
| 181 | R5 | 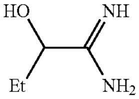 | FA: 103<br>Sal: HCl |
| 182 | R4 | 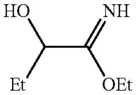 | FA: 132<br>Sal: HCl |
| 183 | R5 | 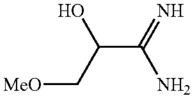 | FA: 119<br>Sal: HCl |
| 184 | R4 | 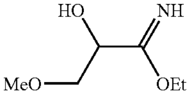 | FA: 148<br>Sal: HCl |
| 185 | R5 | 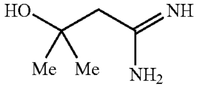 | FA: 117<br>Sal: HCl |
| 186 | R4 | 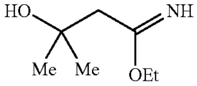 | FA: 146<br>Sal: HCl |
| 187 | R5 | 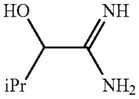 | FA: 117<br>Sal: HCl |
| 188 | R4 | 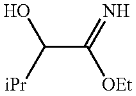 | FA: 146<br>Sal: HCl |
| 189 | R5 | 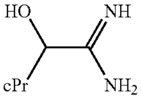 | FA: 115<br>Sal: HCl |
| 190 | R4 | 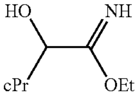 | FA: 144<br>Sal: HCl |
| 191 | R5 | 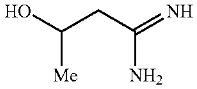 | FA: 103<br>Sal: HCl |
| 192 | R4 | 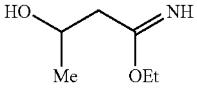 | FA: 132<br>Sal: HCl |

TABLE 9

| | | | | | | | |
|---|---|---|---|---|---|---|---|
| 173 | R4 | 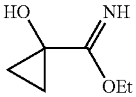 | FA: 130<br>Sal: HCl | 193 | R5 | 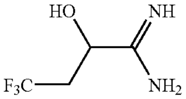 | FA: 157<br>Sal: HCl |
| 174 | R5 | 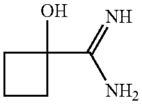 | FA: 115<br>Sal: HCl | 194 | R4 | 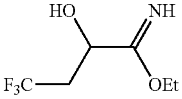 | FA: 186<br>Sal: HCl |
| 175 | R4 | 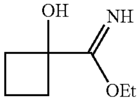 | FA: 144<br>Sal: HCl | 195 | R5 | 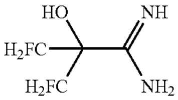 | FA: 139<br>Sal: HCl |
| 176 | R5 | 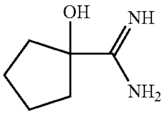 | FA: 129<br>Sal: HCl | 196 | R4 | 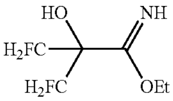 | FA: 168<br>Sal: HCl |
| 177 | R4 | 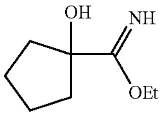 | FA: 158<br>Sal: HCl | 197 | R5 | 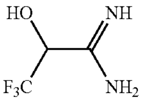 | FA: 143<br>Sal: HCl |

TABLE 9-continued

| | | | | | | | |
|---|---|---|---|---|---|---|---|
| 178 | R5 | 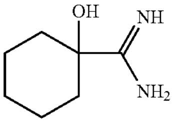 | FA: 143<br>Sal: HCl | 198 | R4 | 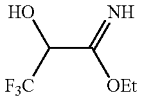 | ES−: 171<br>Sal: HCl |
| 179 | R4 | 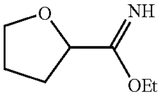 | N1: 1.35 (3H, t, J = 7.0 Hz), 1.76-2.39 (4H, m), 3.75-4.07 (2H, m), 4.42-4.60 (2H, m), 4.75 (1H, dd, J =8.8 Hz, 5.0 Hz), 11.42 (1H, br)<br>Sal: HCl | | | | |
| 180 | R8 | 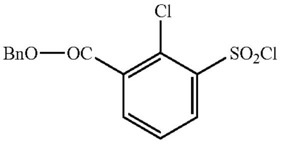 | N1: 5.35 (2H, s), 7.32-7.68 (7H, m), 7.99-8.10 (1H, m) | | | | |

TABLE 10

| REx | Syn | Str | Dat |
|---|---|---|---|
| 199 | R1 | 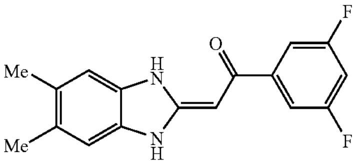 | ES+: 301 |
| 200 | R1 | 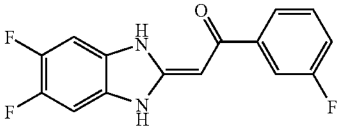 | ES+: 291 |
| 201 | R1 | 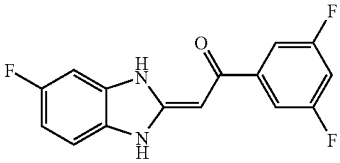 | FA: 291 |
| 202 | R1 | 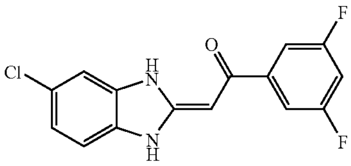 | ES+: 307 |
| 203 | R1 | 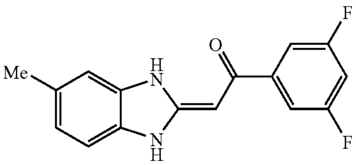 | ES+: 287 |
| 204 | R1 | 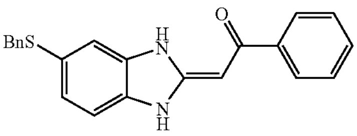 | FA: 359 |

TABLE 10-continued

| REx | Syn | Str | Dat |
|---|---|---|---|
| 205 | R1 | 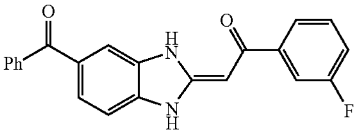 | ES+: 359 |
| 206 | R2 | 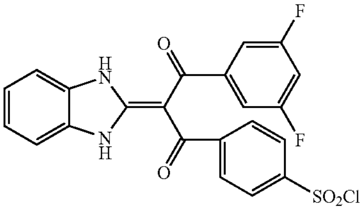 | ES+: 475 |

TABLE 11

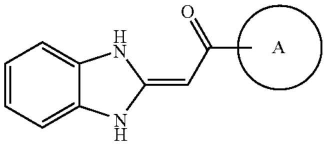

| REx | Syn | A | Dat |
|---|---|---|---|
| 212 | R1 | 3-Cl-4,5-diF-Ph | ES+: 307 |
| 213 | R1 | 3-F-5-Me-Ph | ES+: 269 |
| 214 | R1 | 6-Cl-3Py | ES+: 272 |
| 215 | R1 | 2,4,5-triF-Ph | FA: 291 |
| 216 | R1 | 2,3,4-triF-Ph | ES+: 291 |
| 217 | R1 | 5,6-diCl-3Py | ES+: 306 |
| 218 | R1 | 2-Cl-6-Me-4Py | FA: 286 |
| 219 | R1 | 2,5-diF-4-Cl-Ph | ES+: 307 |
| 220 | R1 | 2,4-diCl-5-F-Ph | ES+: 323 |
| 221 | R1 | 2-Cl-6-OMe-4Py | FA: 302 |
| 222 | R1 | 2,5-diCl-4Py | FA: 306 |
| 223 | R1 | 2,4-diF-3-Cl-Ph | ES+: 307 |
| 224 | R1 | 6-Cl-2Py | FA: 272 |
| 225 | R1 | 3-Cl-4-Me-Ph | ES−: 283 |
| 226 | R1 | 6-CN-3Py | N1: 6.07 (1H, s), 7.20 (2H, m), 7.48 (2H, m), 8.10 (1H, d, J = 8 Hz), 8.40 (1H, d, J = 8, 2 Hz), 9.17 (1H, s) |
| 227 | R1 | 3-F-4-Me-Ph | ES+: 269 |
| 228 | R1 | 2,6-diCl-5-F-3Py | ES+: 324 |
| 229 | R1 | 2-F-5-Cl-Ph | ES+: 289 |
| 230 | R1 | 2-Me-3-Cl-Ph | ES+: 285 |

TABLE 11-continued

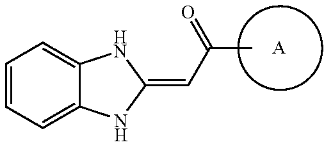

| REx | Syn | A | Dat |
|---|---|---|---|
| 231 | R1 | 2-Cl-3-F-4Py | FA: 290 |
| 232 | R1 | 2-Cl-3-Me-4Py | FA: 286 |
| 233 | R1 | 2,5-diF-Ph | FA: 273 |
| 234 | R1 | 2-Cl-4,5-diF-Ph | FA: 307 |
| 235 | R1 | 5-Cl-2Thi | ES+: 277 |
| 236 | R1 | 2-F-3-Cl-Ph | ES+: 289 |

TABLE 12

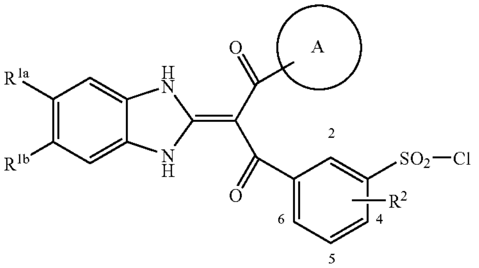

| REx | Syn | A | $R^{1a}$ | $R^{1b}$ | $R^2$ | Dat |
|---|---|---|---|---|---|---|
| 237 | R2 | 2-F-5-Cl-Ph | H | H | H | ES+: 493 |
| 238 | R2 | 3-Cl-4,5-diF-Ph | H | H | H | ES+: 509 |
| 239 | R2 | 3-Cl-4-Me-Ph | H | H | H | Not Isolated |
| 240 | R2 | 3-F-5-Me-Ph | H | H | H | ES+: 471 |
| 241 | R2 | 5,6-diCl-3Py | H | H | H | Not Isolated |
| 242 | R2 | 3-F-Ph | H | H | 4-iPr | Not Isolated |
| 243 | R2 | 2-Me-5-Cl-Ph | H | H | H | ES+: 487 |
| 244 | R2 | 3-F-Ph | H | H | H | ES+: 457 |
| 245 | R2 | 6-Cl-3Py | H | H | H | ES+: 474 |
| 246 | R2 | 6-Cl-3Py | H | H | 4-F | ES+: 492 |
| 247 | R2 | 2,4,5-triF-Ph | H | H | H | FA: 493 |
| 248 | R2 | 2,3,4-triF-Ph | H | H | H | ES+: 493 |
| 249 | R2 | 2-Cl-6-Me-4Py | H | H | H | ES+: 488 |
| 250 | R2 | 3-F-Ph | H | H | 4-F | ES+: 475 |
| 251 | R2 | 2,5-diF-4-Cl-Ph | H | H | H | ES+: 509 |
| 252 | R2 | 2,4-diCl-5-F-Ph | H | H | H | ES−: 525 |
| 253 | R2 | Ph | H | H | 4-F | ES+: 457 |
| 254 | R2 | 3-Me-Ph | H | H | 4-F | ES+: 471 |
| 255 | R2 | 2-Cl-6-OMe-4Py | H | H | H | ES+: 504 |
| 256 | R2 | 3,5-diF-Ph | H | H | 4-F | ES+: 493 |
| 257 | R2 | 2,5-diCl-4Py | H | H | 4-F | FA: 528 |
| 258 | R2 | 2,4-diF-3-Cl-Ph | H | H | H | ES+: 509 |
| 259 | R2 | 2,5-diCl-4Py | H | H | H | FA: 507 |
| 260 | R2 | 6-Cl-2Py | H | H | 4-F | FA: 492 |
| 261 | R2 | 2,4-diCl-5-F-Ph | H | H | 4-F | FN: 541 |
| 262 | R2 | 3-Cl-4-Me-Ph | H | H | 4-F | ES+: 505 |
| 263 | R2 | 4-Cl-Ph | H | H | 4-F | FA: 491 |

TABLE 13

| | | | | | | |
|---|---|---|---|---|---|---|
| 264 | R2 | 6-CN-3Py | H | H | H | ES−: 463 |
| 265 | R2 | 3,4-diMe-Ph | H | H | 4-F | FA: 485 |
| 266 | R2 | 2,4,5-triF-Ph | H | H | 4-F | ES+: 511 |
| 267 | R2 | 2,4-diCl-5-F-3Py | H | H | H | ES+: 528 |
| 268 | R2 | 3-F-4-Me-Ph | H | H | 4-F | ES+: 489 |
| 269 | R2 | 3,4,5-triF-Ph | H | H | 4-F | ES+: 511 |
| 270 | R2 | 2-F-5-Cl-Ph | H | H | 4-F | ES+: 509 |
| 271 | R2 | 2-Me-5-F-Ph | H | H | 4-F | ES+: 489 |
| 272 | R2 | 2-Me-3-F-Ph | H | H | 4-F | ES+: 489 |
| 273 | R2 | 2-Me-3-Cl-Ph | H | H | 4-F | ES+: 505 |

TABLE 13-continued

| | | | | | | |
|---|---|---|---|---|---|---|
| 274 | R2 | 2-Cl-5-F-Ph | H | H | 4-F | FN: 507 |
| 275 | R2 | 3-F-5-Me-Ph | H | H | 4-F | FA: 489 |
| 276 | R2 | 2-Cl-6-OMe-4Py | H | H | 4-F | ES+: 522 |
| 277 | R2 | 2-Cl-4,5-diF-Ph | H | H | 4-F | Not Isolated |
| 278 | R2 | 3-Cl-Ph | H | H | 4-F | FA: 491 |
| 279 | R2 | 2-Cl-3-F-4Py | H | H | H | Not Isolated |
| 280 | R2 | 2-Cl-3-Me-4Py | H | H | 4-F | FA: 506 |
| 281 | R2 | 2,5-diF-4-Cl-Ph | H | H | 4-F | ES+: 527 |
| 282 | R2 | 2,5-diF-Ph | H | H | 4-F | ES+: 493 |
| 283 | R2 | 3-F-4-Me-Ph | H | H | H | ES+: 471 |
| 284 | R2 | 2,5-diF-Ph | H | H | H | ES+: 475 |
| 285 | R2 | 3-F-Ph | H | H | 6-F | Not Isolated |
| 286 | R2 | 3-F-Ph | H | H | 5-F | ES+: 475 |
| 287 | R2 | 3-Cl-4,5-diF-Ph | H | H | 4-F | ES+: 527 |
| 288 | R2 | 3,4,5-triF-Ph | H | H | H | ES+: 493 |
| 289 | R2 | 5-Cl-2Thi | H | H | H | ES+: 481 |
| 290 | R2 | 5-Cl-2Thi | H | H | 4-F | FA: 497 |
| 291 | R2 | 2,6-diCl-4Py | H | H | H | Not Isolated |
| 292 | R2 | 3-F-Ph | $CO_2Bn$ | H | H | FA: 591 |
| 293 | R2 | 3-$CO_2$Me-Ph | H | H | H | ES+: 497 |
| 294 | R2 | 3-F-4-Me-Ph | H | H | 2-Me | ES+: 485 |
| 295 | R2 | 3-F-Ph | H | H | 4-OMe | FA: 487 |
| 296 | R2 | 3-F-Ph | H | H | 2-OMe | FA: 487 |
| 297 | R2 | 2-F-3-Cl-Ph | H | H | H | Not Isolated |

TABLE 14

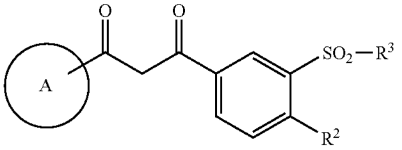

| REx | Syn | A | $R^2$ | $R^3$ | Dat |
|---|---|---|---|---|---|
| 207 | R207 | 3-F-Ph | H | 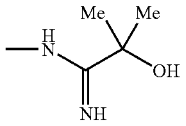 | FA: 407 |
| 298 | R207 | 2Py | H | 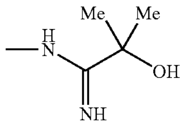 | FA: 390 |
| 299 | R207 | 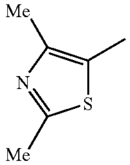 | H | 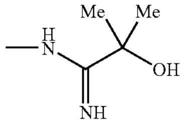 | FA: 424 |
| 300 | R207 | 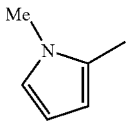 | H | 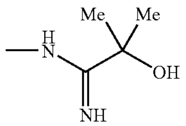 | FA: 392 |
| 301 | R207 | 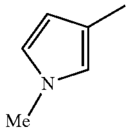 | H | 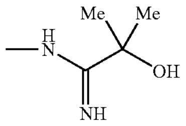 | FA: 392 |

TABLE 14-continued
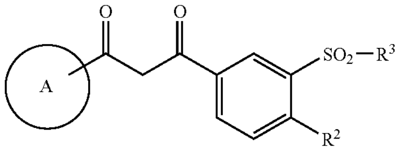
| REx | Syn | A | $R^2$ | $R^3$ | Dat |
|---|---|---|---|---|---|
| 302 | R207 | 3-Thi | H | 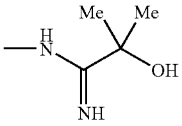 | FA: 395 |
| 303 | R207 | 2-Thi | H | 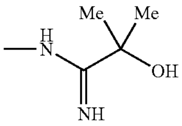 | FA: 395 |
| 304 | R207 | 5-Me-2Thi | H | 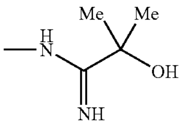 | FA: 409 |
| 305 | R207 | 5-Me-2Fur | H | 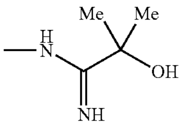 | FA: 393 |
TABLE 15
| | | | | | |
|---|---|---|---|---|---|
| 306 | R207 | 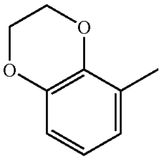 | H | 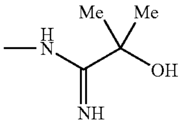 | ES+: 447 |
| 307 | R207 | 4-Me-2Thi | H | 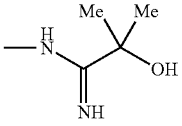 | FA: 409 |
| 308 | R207 | 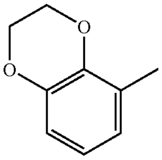 | H | 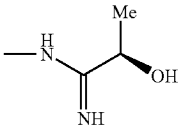 | ES+: 432 |
| 309 | R207 | 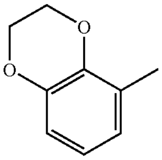 | F | 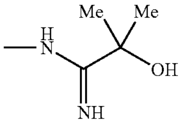 | ES+: 465 |
TABLE 15-continued
| | | | | | |
|---|---|---|---|---|---|
| 310 | R207 | 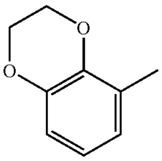 | F | 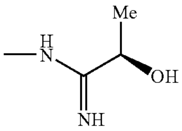 | ES+: 451 |
| 311 | R207 | 3-Me-2Thi | H | 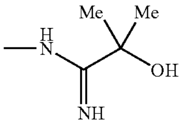 | FA: 409 |
| 312 | R207 | 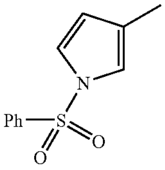 | H | 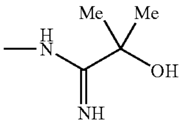 | FA: 518 |
| 313 | R207 | 2,6-diF-3-Me-Ph | H | 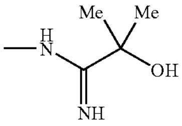 | ES+: 439 |
TABLE 16
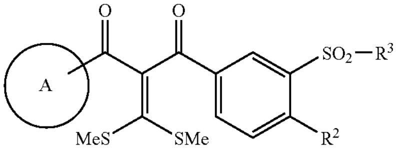
| REx | Syn | A | $R^2$ | $R^3$ | Dat |
|---|---|---|---|---|---|
| 314 | R208 | 2Py | H | 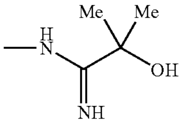 | FA: 494 |
| 315 | R208 | 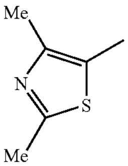 | H | 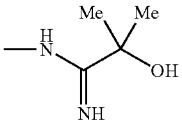 | FA: 528 |
| 316 | R208 | 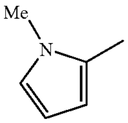 | H | 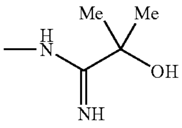 | FA: 496 |
| 317 | R208 | 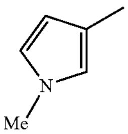 | H | 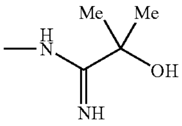 | FA: 496 |

TABLE 16-continued
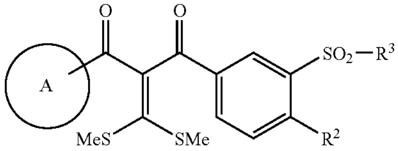
| REx | Syn | A | $R^2$ | $R^3$ | Dat |
|---|---|---|---|---|---|
| 208 | R208 | 3-F-Ph | H | 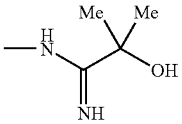 | FA: 511 |
| 318 | R208 | 3-Thi | H | 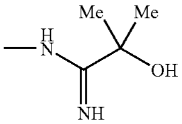 | FA: 499 |
| 319 | R208 | 2-Thi | H | 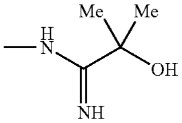 | FA: 499 |
| 320 | R208 | 5-Me-2Thi | H | 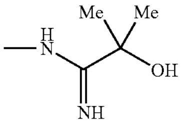 | FA: 513 |
| 321 | R208 | 5-Me-2Fur | H | 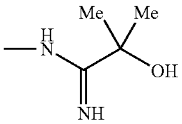 | FA: 497 |
| 322 | R208 | 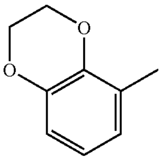 | H | 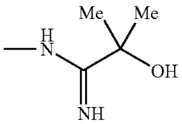 | ES+: 551 |
TABLE 17
| | | | | | |
|---|---|---|---|---|---|
| 323 | R208 | 4-Me-2Thi | H | 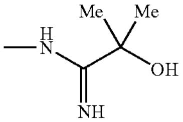 | FA: 513 |
| 324 | R208 | 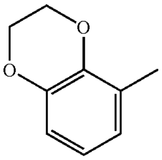 | H | 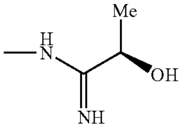 | ES+: 537 |
| 325 | R208 | 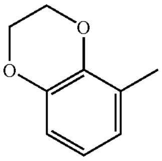 | F | 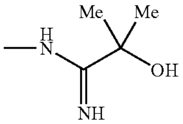 | ES+: 569 |
| 326 | R208 | 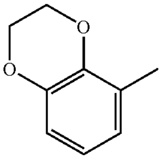 | F | 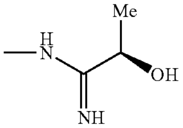 | ES+: 555 |
| 327 | R208 | 3-Me-2Thi | H | 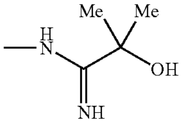 | FA: 513 |
| 328 | R208 | 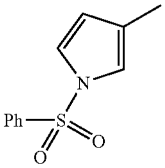 | H | 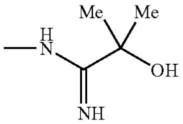 | FA: 622 |
| 329 | R208 | 2,6-diF-3-Me-Ph | H | 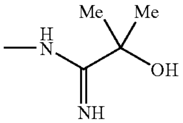 | ES+: 543 |
TABLE 18
| (1) | | | |
|---|---|---|---|
| REx | Syn | Str | Dat |
| 330 | | 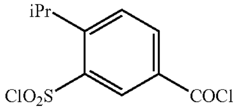 | Not Isolated |
| 331 | | 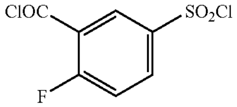 | Not Isolated |

TABLE 18-continued
| | | | |
|---|---|---|---|
| 210 | R210 | 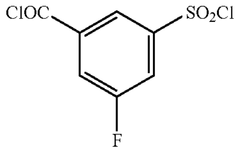 | Not Isolated |
| 332 | | 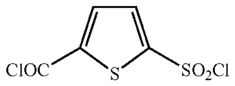 | Not Isolated |
| 333 | | 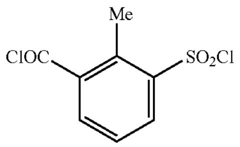 | Not Isolated |
| 209 | R209 | 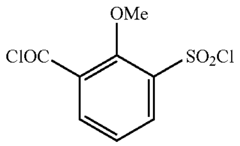 | Not Isolated |
| 211 | R211 | 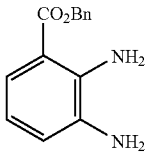 | EI: 242 |
(2)
| REx | Syn | Str | Dat |
|---|---|---|---|
| 334 | R1 | 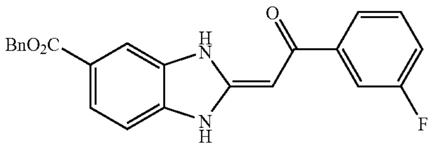 | FA: 389 |
| 335 | R2 | 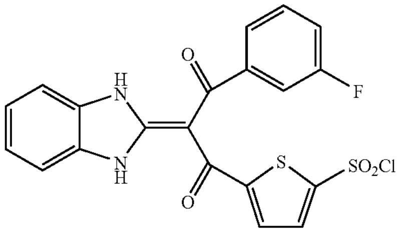 | ES+: 463 |
| 336 | R2 | 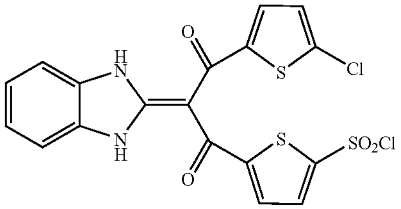 | ES+: 487 |

TABLE 18-continued

| | | | |
|---|---|---|---|
| 337 | R208 | 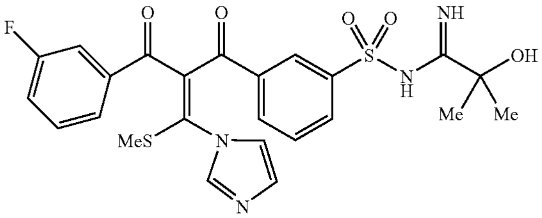 | FA: 531 |

TABLE 19

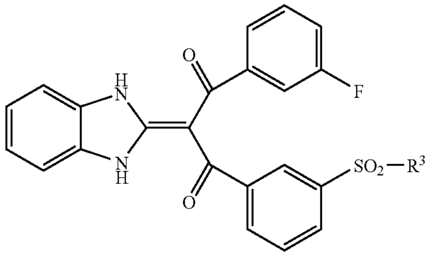

(1)

| Ex | Syn | $R^3$ | Dat |
|---|---|---|---|
| 20 | 3 | —$NH(CH_2)_3OH$ | FA: 496; N1: 1.47-1.59 (2H, m), 2.58-2.68 (2H, m), 3.34-3.42 (2H, m), 4.44 (1H, t, J = 5.2 Hz), 6.88-6.98 (1H, m), 7.02-7.15 (3H, m), 7.24-7.36 (3H, m), 7.49-7.57 (3H, m), 7.66-7.79 (3H, m), 13.13 (2H, s) |
| 21 | 3 | (R)-$NHCH_2CH(Me)OH$ | FA: 496: n1: 1.02 (3H, d, J = 6.4 Hz), 2.41-2.59 (2H, m), 3.53-3.67 (1H, m), 4.70 (1H, br), 6.87-7.82 (13H, m), 13.13 (2H, s) |
| 22 | 2 | —$NHCH_2C(Me)_2OH$ | FA: 510; N1: 1.06 (6H, s), 2.43-2.55 (2H, m), 4.41 (1H, s), 6.87-7.17 (4H, m), 7.22-7.38 (3H, m), 7.44-7.60 (3H, m), 7.67-7.81 (3H, m), 13.13 (2H, s) |

(2)

| Ex | Syn | $R^3$ | Dat |
|---|---|---|---|
| 23 | 3 | (S)-$NHCH_2CH(Me)OH$ | FA: 496 |
| 24 | 3 | (R)-$NHCH_2CH(OH)CH_2OH$ | FA: 512 |
| 25 | 3 | (S)-$NHCH_2CH(OH)CH_2OH$ | FA: 512 |
| 26 | 3 | —$NHCH(Me)CH_2OH$ | FA: 496 |
| 27 | 1 | —NH—C(═NH)—CH(OH)-Et | FA: 523 |
| 28 | 1 | —NH—C(═NH)-Pyra | FA: 543 |
| 29 | 12 | —NH—C(═NH)-Ac | FA: 507 |
| 30 | 2 | —N(OMe)—C(═NH)—$NH_2$ | FA: 510 |
| 31 | 1 | —NH—C(═NH)—CH(OH)-Me | FA: 509 |
| 32 | 3 | —$NHCH_2C(Me)_2CH_2OH$ | FA: 524 |
| 33 | 4 | 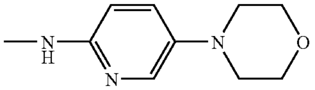 | FA: 600 |
| 34 | 4 | 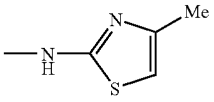 | FA: 5335 |
| 35 | 4 | 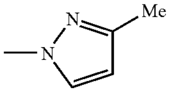 | FA: 503 |
| 48 | 3 | —$NH_2$ | FA: 438 |
| 49 | 5 | —NHAc | FA: 480 |
| 50 | 5 | —NHCOiPr | FA: 508 |
| 51 | 4 | —NH-(5-Cl-2Py) | ES+: 549 |
| 52 | 4 | —NH-(5-Me-2Py) | FA: 529 |

TABLE 19-continued
| | | | |
|---|---|---|---|
| 53 | 4 | —NH-(4-Me-2Py) | FA: 529 |
| 54 | 4 | —NHNH-(2-Py) | FA: 530 |
| 55 | 4 | —NH-(6-Cl-2Py) | FA: 549 |
| 56 | 4 | —NH-(4-Et-2Py) | FA: 543 |
| 57 | 3 | —NH$(CH_2)_2$OH | FA: 482 |
| 58 | 4 | —NH-(2Py) | ES+: 515 |
| 59 | 1 | 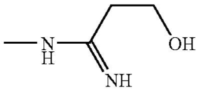 | FA: 509 |
| 60 | 4 | 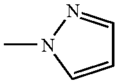 | FA: 489 |
TABLE 20
| | | | |
|---|---|---|---|
| 36 | 4 | 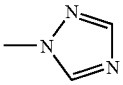 | FA: 490 |
| 37 | 4 | —NH-(5-$CF_3$-2Py) | FA: 583 |
| 38 | 4 | —NH-(4,6-diMe-2Py) | FA: 543 |
| 39 | 4 | —H-(3-$CH_2$OH-2Py) | ES+: 545 |
| 40 | 2 | —N(OBn)—C(═NH)—$NH_2$ | FA: 586 |
| 41 | 4 | 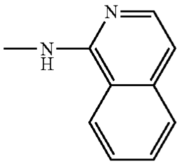 | FA: 565 |
| 42 | 4 | 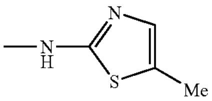 | FA: 535 |
| 43 | 4 | 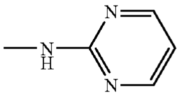 | FA: 516 |
| 44 | 4 | 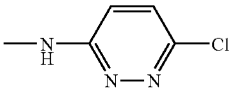 | FA: 550 |
| 45 | 4 | 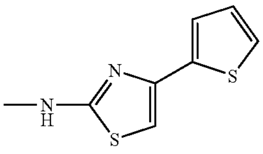 | FA: 603 |
| 46 | 4 | 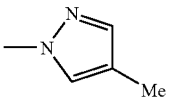 | FA: 503 |
| 47 | 4 | 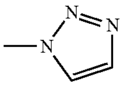 | FA: 490 |
TABLE 20-continued
| | | | |
|---|---|---|---|
| 61 | 4 | 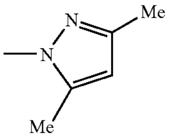 | FA: 517 |
| 62 | 4 | —NMe-(2-Py) | FA: 529 |
| 63 | 4 | —O-(2-$NH_2$-3Py) | FA: 531 |
| 64 | 4 | —NH-Pyra | FA: 516 |
| 65 | 4 | —N(Me)-$NH_2$ | FA: 467 |
| 66 | 4 | 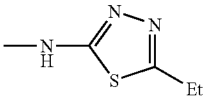 | FA: 550 |
| 67 | 1 | 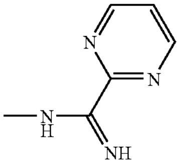 | ES+: 543 |
| 68 | 4 | 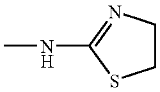 | ES+: 523 |
| 69 | 4 | 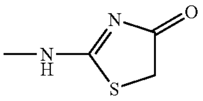 | FA: 537 |
| 70 | 4 | 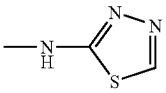 | FA: 522 |
| 71 | 4 | 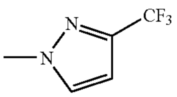 | FA: 557 |

TABLE 21
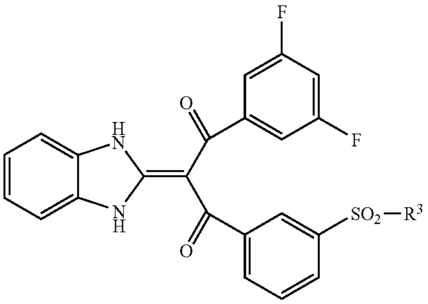
(1)
| Ex | Syn | $R^3$ | Dat |
|---|---|---|---|
| 4 | 4 | —NH-(2Py) | FA: 533; N1: 6.74-6.95 (4H, m), 7.00-7.20 (1H, m), 7.25-7.37 (3H, m), 7.45-7.57 (1H, m), 7.62-8.07 (6H, m), 13.12 (2H, s) |
| 5 | 5 | —NHAc | FA: 498; N1: 1.92 (3H, s), 6.85-7.04 (3H, m), 7.28-7.47 (3H, m), 7.62-7.82 (5H, m), 12.06 (1H, br), 13.16 (2H, s) |
| 12 | 12 | —H—C(═NH)-Ac | FA: 525; N1: 2.35 (3H, s), 6.82-6.94 (3H, m), 7.26-7.40 (3H, m), 7.52-7.62 (1H, m), 7.70-7.81 (4H, m), 8.30 (1H, br), 8.77 (1H, br), 13.16 (2H, s) |
| 15 | 15 | 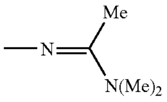 | FA: 525; N1: 2.32 (3H, s), 3.00 (3H, s), 3.11 (3H, s), 6.86-7.02 (3H, m), 7.25-7.36 (3H, m), 7.46-7.52 (1H, m), 7.56-7.62 (1H, m), 7.66-7.80 (3H, m), 13.12 (2H, br) |
| 72 | 3 | 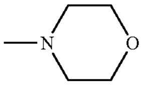 | FA: 526; N1: 2.77 (4H, t, J = 4.4 Hz), 3.62 (4H, t, J = 4.4 Hz), 6.92-7.02 (3H, m), 7.30-7.38 (2H, m), 7.40-7.48 (1H, m), 7.53-7.82 (5H, m), 13.17 (2H, s) |
| 73 | 1 | —NH—C(═NH)-Me | FA: 497; N1: 2.02 (3H, s), 6.84-7.00 (3H, m), 7.25-7.37 (3H, m), 7.49-7.80 (5H, m), 8.07 (1H, br), 8.50 (1H, br), 13.13 (2H, s) |
| 74 | 2 | 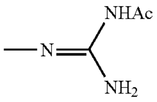 | FA: 540; N1: 2.05 (3H, s), 6.84-6.97 (3H, m), 7.26-7.40 (3H, m), 7.53-7.80 (5H, m), 7.98 (1H, s), 8.97 (1H, s), 11.07 (1H, s), 13.13 (2H, s) |
| 75 | 1 | —NH—C(═NH)-2Py | FA: 560; N1: 6.73-6.90 (3H, m), 7.25-7.40 (3H, m), 7.52-7.60 (1H, m), 7.64-7.85 (5H, m), 7.95-8.05 (1H, m), 8.07-8.15 (1H, m), 8.34 (1H, br), 8.72 (1H, d, J = 3.7 Hz), 9.03 (1H, br), 13.14 (2H, s) |
| 76 | 1 | —NH—C(═NH)-OMe | FA: 513; N1: 3.66 (3H, s), 6.79-7.00 (3H, m), 7.21-7.40 (4H, m), 7.47-7.58 (1H, m), 7.62-7.82 (4H, m), 8.28 (1H, br), 13.15 (2H, s) |
| 77 | 3 | —NH$(CH_2)_2$OH | FA: 500; N1: 2.65 (2H, d, J = 12.2 Hz, 5.9 Hz), 3.28-3.42 (2H, m), 4.69 (1H, br), 6.90-7.00 (3H, m), 7.28-7.36 (2H, m), 7.38 (1H, t, J = 7.8 Hz), 7.54-7.80 (6H, m), 13.15 (2H, s) |
| 78 | 3 | 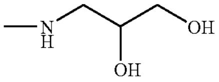 | FA: 530; N1: 2.65-2.83 (1H, m), 3.18-3.58 (4H, m), 4.67 (2H, br), 6.82-7.02 (3H, m), 7.21-7.43 (3H, m), 7.45-7.83 (6H, m), 13.15 (2H, s) |

TABLE 22

| | | | |
|---|---|---|---|
| 79 | 1 | —N═C(NH$_2$)—NH-Me | FA: 512, N1: 2.64 (3H, d, J = 4.4 Hz), 6.63 (2H, br), 6.82-6.96 (3H, m), 7.02 (1H, br), 7.22-7.37 (3H, m), 7.42-7.50 (1H, m), 7.52-7.60 (1H, m), 7.64 (1H, br), 7.71-7.79 (2H, m), 13.11 (2H, s) |
| 80 | 1 | —NH—C(═NH)-cBu | FA: 537; N1: 1.64-1.77 (1H, m), 1.78-1.92 (1H, m), 1.98-2.18 (4H, m), 3.10-3.20 (1H, m), 6.84-6.96 (3H, m), 7.26-7.36 (3H, m), 7.49-7.56 (1H, m), 7.62-7.80 (4H, m), 7.83 (1H, br), 8.45 (1H, br), 13.13 (2H, s) |
| 81 | 1 | —H—C(═NH)—CH$_2$SMe | FA: 543; N1: 2.04 (3H, s), 3.18 (2H, s), 6.82-7.02 (3H, m), 7.25-7.42 (3H, m), 7.48-7.84 (5H, m), 8.03 (1H, br), 8.64 (1H, br), 13.14 (2H, s) |
| 82 | 1 | —NH—C(═NH)—C(Me)$_2$OH | FA: 541; N1: 1.25 (6H, s), 5.77 (1H, s), 6.84-6.98 (3H, m), 7.24-7.38 (3H, m), 7.47-7.64 (2H, m), 7.67-7.82 (3H, m), 8.02 (1H, br), 8.10 (1H, br), 13.14 (2H, s) |
| 83 | 1 | —NH—C(═NH)—CH(cPr)OH | FA: 553; N1: 0.21-0.41 (4H, m), 0.95-1.09 (1H, m), 3.69 (1H, t, J = 5.4 Hz), 5.79 (1H, d, J = 5.4 Hz), 6.84-6.98 (3H, m), 7.26-7.38 (3H, m), 7.50-7.58 (1H, m), 7.60-7.67 (1H, m), 7.69-7.80 (3H, m), 8.01 (1H, br), 8.17 (1H, br), 13.14 (2H, s) |
| 84 | 1 | 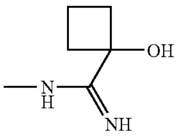 | FA: 553; N1: 1.64-1.85 (2H, m), 1.98-2.12 (2H, m), 2.25-2.38 (2H, m), 6.32 (1H, s), 6.85-6.96 (3H, m), 7.27-7.38 (3H, m), 7.50-7.57 (1H, m), 7.62-7.68 (1H, m), 7.70-7.80 (3H, m), 7.94 (1H, br), 8.01 (1H, br), 13.13 (2H, s) |
| 85 | 1 | —NH—C(═NH)—CH$_2$OH | FA: 513; N1: 4.06 (2H, d, J = 5.9 Hz), 5.86 (1H, t, J = 5.9 Hz), 6.86-6.99 (3H, m), 7.28-7.38 (3H, m), 7.50- 7.80 (5H, m), 8.18 (1H, br), 8.33 (1H, br), 13.14 (2H, s) |
| 86 | 1 | —NH—C(═NH)—CH(Me)OH | FA: 527; N1: 1.21 (3H, d, J = 6.6 Hz), 4.07-4.17 (1H, m), 5.85 (1H, d, J = 4.9 Hz), 6.83-6.98 (3H, m), 7.26-7.38 (3H, m), 7.48-7.82 (5H, m), 8.06 (1H, br), 8.16 (1H, br), 13.14 (2H, s) |
| 87 | 3 | —NH(CH$_2$)$_3$OH | FA: 514; N1: 1.46-1.58 (2H, m), 2.58-2.70 (2H, m), 3.26-3.46 (2H, m), 4.43 (1H, br), 6.89-7.02 (3H, m), 7.27-7.42 (3H, m), 7.53-7.82 (6H, m), 13.15 (2H, s) |
| 88 | 3 | —NHCH$_2$CH(Me)OH | FA: 5114; N1: 1.00 (3H, d, J = 6.4 Hz), 2.40-2.61 (2H, m), 3.50-3.68 (1H, m), 4.67 (1H, br), 6.85-7.02 (3H, m), 7.25-7.43 (3H, m), 7.47-7.83 (6H, m), 13.15 (2H, s) |
| 89 | 1 | —N═C(NH$_2$)$_2$ | FA: 498; N1: 6.70 (4H, br), 6.82-6.98 (3H, m), 7.23-7.38 (3H, m), 7.43-7.88 (5H, m), 13.11 (2H, s) |
| 90 | 1 | —H—C(═NH)—CH$_2$OMe | ES+: 527; N1: 3.32 (3H, s), 4.06 (2H, s), 6.85-6.99 (3H, m), 7.26-7.39 (3H, m), 7.49-7.82 (5H, m), 8.31 (1H, br), 8.35 (1H, br), 13.14 (2H, s) |
| 91 | 1 | —NH—C(═NH)-(2THF) | FA: 553; N1: 1.68-1.88 (3H, m), 2.12-2.28 (1H, m), 3.70-3.82 (1H, m), 3.86-3.97 (1H, m), 4.31-4.42 (1H, m), 6.83-6.98 (3H, m), 7.26-7.37 (3H, m), 7.48-7.80 (5H, m), 8.12 (1H, br), 8.28 (1H, br), 13.14 (2H, s) |

TABLE 23

| | | | |
|---|---|---|---|
| 92 | 4 | 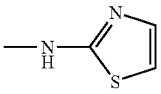 | FA: 539; N1: 6.77-6.93 (4H, m), 7.22-7.38 (4H, m), 7.45-7.85 (5H, m), 12.78 (1H, br), 13.11 (2H, s) |
| 93 | 3 | —NHMe | FA: 470; N1: 2.31 (3H, d, J = 4.4 Hz), 6.91-7.03 (3H, m), 7.27-7.45 (3H, m), 7.46-7.82 (6H, m), 13.15 (2H, s) |
| 94 | 1 | —NH—C(═NH)—CH$_2$CONH$_2$ | FA: 540; N1: 3.15 (2H, s), 6.82-6.97 (3H, m), 7.10 (1H, br), 7.26-7.37 (3H, m), 7.41-7.82 (6H, m), 8.10 (1H, br), 8.66 (1H, br), 13.14 (2H, s) |

TABLE 23-continued
| | | | |
|---|---|---|---|
| 95 | 1 | 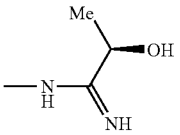 | FA: 527; N1: N1: 1.20 (3H, d, J = 6.9 Hz), 4.06-4.17 (1H, m), 5.85 (1H, d, J = 4.9 Hz), 6.86-6.98 (3H, m), 7.27-7.37 (3H, m), 7.50-7.57 (1H, m), 7.59-7.65 (1H, m), 7.67-7.80 (3H, m)(, 8.06 (1H, br), 8.16 (1H, br), 13.14 (2H, s) |
| 96 | 16 | 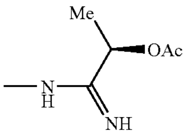 | FA: 569; N1: 1.31 (3H, d, J = 7.2 Hz), 2.00 (3H, s), 4.94-5.05 (1H, m), 6.83-6.97 (3H, m), 7.26-7.38 (3H, m), 7.50-7.64 (2H, m), 7.65-7.81 (3H, m), 8.09 (1H, br), 8.68 (1H, br), 13.14 (2H, s) |
| 97 | 10 | —NH—C(=$NNH_2$)—$H_2$ | FA: 513; N1: 4.46 (2H, br), 6.81-7.05 (5H, m), 7.22-7.37 (3H, m), 7.41-7.58 (2H, m), 7.60-7.67 (1H, m), 7.69-7.81 (2H, m), 8.43 (1H, br), 13.11 (2H, s) |
(2)
| Ex | Syn | $R^3$ | Dat |
|---|---|---|---|
| 98 | 3 | 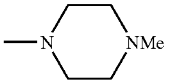 | FA: 539<br>Sal: HCl |
| 99 | 3 | 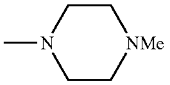 | FA: 525 |
| 100 | 2 | 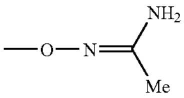 | FA: 513 |
| 101 | 4 | 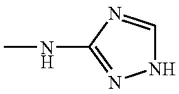 | FA: 523 |
| 102 | 4 | 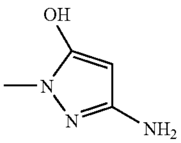 | FA: 538 |
| 120 | 1 | 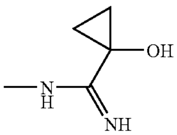 | FA: 539 |
| 121 | 1 | 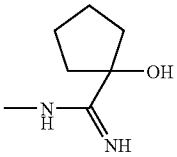 | FA: 567 |
| 122 | 1 | 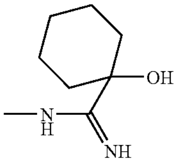 | FA: 581 |

TABLE 23-continued
| | | | |
|---|---|---|---|
| 123 | 1 | 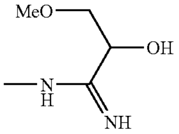 | FA: 557 |
| 124 | 1 | 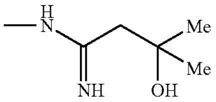 | FA: 555 |
TABLE 24
| | | | |
|---|---|---|---|
| 103 | 4 | 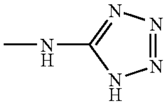 | FA: 524 |
| 104 | 4 | 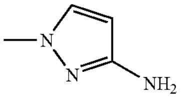 | FA: 522 |
| 105 | 4 | 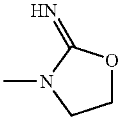 | ES+: 525 |
| 106 | 4 | 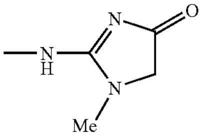 | FA: 552 |
| 107 | 3 | 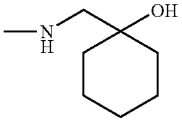 | FA: 568 |
| 108 | 3 | 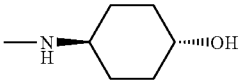 | FA: 554 |
| 109 | 3 | 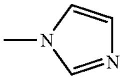 | FA: 507 |
| 110 | 3 | 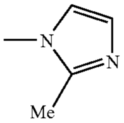 | FA: 521 |
| 111 | 3 | 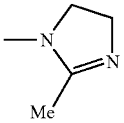 | FA: 523 |
| 112 | 4 | 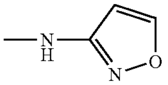 | FA: 523 |
TABLE 24-continued
| | | | |
|---|---|---|---|
| 113 | 3 | 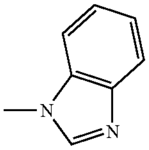 | FA: 557 |
| 125 | 1 | 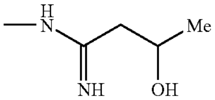 | FA: 541 |
| 126 | 1 | 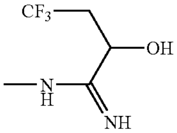 | FA: 595 |
| 127 | 12 | 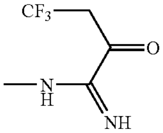 | FN: 591 |
| 128 | 1 | 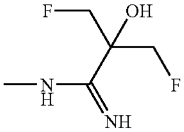 | FA: 577 |
| 129 | 1 | 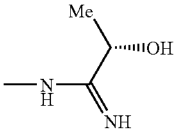 | FA: 527 |
| 130 | 13 | 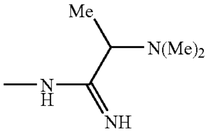 | FA: 554 |
| 131 | 17 | 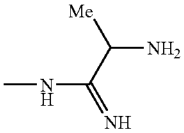 | FA: 526 |

TABLE 24-continued

| | | | |
|---|---|---|---|
| 132 | 2 | 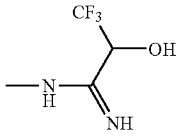 | FA: 581 |
| 133 | 13 | 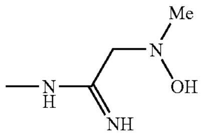 | FA: 542 |
| 134 | 13 | 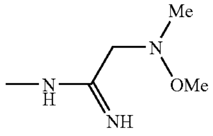 | FA: 556 |
| 135 | 1 | 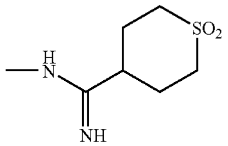 | FA: 615 |

TABLE 25

| | | | |
|---|---|---|---|
| 114 | 3 | 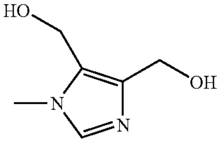 | FA: 567 |
| 115 | 1 | 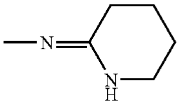 | FA: 537 |
| 116 | 1 | 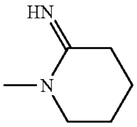 | FA: 537 |
| 117 | 1 | 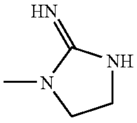 | FA: 524 |
| 118 | 1 | 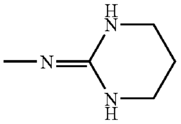 | FN: 536 |
| 119 | 2 | 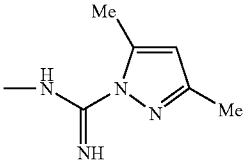 | ES+: 577 |

TABLE 25-continued

| | | | |
|---|---|---|---|
| 140 | 1 | 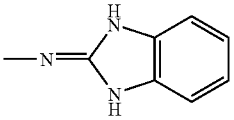 | FA: 572 |
| 136 | 1 | 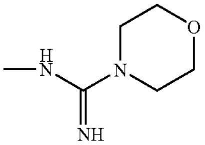 | FA: 568 |
| 137 | 2 | 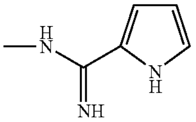 | FA: 548 |
| 11 | 11 | 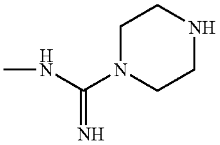 | FA: 567 |
| 138 | 2 | 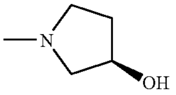 | FA: 526 |
| 139 | 1 | 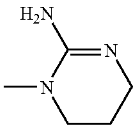 | FA: 538 |
| 10 | 10 | 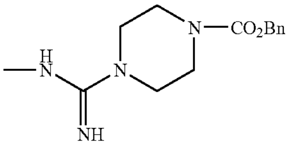 | ES+: 701 |

(3)

| Ex | Syn | $R^3$ | Dat |
|---|---|---|---|
| 141 | 1 | —NH—C(═NH)-(3Fur) | FA: 549 |
| 142 | 1 | —NH—C(═NH)—CH(iPr)OH | FA: 555 |
| 143 | 1 | —NH—C(═NH)—$CONH_2$ | FA: 526 |
| 144 | 3 | —NH—C(═NH)-(2Fur) | FA: 549 |
| 145 | 1 | —NH—C(═NH)—CH(Pr)OH | FA: 555 |
| 146 | 3 | (S)-$NHCH_2CH(Me)OH$ | FA: 514 |
| 147 | 3 | (R)-$NHCH_2CH(OH)CH_2OH$ | FA: 530 |
| 148 | 3 | (R)-$NHCH_2CH(Me)OH$ | FA: 514 |
| 149 | 3 | (S)-$NHCH_2CH(OH)CH_2OH$ | FA: 530 |
| 150 | 1 | —NH—C(═NH)—CH(Ph)OH | FA: 589 |
| 1 | 1 | —NH—CH═NH | FA: 483 |
| 2 | 2 | —$NHCH_2CO_2Et$ | FA: 542 |
| 3 | 3 | —$NHCH_2CN$ | FA: 495 |
| 6 | 6 | —NHCONH-iPr | FA: 541 |
| 7 | 7 | —$NHCONH_2$ | ES+: 499 |
| 8 | 8 | —$NHCH_2CO_2H$ | FA: 514 |
| 178 | 14 | Me | FA: 455 |
| 179 | 1 | —NH—C(═NH)-Ph | FA: 559 |
| 180 | 1 | —NH—C(═NH)-iPr | FA: 525 |
| 181 | 1 | —NH—C(═NH)-cPr | FA: 523 |

TABLE 26

| | | | | | | | |
|---|---|---|---|---|---|---|---|
| 151 | 1 | —NH—C(═NH)—CH$_2$CO$_2$Et | FA: 569 | 182 | 1 | —NH—C(═NH)-tBu | FA: 539 |
| 152 | 1 | —NH—C(═NH)—CH$_2$NH$_2$ | FA: 512 | 183 | 1 | —NH—C(═NH)-Et | FA: 511 |
| 153 | 3 | —NH(CH$_2$)$_2$O(CH$_2$)$_2$OH | FA: 544 | 184 | 3 | —NH$_2$ | FA: 456 |
| 154 | 2 | —NHCH(CO$_2$Me)CH$_2$OH | FA: 558 | 185 | 1 | —NH—C(═NH)—Pr | FA: 525 |
| 155 | 6 | —NHCH(CO$_2$H)CH$_2$OH | FA: 544 | 186 | 4 | —NH-(4Py) | FA: 533 |
| 156 | 1 | —NH—C(═NH)—CH$_2$CH$_2$OMe | FA: 541 | 187 | 4 | —NH-(3-Me-2Py) | FA: 547 |
| 157 | 1 | —NH—C(═NH)—CH$_2$SO$_2$Me | FA: 575 | 188 | 11 | —NH-(3-OH-2Py) | FA: 549 |
| 158 | 3 | —NHCH$_2$C(Me)$_2$CH$_2$OH | FA: 542 | 189 | 4 | —NH-(6-Me-2Py) | FA: 547 |
| 159 | 3 | —NHCH(Me)CH$_2$OH | FA: 514 | 190 | 3 | —OH | FA: 457 |
| 160 | 1 | —NH—C(═NH)—CH$_2$CH$_2$OH | FA: 527 | 191 | 5 | —NH—COiPr | FA: 526 |
| 161 | 1 | —NH—C(═NH)-(4THP) | FA: 567 | 192 | 4 | —NH-(3Py) | FA: 533 |
| 162 | 1 | —NH—C(═NH)—NH(CH$_2$)$_2$OH | FA: 542 | 193 | 4 | —NH-(3-OBn-2Py) | FA: 639 |
| 163 | 3 | —NH—C(═NH)—CH$_2$OPh | FA: 589 | 194 | 5 | —NHCO$_2$Et | FA: 528 |
| 164 | 1 | —NH—C(═NH)—CH(Et)OH | FA: 541 | 195 | 3 | —NH(CH$_2$)$_2$NH$_2$ | FA: 499 |
| 165 | 12 | —NH—C(═NH)—CO-Et | FA: 539 | 196 | 3 | —NH(CH$_2$)$_4$OH | FA: 528 |
| 166 | 12 | —NH—C(═NH)—CO—Pr | FA: 553 | 197 | 3 | —NH(CH$_2$)$_2$OMe | FA: 514 |
| 167 | 1 | —N═C(NH$_2$)—N(Me)$_2$ | FA: 526 | 198 | 3 | —N[(CH$_2$)$_2$OH]$_2$ | FA: 544 |
| 168 | 1 | —NH—C(═NH)—CO$_2$Et | FA: 555 | 199 | 3 | —NHCH(CH$_2$OH)$_2$ | FA: 530 |
| 169 | 8 | —NH—C(═NH)—CO$_2$H | FN: 525 | 200 | 2 | —NHCH$_2$C(Me)$_2$OH | FA: 528 |
| 9 | 9 | —NH—C(═NH)—CON(Me)$_2$ | FA: 554 | 201 | 12 | —NHC(═NH)—CHO | FN: 509 |
| 13 | 13 | —NH—C(═NH)—CH$_2$N(Me)$_2$ | FA: 540 | 202 | 3 | —NHC(Me)$_2$CH$_2$OH | FA: 528 |
| 16 | 16 | —NH—C(═NH)—CH$_2$OAc | FA: 555 | 203 | 3 | —NH—C(═NH)—CF$_3$ | ES+: 551 |
| 170 | 1 | —NH—C(═NH)—CH$_2$Cl | FA: 531 | 14 | 14 | —N(Me)$_2$ | FA: 484 |
| 171 | 1 | —NH—C(═NH)—NHCONH$_2$ | FA: 541 | 204 | 4 | —NH(CH$_2$)$_2$OAc | FN: 540 |
| 172 | 1 | —NH—C(═NH)-2Thi | FA: 565 | 205 | 1 | —NH—C(═NH)-3Py | ES+: 560 |
| 173 | 3 | —N(Me)-(CH$_2$)$_2$OH | FA: 514 | 206 | 15 | —N═CH—N(Me)$_2$ | FA: 511 |
| 174 | 2 | —NH—CH$_2$-(3-OH-Ph) | FA: 562 | 207 | 2 | —NHOMe | FA: 486 |
| 175 | 3 | (S)—NH(CH$_2$)$_2$CH(CO$_2$Me)OH | FA: 572 | 208 | 2 | —NHOH | FA: 472 |
| 176 | 13 | —NH—C(═NH)—CH(Me)-N$_3$ | FA: 552 | 209 | 1 | —NH—C(═NH)-4Py | FA: 560 |
| 177 | 16 | —NH—C(═NH)—CH(Me)-OTs | FA: 681 | 210 | 1 | —NH—C(═NH)-Pyra | FA: 561 |

TABLE 27

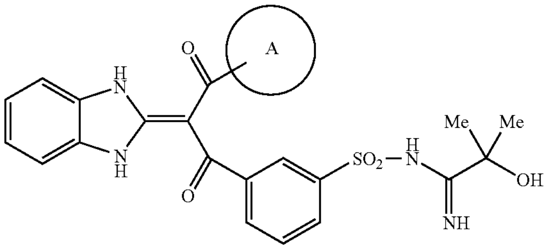

(1)

| Ex | Syn | A | Dat |
|---|---|---|---|
| 211 | 1 | 3-F-Ph | N1: 1.25 (6H, s), 5.78 (1H, s), 6.85-6.94 (1H, m), 6.99-7.12 (3H, m), 7.24 (1H, t, J = 7.5 Hz), 7.27-7.35 (2H, m), 7.44-7.58 (2H, m), 7.68-7.78 (3H, m), 7.98 (1H, br), 8.13 (1H, br), 13.12 (2H, s) |
| 212 | 1 | 3-Me-Ph | FA: 519; N1: 1.25 (6H, s), 2.12 (3H, s), 5.77 (1H, s), 6.82- 6.97 (2H, m), 7.00-7.23 (3H, m), 7.25-7.55 (4H, m), 7.66- 7.79 (3H, m), 7.97 (1H, br), 8.11 (1H, br), 13.12 (2H, s) |
| 213 | 1 | 3-Cl-Ph | FA: 539; N1: 1.26 (6H, s), 5.77 (1H, s), 7.00-7.35 (7H, m), 7.43-7.60 (2H, m), 7.67-7.79 (3H, m), 7.98 (1H, br), 8.14 (1H, br), 13.12 (2H, s) |

(2)

| Ex | Syn | A | Dat |
|---|---|---|---|
| 214 | 1 | 2-Me-3-F-Ph | FA: 537 |
| 215 | 1 | Ph | FA: 505 |
| 216 | 1 | 1Naph | ES+: 555 |
| 217 | 1 | 2-Cl-Ph | ES+: 539 |
| 218 | 1 | 3-F-4-Ome-Ph | FA: 553 |

TABLE 27-continued

| | | | |
|---|---|---|---|
| 219 | 1 | 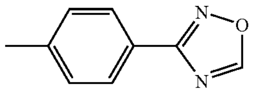 | FA: 573 |
| 220 | 1 | 4-F-1Naph | FA: 573 |
| 221 | 1 | 2-Cl-5-F-Ph | FA: 557 |
| 222 | 1 | 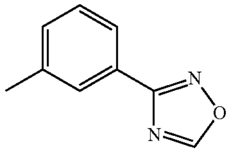 | FA: 573 |
| 223 | 1 | 3,5-diOMe-Ph | FA: 565 |
| 224 | 1 | 4-F-Ph | FA: 523 |
| 225 | 1 | 5,6-diCl-3Py | FA: 574 |
| 226 | 1 | 3-Cl-2-Me-Ph | FA: 553 |
| 227 | 1 | 5-Cl-2-OMe-Ph | FA: 569 |
| 228 | 1 | 4-Cl-Ph | FA: 539 |
| 229 | 1 | 4-Me-Ph | FA: 519 |
| 230 | 1 | 3,4,5-triF-Ph | FA: 559 |
| 231 | 1 | 2,5-diF-Ph | FA: 541 |
| 232 | 1 | 2-Cl-4,5-diF-Ph | FA: 575 |
| 233 | 1 | 6-Cl-3Py | FA: 540 |
| 234 | 1 | 2-F-Ph | FA: 523 |
| 235 | 1 | 2-Me-Ph | FA: 519 |
| 236 | 2 | 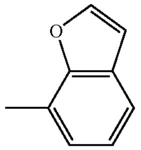 | FA: 545 |
| 237 | 1 | 3-Cl-4Py | FA: 540 |
| 238 | 1 | 3-F-4-me-Ph | FA: 537 |
| 239 | 1 | 5-F-2-OMe-Ph | FN: 551 |
| 240 | 1 | 3-Cl-4-OMe-Ph | FA: 569 |

TABLE 28

(1)

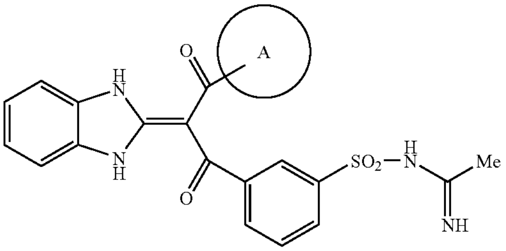

| Ex | Syn | A | Dat |
|---|---|---|---|
| 241 | 1 | 3,4-diMe-Ph | FA: 489; N1: 1.99 (3H, s), 2.01 (3H, s), 2.02 (3H, s), 6.76-6.83 (1H, m), 6.99-7.06 (2H, m), 7.18 (1H, t, J = 7.8 Hz), 7.26-7.33 (2H, m), 7.37-7.43 (1H, m), 7.46-7.52 (1H, m), 7.62-7.67 (1H, m), 7.69-7.76 (2H, m), 8.09 (1H, br), 8.47 (1H, br), 13.08 (2H, s) |
| 242 | 1 | 6-Cl-3Py | ES+: 496; N1: 2.04 (3H, s), 7.13 (1H, d, J = 8.3 Hz), 7.25-7.38 (3H, m), 7.49-7.81 (6H, m), 8.15 (1H, br), 8.22 (1H, d, J = 2.2 Hz), 8.56 (1H, br), 13.20 (2H, s) |
| 243 | 1 | 3-Br-Ph | FA: 541; N1: 2.02 (3H, s), 6.99 (1H, t, J = 7.8 Hz), 7.22-7.43 (6H, m), 7.45-7.51 (1H, m), 7.53-7.60 (1H, m), 7.63-7.68 (1H, m), 7.72-7.79 (2H, m), 8.09 (1H, br), 8.49 (1H, br), 13.11 (2H, s) |
| 244 | 1 | 3-$CF_3$-Ph | FA: 529; N1: 2.01 (3H, s), 7.16-7.36 (4H, m), 7.38-7.60 (5H, m), 7.62-7.66 (1H, m), 7.70-7.80 (2H, m), 8.08 (1H, br), 8.49 (1H, br), 13.15 (2H, s) |
| 245 | 1 | 3-F-Ph | FA: 479; N1: 2.01 (3H, s), 6.87-6.98 (1H, m), 6.99-7.15 (3H, m), 7.21-7.34 (3H, m), 7.45-7.58 (2H, m), 7.64-7.81 (3H, m), 8.09 (1H, br), 8.50 (1H, br), 13.11 (2H, s) |
| 246 | 1 | 3,4,5-triF-Ph | FA: 515; N1: 2.02 (3H, s), 7.06-7.20 (2H, m), 7.27-7.38 (3H, m), 7.48-7.67 (3H, m), 7.72-7.81 (2H, m), 8.08 (1H, br), 8.52 (1H, br), 13.16 (2H, s) |

(2)

| Ex | Syn | A | Dat |
|---|---|---|---|
| 19 | 19 | 4Py | ES+: 462 |
| 247 | 1 | 4-F-1-Naph | FA: 529 |
| 248 | 1 | 2,3-diMe-Ph | FA: 489 |
| 249 | 1 | 2-$CF_3$-Ph | FA: 529 |
| 250 | 1 | 4-$CF_3$-Ph | FA: 529 |
| 251 | 1 | 3,4-diCl-Ph | ES+: 529 |
| 252 | 1 | 3,5-diCl-Ph | FA: 529 |
| 253 | 1 | 3,4-diF-Ph | FA: 497 |
| 254 | 1 | 2,3-diF-Ph | FA: 497 |
| 255 | 1 | 2,5-diF-Ph | FA: 497 |
| 273 | 1 | 2Thi | FA: 467 |
| 274 | 1 | 3Thi | FA: 467 |
| 275 | 1 | Ph | FA: 461 |
| 276 | 1 | 3-OMe-Ph | FA: 491 |
| 277 | 1 | 4-F-Ph | FA: 479 |
| 278 | 1 | 3-OH-Ph | FA: 477 |
| 279 | 1 | 3-$SO_2$NHCMeNH-Ph | FA: 581 |
| 280 | 1 | 3-CN-Ph | FA: 486 |
| 281 | 1 | 2-OPh-Ph | FA: 553 |
| 282 | 1 | 3-OiPr-Ph | FA: 519 |

TABLE 29

| | | | |
|---|---|---|---|
| 256 | 1 | 2,3-diCl-Ph | FA: 529 |
| 257 | 1 | 2,5-diCl-Ph | FA: 529 |
| 258 | 1 | 2-Cl-Ph | ES+: 495 |
| 259 | 1 | 3-Cl-Ph | FA: 495 |
| 260 | 1 | 2-F-Ph | ES+: 479 |
| 261 | 1 | 3-Me-Ph | ES+: 475 |
| 262 | 1 | 2-OMe-Ph | ES+: 491 |
| 263 | 1 | 2-Cl-4Py | ES+: 496 |
| 264 | 11 | 3Py | ES+: 462 |
| 265 | 1 | 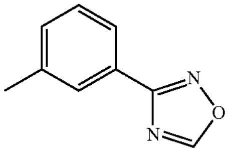 | FA: 529 |
| 266 | 1 | 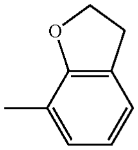 | FA: 503 |
| 267 | 1 | 2-Cl-4,5-diF-Ph | FA: 531 |
| 268 | 1 | 3-F-4-Me-Ph | FA: 493 |
| 269 | 1 | 5-Cl-2-OMe-Ph | FA: 525 |
| 270 | 1 | 3-Cl-5-F-Ph | FA: 513 |
| 271 | 1 | 5-Cl-2-Me-Ph | FA: 509 |
| 272 | 1 | 3-SMe-Ph | FA: 507 |
| 531 | 1 | 2-Me-Ph | FA: 475 |
| 283 | 1 | 3-OPr-Ph | FA: 519 |
| 284 | 1 | 3-OEt-Ph | FA: 505 |
| 285 | 1 | 2-Me-5-F-Ph | FA: 493 |
| 286 | 1 | 2Naph | FA: 511 |
| 287 | 1 | 2-Me-3-F-Ph | FA: 493 |
| 288 | 1 | 3,5-diMe-Ph | FA: 489 |
| 289 | 1 | 2-Ph-Ph | FA: 537 |
| 290 | 1 | 3-Ph-Ph | FA: 537 |
| 291 | 1 | Pyra | FN: 461 |
| 292 | 1 | 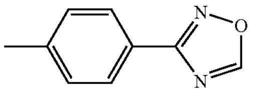 | FA: 529 |
| 293 | 2 | 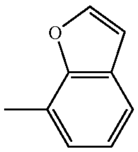 | FA: 501 |
| 294 | 1 | 3-F-4-OMe-Ph | FA: 509 |
| 295 | 1 | 2-Cl-3-F-Ph | FA: 513 |
| 296 | 1 | 3-Cl-4-OMe-Ph | FA: 525 |
| 297 | 1 | 5-F-2-OMe-Ph | FA: 509 |
| 298 | 1 | 3,5-diOMe-Ph | FA: 521 |
| 299 | 1 | 3-Ac-Ph | FA: 503 |
| 322 | 1 | 5,6-diCl-3Py | FA: 530 |

TABLE 30

(1)

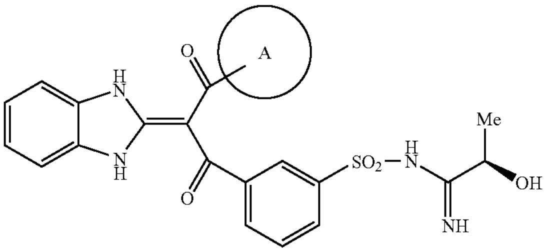

| Ex | Syn | A | Dat |
|---|---|---|---|
| 300 | 1 | 1Naph | FA: 541; N1: 1.20 (3H, d, J = 6.4 Hz), 4.04-4.16 (1H, m), 5.87 (1H, d, J = 5.2 Hz), 6.53-6.65(1H, m), 7.05-7.60 (10H, m), 7.64-7.71 (1H, m), 7.73-7.83 (2H, m), 7.94 (1H, br), 8.10-8.22 (2H, m), 13.26 (2H, s) |
| 301 | 1 | 3-Me-Ph | ES+: 505; N1: 1.21 (3H, d, J = 6.8 Hz), 2.11 (3H, s), 4.05-4.18 (1H, m), 5.85 (1H, d, J = 4.8 Hz), 6.81-6.97 (2H, m), 7.00-7.56 (7H, m), 7.66-7.79 (3H, m), 8.02 (1H, br), 8.17 (1H, br), 13.12 (2H, s) |
| 302 | 1 | 3-F-Ph | ES+: 509; N1: 1.21 (3H, d, J = 6.6 Hz), 4.06-4.17 (1H, m), 5.86 (1H, d, J = 5.3 Hz), 6.84-6.96 (1H, m), 6.99-7.12 (3H, m), 7.20-7.37 (3H, m), 7.45-7.61 (2H, m), 7.68-7.80 (3H, m), 8.03 (1H, br), 8.18 (1H, br), 13.12 (2H, s) |
| 303 | 1 | 3-Cl-Ph | FA: 525; N1: 1.21 (3H, d, J = 6.0 Hz), 4.07-4.18 (1H, m), 5.86 (1H, d, J = 4.8 Hz), 7.00-7.36 (7H, m), 7.42-7.62 (2H, m), 7.67-7.80 (3H, m), 8.03 (1H, br), 8.19 (1H, br), 13.12 (2H, s) |
| 304 | 1 | 3,4,5-triF-Ph | FA: 545; N1: 1.20 (3H, d, J = 6.4 Hz), 4.05-4.17 (1H, m), 5.85 (1H, d, J = 4.4 Hz), 7.08-7.20 (2H, m), 7.28-7.40 (3H, m), 7.51-7.59 (1H, m), 7.62-7.70 (2H, m), 7.72-7.82 (2H, m), 8.09 (1H, br), 8.16 (1H, br), 13.17 (2H, s) |
| 305 | 1 | 2,5-diF-Ph | FA: 527; N1: 1.23 (3H, d, J = 6.8 Hz), 4.07-4.20 (1H, m), 5.87 (1H, d, J = 4.8 Hz), 6.67-6.79 (1H, m), 6.84-7.08 (2H, m), 7.22-7.40 (3H, m), 7.46-7.66 (2H, m), 7.68-7.72 (3H, m), 8.04 (1H, br), 8.20 (1H, br), 13.22 (2H, s) |

(2)

| Ex | Syn | A | Dat |
|---|---|---|---|
| 306 | 1 | Ph | FA: 491 |
| 307 | 1 | 2-Me-5-F-Ph | FA: 523 |
| 308 | 1 | 3,4-diMe-Ph | FA: 519 |
| 309 | 1 | 2Naph | ES+: 541 |
| 310 | 1 | 2-Cl-Ph | FA: 525 |
| 311 | 1 | 2,3-diF-Ph | FA: 527 |
| 312 | 1 | 4-F-Ph | FA: 509 |
| 313 | 1 | 3-Cl-4-OMe-Ph | FA: 555 |
| 314 | 1 | 5,6-diCl-3Py | FA: 560 |
| 317 | 1 | 3,5-diOMe-Ph | FA: 551 |
| 318 | 1 | 2-F-Ph | FA: 509 |
| 319 | 1 | 4-Me-Ph | FA: 505 |
| 320 | 1 | 4-Cl-Ph | ES+: 525 |
| 321 | 1 | 6-Cl-3Py | FA: 526 |
| 323 | 1 | 2-Me-Ph | FA: 505 |
| 324 | 1 | 3-Cl-4Py | FA: 526 |
| 325 | 1 | 2-Cl-4,5-diF-Ph | FA: 561 |
| 326 | 1 | 2-Cl-5-F-Ph | FA: 543 |

TABLE 31

| | | | |
|---|---|---|---|
| 315 | 1 | 3-F-4-Me-Ph | FA: 523 |
| 316 | 1 | 5-F-2-OMe-Ph | FA: 539 |
| 327 | 1 | 5-Cl-2-OMe-Ph | FA: 555 |
| 328 | 1 | 3-Cl-2-Me-Ph | FA: 539 |

TABLE 32

(1)

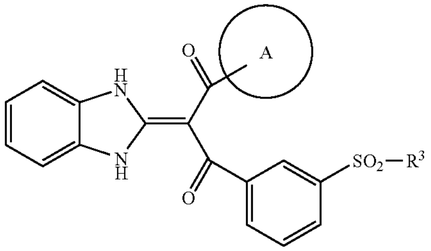

| Ex | Syn | A | $R^3$ | Dat |
|---|---|---|---|---|
| 329 | 1 | 3-F-Ph | —NH—C(═NH)-iPr | FA: 507; N1: 1.01 (6H, d, J = 7.3 Hz), 2.45-2.55 (1H, m), 6.85-6.95 (1H, m), 6.99-7.13 (3H, m), 7.20-7.33 (3H, m), 7.42-7.60 (2H, m), 7.70-7.80 (3H, m), 7.85 (1H, br), 8.57 (1H, br), 13.12 (2H, s) |
| 330 | 1 | 4-OMe-Ph | —NH—C(═NH)-Me | FA: 491; N1: 1.99 (3H, s), 3.63 (3H, s), 6.52- 6.65 (2H, m), 7.18-7.37 (3H, m), 7.43-7.56 (2H, m), 7.64-7.77 (3H, m), 8.14 (1H, br), 8.50 (1H, br), 13.06 (2H, s) |
| 331 | 1 | 4-Cl-Ph | —NH—C—(═NH)-Me | FA: 495; N1: 2.01 (3H, s), 7.05-7.11 (2H, m), 7.20-7.35 (5H, m), 7.44-7.50 (1H, m), 7.53-7.59 (1H, m), 7.65-7.79 (3H, m), 8.15 (1H, br), 8.54 (1H, br), 13.12 (2H, s) |
| 332 | 1 | 3-Cl-4-F-Ph | —NH—C(═NH)-Me | FA: 513; N1: 2.02 (3H, s), 6.97-7.10 (1H, m), 7.20-7.43 (5H, m), 7.45-7.81 (5H, m), 8.10 (1H, br), 8.51 (1H, br), 13.14 (2H, s) |
| 333 | 1 | 4-Me-Ph | —NH—C(═NH)-Me | FA: 475; N1: 1.99 (3H, s), 2.12 (3H, s), 6.85 (2H, d, J = 8.3 Hz), 7.15-7.35 (5H, m), 7.43-7.55 (2H, m), 7.67-7.77 (3H, m), 8.15 (1H, br), 8.52 (1H, br), 13.09 (2H, s) |
| 334 | 3 | 2,5-diF-Ph | —$NH(CH_2)_2OH$ | FA: 500; N1: 2.61-2.74 (2H, m), 3.34-3.44 (2H, m), 4.71 (1H, t, J = 5.6 Hz), 6.72-6.84 (1H, m), 6.85-6.99 (1H, m), 7.00-7.14 (1H, m), 7.25-7.40 (3H, m), |

TABLE 32-continued (1)

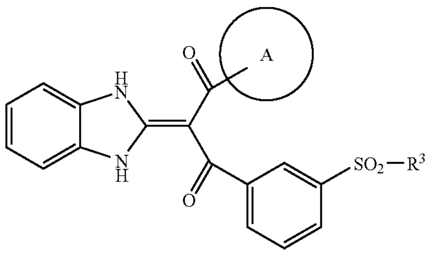

| Ex | Syn | A | $R^3$ | Dat |
|---|---|---|---|---|
| | | | | 7.46-7.66 (3H, m), 7.68-7.82 (3H, m), 13.22 (2H, s) |
| 335 | 3 | 3,4,5-triF-Ph | $—NH(CH_2)_2OH$ | FA: 518; N1: 2.60-2.72 (2H, m), 3.16-3.48 (2H, m), 4.71 (1H, br), 7.14-7.46 (5H, m), 7.53-7.82 (6H, m), 13.17 (2H, s) |

TABLE 32-continued (1)

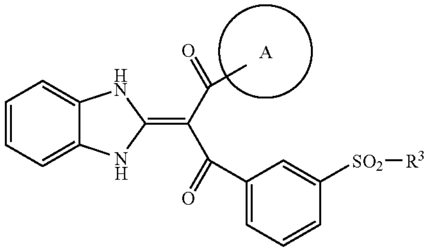

TABLE 33

| | | | | |
|---|---|---|---|---|
| 336 | 1 | 1Naph | —NH—C(═NH)-Me | FA: 511; N1: 1.97 (3H, s), 6.60 (1H, t, J = 7.8 Hz), 7.07-7.20 (3H, m), 7.25-7.38 (3H, m), 7.40-7.57 (4H, m), 7.65-7.71 (1H, m), 7.75-7.82 (2H, m), 8.04 (1H, br), 8.18 (1H, d, J = 8.3 Hz), 8.47 (1H, br), 13.26 (2H, s) |
| 337 | 1 | 3-F-Ph | $—N{=}C(NH_2)_2$ | ES+: 480; N1: 6.72 (4H, br), 6.85-6.94 (1H, m), 6.99-7.12 (3H, m), 7.17-7.24 (1H, m), 7.27-7.35 (2H, m), 7.39-7.44 (1H, m), 7.47-7.53 (1H, m), 7.63-7.67 (1H, m), 7.72-7.79 (2H, m), 13.11 (2H, s) |
| 338 | 16 | 3,5-diF-Ph | 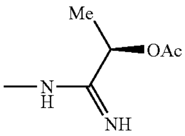 | ES+: 569; N1: 1.32 (3H, d, J = 6.8 Hz), 2.02 (3H, s), 4.96-5.08 (1H, m), 6.67-6.81 (1H, m), 6.86-7.09 (2H, m), 7.22-7.42 (3H, m), 7.48-7.64 (2H, m), 7.70-7.84 (3H, m), 8.09 (1H, br), 8.70 (1H, br), 13.22 (2H, s) |
| 339 | 1 | 1Naph | $—N{=}C(NH_2)_2$ | FA: 512; N1: 6.45-6.56 (1H, m), 6.69 (4H, br), 6.96 (1H, d, J = 7.8 Hz), 7.06-7.18 (2H, m), 7.20-7.60 (7H, m), 7.64-7.83 (3H, m), 8.16 (1H, d, J = 8.8 Hz), 13.26 (2H, s) |
| 340 | 16 | 3-Cl-Ph | $—NH(CH_2)_2OH$ | FA: 567: N1: 1.31 (3H, d, J = 6.8 Hz), 2.01 (3H, s), 4.95-5.07 (1H, m), 7.00-7.38 (7H, m), 7.45-7.60 (2H, m), 7.65-7.80 (3H, m), 8.07 (1H, br), 8.69 (1H, br), 13.13 (2H, s) |

(2)

| Ex | Syn | A | $R^3$ | Dat |
|---|---|---|---|---|
| 18 | 18 | $3\text{-}SO_2Me\text{-}Ph$ | —NH—C(═NH)-Me | ES+: 539 |
| 341 | 3 | Ph | $—NH_2$ | FA: 420 |
| 342 | 3 | 3-Cl-Ph | $—NH_2$ | FA: 454 |
| 343 | 1 | Ph | $—N{=}C(NH_2)_2$ | FA: 462 |
| 344 | 1 | Ph | —NH—C(═NH)-iPr | FA: 489 |
| 345 | 3 | Ph | $—NH(CH_2)_2OH$ | FA: 464 |
| 346 | 1 | $3\text{-}CF_3\text{-}Ph$ | $—N{=}C(NH_2)_2$ | FA: 530 |
| 347 | 1 | 3-Br-Ph | $—N{=}C(NH_2)_2$ | ES+: 540 |
| 348 | 3 | 3,5-diF-Ph | —NHOBn | FA: 562 |
| 349 | 1 | 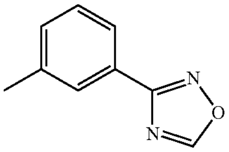 | —NH—C(═NH)-iPr | FA: 557 |
| 350 | 3 | | $—NH_2$ | ES+: 488 |

TABLE 33-continued

| | | | | |
|---|---|---|---|---|
| 351 | 3 | 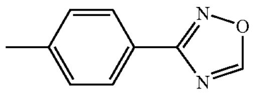 | —NH(CH$_2$)$_2$OH | FA: 532 |
| 352 | 3 | 2-Cl-Ph | —NH(CH$_2$)$_2$OH | FA: 498 |

TABLE 34

| | | | | |
|---|---|---|---|---|
| 353 | 3 | 2-F-Ph | —NH(CH$_2$)$_2$OH | FA: 482 |
| 354 | 3 | 3-Cl-Ph | —NH(CH$_2$)$_2$OH | FA: 498 |
| 355 | 3 | 3-Me-Ph | —NH(CH$_2$)$_2$OH | ES+: 478 |
| 356 | 3 | 2-Me-3-F-Ph | —NH(CH$_2$)$_2$OH | FA: 496 |
| 357 | 3 | 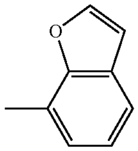 | —NH(CH$_2$)$_2$OH | FA: 504 |
| 358 | 3 | 4-F-1Naph | —NH(CH$_2$)$_2$OH | FA: 532 |
| 359 | 1 | 3-Cl-Ph | —NH—C(=NH)—CH(OH)-Et | FA: 539 |
| 360 | 1 | 2,3-diMe-Ph | —N=C(NH$_2$)$_2$ | FA: 490 |
| 361 | 1 | 3,4-diMe-Ph | —N=C(NH$_2$)$_2$ | FA: 490 |
| 362 | 1 | 2-CF$_3$-Ph | —N=C(NH$_2$)$_2$ | FA: 530 |
| 363 | 1 | 4-CF$_3$-Ph | —N=C(NH$_2$)$_2$ | FA: 530 |
| 364 | 1 | Ph | 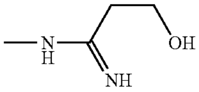 | FA: 491 |
| 365 | 1 | 3-Me-Ph | 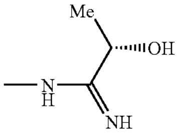 | FA: 505 |
| 366 | 1 | Ph | | FA: 491 |
| 367 | 4 | Ph | —NH-(2-Py) | FA: 497 |
| 368 | 4 | 2-Cl-Ph | —NH-(2-Py) | FA: 531 |
| 369 | 4 | 2-F-Ph | —NH-(2-Py) | FA: 515 |
| 370 | 1 | 3,4-diCl-Ph | —N=C(NH$_2$)$_2$ | FA: 530 |
| 371 | 1 | 3,5-diCl-Ph | —N=C(NH$_2$)$_2$ | FA: 530 |
| 372 | 1 | 3,4-diF-Ph | —N=C(NH$_2$)$_2$ | FA: 498 |
| 373 | 1 | 2,3-diF-Ph | —N=C(NH$_2$)$_2$ | FA: 498 |
| 374 | 1 | 2,3-diCl-Ph | —N=C(NH$_2$)$_2$ | FA: 530 |
| 375 | 1 | 2,5-diCl-Ph | —N=C(NH$_2$)$_2$ | FN: 528 |
| 376 | 1 | 2Naph | —N=C(NH$_2$)$_2$ | FA: 512 |
| 377 | 1 | 3-Me-Ph | —NH—C(=NH)—CH(OH)-Me | FA: 505 |
| 378 | 12 | 3-Me-Ph | —NH—C(=NH)-Ac | FA: 503 |
| 379 | 4 | 3-Cl-Ph | —NH-(2Py) | ES+: 531 |
| 380 | 1 | 2-Cl-Ph | —NH—C(=NH)-iPr | FA: 523 |
| 381 | 1 | 2-Cl-Ph | —NH—C(=NH)-cPr | FA: 521 |
| 382 | 1 | 2-F-Ph | —NH—C(=NH)-iPr | ES+: 507 |
| 383 | 1 | 2-OMe-Ph | —NH—C(=NH)-iPr | ES+: 519 |

TABLE 35

| | | | | |
|---|---|---|---|---|
| 384 | 3 | 2-Cl-4,5-diF-Ph | —NH(CH$_2$)$_2$OH | FA: 534 |
| 385 | 3 | 2-Cl-4,5-diF-Ph | —NH(CH$_2$)$_3$OH | FA: 548 |
| 386 | 3 | 3-F-4-OMe-Ph | —NH(CH$_2$)$_2$OH | ES+: 512 |
| 387 | 3 | 3-F-4-OMe-Ph | —NH(CH$_2$)$_3$OH | FA: 526 |
| 388 | 1 | 3-F-4-Me-Ph | —NH(CH$_2$)$_2$OH | FA: 496 |
| 389 | 3 | 3-F-4-Me-Ph | —NH(CH$_2$)$_3$OH | FA: 510 |

TABLE 35-continued

| | | | | |
|---|---|---|---|---|
| 390 | 3 | 2-Cl-3-F-Ph | —NH(CH$_2$)$_2$OH | FA: 516 |
| 391 | 3 | 3-Cl-5-F-Ph | —NH(CH$_2$)$_2$OH | FA: 516 |
| 392 | 3 | 2-Cl-5-F-Ph | —NH(CH$_2$)$_2$OH | FA: 516 |
| 393 | 3 | 2-Cl-5-F-Ph | —NH(CH$_2$)$_3$OH | FA: 530 |
| 394 | 3 | 5-F-2-OMe-Ph | —NH(CH$_2$)$_2$OH | FA: 512 |
| 395 | 3 | 5-F-2-OMe-Ph | —NH(CH$_2$)$_3$OH | FA: 526 |
| 396 | 3 | 5-Cl-2-OMe-Ph | —NH(CH$_2$)$_2$OH | FA: 528 |
| 397 | 3 | 5-Cl-2-OMe-Ph | —NH(CH$_2$)$_3$OH | FA: 542 |
| 398 | 3 | 3-Cl-4-OMe-Ph | —NH(CH$_2$)$_2$OH | FN: 526 |
| 399 | 3 | 3-Cl-4-OMe-Ph | —NH(CH$_2$)$_3$OH | FA: 540 |
| 400 | 3 | 3-Cl-2-Me-Ph | —NH(CH$_2$)$_2$OH | FA: 512 |
| 401 | 3 | 3-Cl-2-Me-Ph | —NH(CH$_2$)$_3$OH | FA: 526 |
| 402 | 1 | 3-Cl-Ph | —NH—C(=NH)—(CH$_2$)$_2$OH | FA: 525 |
| 403 | 3 | 3,5-diOMe-Ph | —NH(CH$_2$)$_2$OH | FA: 524 |
| 404 | 3 | 3,5-diOMe-Ph | —NH(CH$_2$)$_3$OH | FN: 536 |
| 405 | 3 | 3-SMe-Ph | —NH(CH$_2$)$_2$OH | FA: 510 |
| 406 | 3 | 3-Ac-Ph | —NH(CH$_2$)$_2$OH | FA: 506 |
| 407 | 3 | 3-Cl-Ph | —NH(CH$_2$)$_3$OH | FA: 512 |
| 408 | 3 | 2-F-Ph | —NH(CH$_2$)$_3$OH | ES+: 496 |

TABLE 36

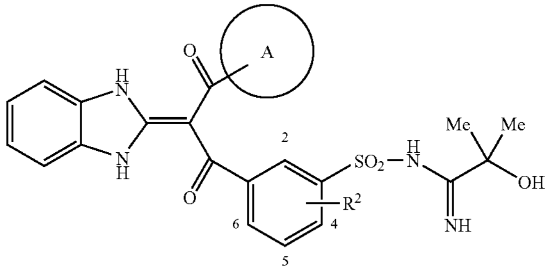

| Ex | Syn | A | R$^2$ | Dat |
|---|---|---|---|---|
| 409 | 1 | 3-F-Ph | 2-Me | FA: 537 |
| 410 | 1 | 3-F-Ph | 4-Me | ES+: 537 |
| 411 | 1 | 3-F-Ph | 6-Me | FA: 537 |
| 412 | 1 | 3,4,5-triF-Ph | 2-Me | FA: 573 |
| 413 | 1 | 3-Cl-Ph | 2-Me | FA: 553 |
| 414 | 1 | 3,5-diF-Ph | 2-Me | FA: 555 |
| 415 | 1 | 3,4,5-triF-Ph | 4-Me | FA: 573 |
| 416 | 1 | 1Naph | 4-Me | FA: 569 |
| 417 | 1 | 3-Me-Ph | 4-Me | ES+: 533 |
| 418 | 1 | 3-Me-Ph | 6-Me | FA: 533 |
| 419 | 1 | 3-Me-Ph | 2-Me | FA: 533 |
| 420 | 1 | 3,5-diF-Ph | 4-Me | ES+: 555 |
| 421 | 1 | 3,5-diF-Ph | 6-Me | FA: 555 |
| 422 | 1 | 6-Cl-3-Py | 2-Me | FA: 554 |
| 423 | 1 | 3-Cl-Ph | 4-Me | FA: 553 |
| 424 | 1 | 3-F-Ph | 4-Cl | FA: 557 |

TABLE 37

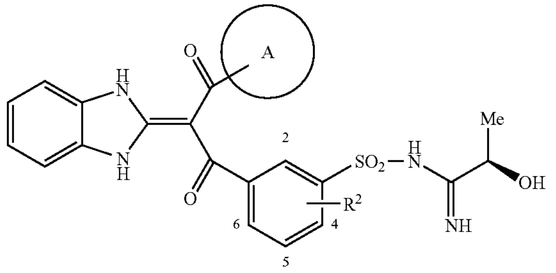

| Ex | Syn | A | $R^2$ | Dat |
|---|---|---|---|---|
| 425 | 1 | Ph | 2-Me | FA: 505 |
| 426 | 1 | 3,4,5-triF-Ph | 2-Me | FA: 559 |
| 427 | 1 | 3-Cl-Ph | 2-Me | FA: 539 |
| 428 | 1 | 3-F-Ph | 4-Me | FA: 523 |
| 429 | 1 | 3-F-Ph | 6-Me | FA: 523 |
| 430 | 1 | 3,5-diF-Ph | 2-Me | FA: 541 |
| 431 | 1 | 3-F-Ph | 2-Me | FA: 523 |
| 432 | 1 | 3-F-Ph | 2-Cl | FA: 543 |
| 433 | 1 | 3,5-diF-Ph | 2-Cl | FA: 561 |
| 434 | 1 | 3-Me-Ph | 2-Cl | ES+: 539 |
| 435 | 1 | 2,5-diF-Ph | 2-Me | ES+: 541 |
| 440 | 1 | 2,3-diF-Ph | 2-Me | FA: 541 |
| 441 | 1 | 3,4-diMe-Ph | 2-Me | ES+: 533 |
| 442 | 1 | 2-Me-5-F-Ph | 2-Me | ES+: 537 |
| 443 | 1 | 3-Me-Ph | 2-Me | ES+: 519 |
| 444 | 1 | 3-Me-Ph | 4-Me | ES+: 519 |
| 445 | 1 | 3,5-diF-Ph | 4-Me | ES+: 541 |
| 446 | 1 | 3,5-diF-Ph | 6-Me | FA: 541 |
| 447 | 1 | 3-Me-Ph | 6-Me | FA: 519 |
| 448 | 1 | 6-Cl-3-Py | 2-Me | FA: 540 |
| 449 | 1 | 2-Cl-Ph | 2-Me | FA: 539 |
| 450 | 1 | 4-Cl-Ph | 2-Me | FA: 539 |

TABLE 38

| | | | | |
|---|---|---|---|---|
| 436 | 1 | 1Naph | 2-Me | FA: 555 |
| 437 | 1 | 2Naph | 2-Me | FA: 555 |
| 438 | 1 | 1Naph | 4-Me | FA: 555 |
| 439 | 1 | 3-F-Ph | 4-Cl | FA: 543 |
| 451 | 1 | 3,4,5-triF-Ph | 4-Me | FA: 559 |
| 452 | 1 | 6-Cl-3-Py | 4-Me | FA: 540 |
| 453 | 1 | 3-Cl-Ph | 4-Me | FA: 539 |

TABLE 39

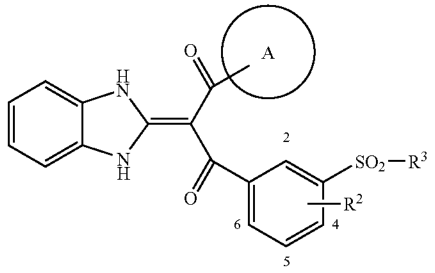

| Ex | Syn | A | $R^2$ | $R^3$ | Dat |
|---|---|---|---|---|---|
| 454 | 3 | 3-F-Ph | 2-Me | —NH$(CH_2)_2$OH | ES+: 496; N1: 2.51 (3H, s), 2.63-2.76 (2H, m), 3.38-3.46 (2H, m), 4.72 (1H, t, J = 5.6 Hz), |

TABLE 39-continued

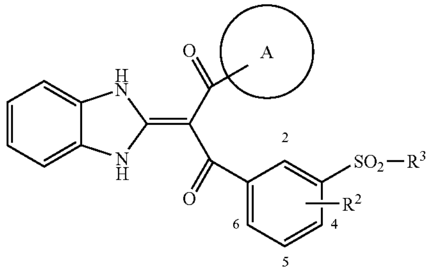

| Ex | Syn | A | $R^2$ | $R^3$ | Dat |
|---|---|---|---|---|---|
| | | | | | 6.83-7.12 (5H, m), 7.20-7.37 (3H, m), 7.47-7.63 (2H, m), 7.71-7.81 (2H, m), 13.23 (2H, s) |
| 455 | 3 | 3-Me-Ph | 2-Me | —NH$(CH_2)_2$OH | ES+: 492 |
| 456 | 3 | 3-F-Ph | 2-Me | —NH$(CH_2)_3$OH | FA: 510; N1: 1.52-1.64 (2H, m), 2.51 (3H, s), 2.64-2.75 (2H, m), 3.38-3.48 (2H, m), 4.46 (1H, t, J = 4.8 Hz), 6.84-7.13 (5H, m), 7.20-7.37 (3H, m), 7.45-7.57 (2H, m), 7.71-7.82 (2H, m), 13.23 (2H, s) |
| 457 | 3 | 3,5-diF-Ph | 2-Me | —NH$(CH_2)_3$OH | FA: 528; N1: 1.50-1.66 (2H, m), 2.50 (3H, s), 2.64-2.84 (2H, m), 3.36-3.46 (2H, m), 4.46 (1H, t, J = 5.0 Hz), 6.79-6.94 (3H, m), 7.13 (1H, t, J = 7.6 Hz), 7.25-7.38 (3H, m), 7.50-7.64 (2H, m), 7.73-7.82 (2H, m), 13.25 (2H, s) |
| 458 | 3 | 3-Cl-Ph | 2-Me | —NH$(CH_2)_2$OH | FA: 512; N1: 2.62-2.82 (2H, m), 3.42 (2H, t, J = 6.4 Hz), 4.71 (1H, br), 6.99-7.41 (8H, |

TABLE 39-continued

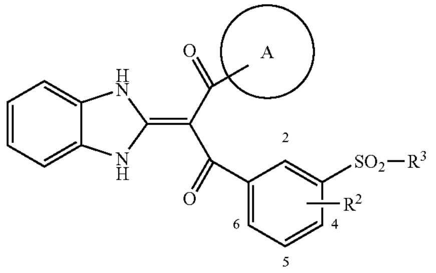

| Ex | Syn | A | $R^2$ | $R^3$ | Dat |
|---|---|---|---|---|---|
| | | | | | m), 7.46-7.65 (2H, m), 7.70-7.85 (2H, m), 13.23 (2H, s) |
| 459 | 1 | Ph | 2-Me | —NH—C(═NH)-Me | FA: 475 |
| 460 | 1 | 3-Cl-Ph | 2-Me | —NH—C(═NH)-Me | FA: 509; N1: 1.97 (3H, s), 2.52 (3H, s), 6.96-7.25 (6H, m), 7.28- |

TABLE 39-continued

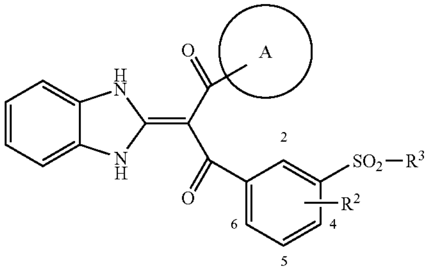

| Ex | Syn | A | $R^2$ | $R^3$ | Dat |
|---|---|---|---|---|---|
| | | | | | 7.37 (2H, m), 7.56-7.64 (1H, m), 7.72-7.81 (2H, m), 8.04 (1H, br), 8.44 (1H, br), 13.19 (2H, s) |
| 461 | 1 | 3-Me-Ph | 2-Me | —NH—C(═NH)-Me | ES+: 489 |
| 462 | 1 | 3,4,5-triF-Ph | 2-Me | —NH—C(═NH)-Me | FA: 529 |

TABLE 40

| | | | | | |
|---|---|---|---|---|---|
| 463 | 3 | 3,4,5-triF-Ph | 2-Me | —$NH(CH_2)_2OH$ | FA: 532 |
| 464 | 3 | 3-F-Ph | 6-Me | —$NH(CH_2)_2OH$ | FA: 496 |
| 465 | 3 | 3-F-Ph | 6-Me | —$NH(CH_2)_3OH$ | FA: 510 |
| 466 | 3 | 3,5-diF-Ph | 6-Me | —$NH(CH_2)_2OH$ | FA: 514 |
| 467 | 14 | 3,5-diF-Ph | 4-Cl | —$N(Me)_2$ | FA: 518; N1: 2.76 (6H, s), 6.94-7.12 (3H, m), 7.28-7.39 (2H, m), 7.47 (1H, d, J = 8.3 Hz), 7.54-7.62 (1H, m), 7.71-7.82 (2H, m), 7.85 (1H, d, J = 1.5 Hz), 13.19 (2H, s) |
| 468 | 14 | 3,5-diF-Ph | 6-OMe | —$N(Me)_2$ | FA: 514 |
| 469 | 1 | 3,5-diF-Ph | 6-OMe | —NH—C(═NH)-Me | FA: 527; N1: 2.01 (3H, s), 3.73 (3H, s), 6.72-6.83 (3H, m), 6.90-7.00 (1H, m), 7.27-7.36 (2H, m), 7.41 (1H, d, J = 2.5 Hz), 7.52 (1H, dd, J = 8.8 Hz, 2.4 Hz), 7.72-7.80 (2H, m), 7.99 (1H, br), 8.44 (1H, br), 13.17 (2H, s) |
| 470 | 3 | 3,5-diF-Ph | 2-Me | —$NH(CH_2)_2OH$ | ES+: 514; N1: 2.49 (3H, s), 2.68-2.84 (2H, m), 3.37-3.45 (2H, m), 4.72 (1H, t, J = 5.6 Hz), 6.78-6.92 (3H, m), 7.08-7.16 (1H, m), 7.25-7.38 (3H, m), 7.52-7.60 (1H, m), 7.62-7.68 (1H, m), 7.73-7.82 (2H, m), 13.24 (2H, s) |
| 471 | 3 | 3,5-diF-Ph | 6-Me | —$NH(CH_2)_3OH$ | FA: 528 |
| 472 | 1 | 3,5-diF-Ph | 2-Me | —NH—C(═NH)-Me | FA: 511; N1: 2.00 (3H, s), 2.51 (3H, s), 6.77-6.92 (3H, s), 7.05-7.14 (1H, m), 7.20-7.38 (3H, m), 7.62-7.69 (1H, m), 7.72-7.82 (2H, m), 8.00 (1H, br), 8.45 (1H, br), 13.21 (2H, s) |
| 473 | 1 | 3-F-Ph | 2-Cl | —NH—C(═NH)-Me | FA: 531 |
| 474 | 1 | 3-Me-Ph | 2-Cl | —NH—C(═NH)-Me | ES+: 509 |
| 475 | 1 | 1Naph | 2-Me | —NH—C(═NH)-Me | FA: 525; N1: 1.90 (3H, s), 2.45 (3H, br), 6.28 (1H, br), 6.94-7.19 (3H, m), 7.23-7.72 (7H, m), 7.75-7.85 (2H, m), 8.01 (2H, br), 8.44 (1H, br), 13.40 (2H, s) |
| 476 | 1 | 2Naph | 2-Me | —NH—C(═NH)-Me | FA: 525 |
| 477 | 1 | 2,5-diF-Ph | 2-Me | —NH—C(═NH)-Me | ES+: 511 |
| 478 | 1 | 2,3-diF-Ph | 2-Me | —NH—C(═NH)-Me | ES+: 511 |
| 479 | 1 | 2-Me-5-F-Ph | 2-Me | —NH—C(═NH)-Me | FA: 507 |
| 480 | 1 | 3,4-diMe-Ph | 2-Me | —NH—C(═NH)-Me | ES+: 503 |
| 481 | 1 | 3-F-Ph | 4-Cl | —NH—C(═NH)-Me | FA: 513 |
| 482 | 1 | 3-F-Ph | 4-F | —NH—C(═NH)-Me | FA: 497 |
| 483 | 2 | 3-F-Ph | 2-Me | —NH—C(═NH)-Me | FA: 493 |
| 484 | 2 | 3-F-Ph | 4-Me | —NH—C(═NH)-Me | FA: 493 |

TABLE 41

| | | | | | |
|---|---|---|---|---|---|
| 485 | 2 | 3-F-Ph | 6-Me | —NH—C(=NH)-Me | FA: 493 |
| 486 | 2 | 3-F-Ph | 2-Cl | —NH—C(=NH)-Me | ES+: 513 |
| 487 | 1 | 3,5-diF-Ph | 4-Me | —NH—C(=NH)-Me | ES+: 511 |
| 488 | 1 | 3-Me-Ph | 4-Me | —H—(=NH)-Me | ES+: 489 |
| 489 | 1 | 3,5-diF-Ph | 6-Me | —NH—C(=NH)-Me | FA: 511 |
| 490 | 1 | 3-Me-Ph | 6-Me | —NH—C(=NH)-Me | FA: 489 |
| 491 | 1 | 4-Cl-Ph | 2-Me | —NH—C(=NH)-Me | FA: 509 |
| 492 | 1 | 2-Cl-Ph | 2-Me | —NH—C(=NH)-Me | FA: 509 |
| 493 | 1 | 6-Cl-3-Py | 2-Me | —NH—C(=NH)-Me | FA: 510 |
| 494 | 1 | 3,4,5-triF-Ph | 4-Me | —NH—C(=NH)-Me | FA: 529 |
| 495 | 1 | 3-Cl-Ph | 4-Me | —NH—C(=NH)-Me | FA: 509 |
| 496 | 3 | 3,5-diF-Ph | 4-Me | —NH—$(CH_2)_2$OH | FA: 514 |
| 497 | 3 | 3,5-diF-Ph | 4-Me | —NH—$(CH_2)_3$OH | FA: 528 |
| 498 | 3 | 3-F-Ph | 4-Me | —NH$(CH_2)_2$OH | FA: 496 |
| 499 | 3 | 3-F-Ph | 4-Me | —NH$(CH_2)_3$OH | FA: 510 |
| 500 | 3 | 3-F-Ph | 4-Cl | —NH—$(CH_2)_2$OH | FA: 516 |
| 501 | 3 | 3-F-Ph | 4-Cl | —NH—$(CH_2)_3$OH | FA: 530 |

TABLE 41-continued

| | | | | | |
|---|---|---|---|---|---|
| 502 | 3 | 3,5-diF-Ph | 2-Me | 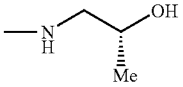 | FA: 528 |
| 503 | 3 | 3-F-Ph | 2-Me | | FA: 510; N1: 1.04 (3H, d, J = 6.4 Hz), 2.46-2.66 (2H, m), 3.54-3.71 (1H, m), 4.70 (1H, br), 6.82-7.12 (5H, m), 7.19-7.37 (3H, m), 7.44-7.62 (2H, m), 7.72-7.80 (2H, m), 13.23 (2H, s) |
| 504 | 3 | 3,5-diF-Ph | 2-Me | 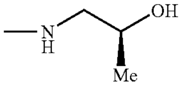 | FA: 528 |
| 505 | 3 | 3-F-Ph | 2-Me | | FA: 510 |
| 506 | 3 | 3-Me-Ph | 2-Me | —NH—$(CH_2)_3$OH | FA: 506 |
| 507 | 14 | 3,5-diF-Ph | | 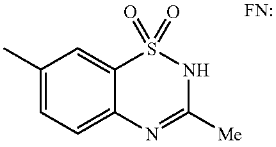 | FN: 493 |

TABLE 42

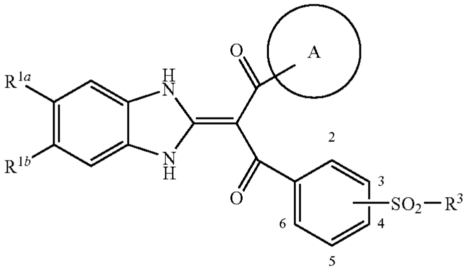

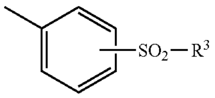

| Ex | Syn | A | $R^{1a}$ | $R^{1b}$ | pos | $R^3$ | Dat |
|---|---|---|---|---|---|---|---|
| 17 | 17 | 3,5-diF-Ph | $H_2N$ | H | 3 | —NH—C(=NH)-Me | FA: 512 |
| 508 | 3 | 3,5-diF-Ph | H | H | 4 | —$NH_2$ | FA: 456 |
| 509 | 1 | 3,5-diF-Ph | Me | Me | 3 | —N=C$(NH_2)_2$ | FA: 526; N1: 2.33 (6H, s), 6.69 (4H, br), 6.84-6.96 (3H, m), 7.27 (1H, t, J = 7.8 Hz), 7.44-7.57 (4H, m), 7.61-7.65 (1H, m), 12.97 (2H, s) |
| 510 | 1 | 3-F-Ph | F | F | 3 | —N=C$(NH_2)_2$ | FA: 516; N1: 6.70 (4H, br), 6.84-6.94 (1H, m), 6.96-7.12 (3H, m), 7.14-7.24 (1H, m), 7.36-7.53 (2H, m), 7.60-7.78 (3H, m), 13.20 (2H, s) |
| 511 | 1 | 3,5-diF-Ph | F | H | 3 | —N=C$(NH_2)_2$ | FA: 516 |
| 512 | 1 | 3,5-diF-Ph | Cl | H | 3 | —N=C$(NH_2)_2$ | FA: 532 |
| 513 | 1 | 3,5-diF-Ph | Me | H | 3 | —N=C$(NH_2)_2$ | FA: 512 |
| 514 | 1 | 3-F-Ph | F | H | 3 | 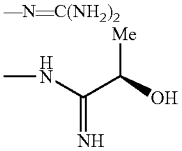 | FA: 527 |
| 515 | 1 | 3,5-diF-Ph | F | H | 3 | | ES+: 545 |

TABLE 42-continued

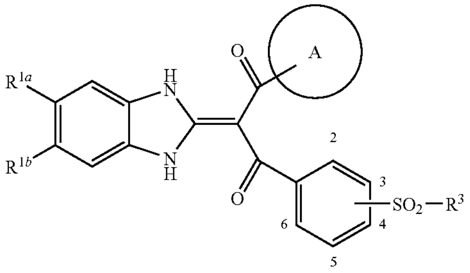

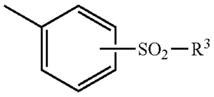

| Ex | Syn | A | $R^{1a}$ | $R^{1b}$ | pos | $R^3$ | Dat |
|---|---|---|---|---|---|---|---|
| 516 | 1 | 3,5-diF-Ph | F | H | 3 | 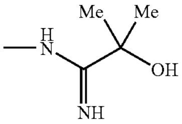 | FA: 559 |
| 517 | 1 | 3-F-Ph | F | H | 3 | | FA: 541 |
| 518 | 1 | 3,5-diF-Ph | F | H | 3 | —NH—C(═NH)-Me | FA: 515 |
| 519 | 1 | 3-F-Ph | F | H | 3 | —NH—C(═NH)-Me | FA: 497 |
| 520 | 1 | Ph | Bn-S | H | 3 | —NH—C(═NH)-Me | FA: 583 |
| 521 | 1 | 3-F-Ph | PhCO | H | 3 | —NH—C(═NH)-Me | FA: 583 |
| 522 | 1 | 3-F-Ph | MeO | MeO | 3 | —NH—C(═NH)-Me | FA: 539 |

TABLE 43

| | | | | | | | |
|---|---|---|---|---|---|---|---|
| 523 | 1 | 3,5-diF-Ph | $O_2N$ | H | 3 | —NH—C(═NH)-Me | FN: 540 |
| 524 | 3 | 3-F-Ph | MeO | MeO | 3 | —NH—$(CH_2)_2$OH | FA: 542 |
| 525 | 3 | 3,5-diF-Ph | $O_2N$ | H | 3 | —NH—$(CH_2)_2$OH | FA: 545 |
| 526 | 9 | 3,5-diF-Ph | (4-(AcNH)-Ph)-CONH— | H | 3 | —NH—C(═NH)-Me | FA: 673 |
| 527 | 17 | 3,5-diF-Ph | $H_2N$ | H | 3 | —NH—$(CH_2)_2$OH | FA: 515 |
| 528 | 1 | 3,5-diF-Ph | H | H | 4 | —NH—C(═NH)-Me | ES+: 497 |
| 529 | 3 | 3,5-diF-Ph | H | H | 4 | —NH—$(CH_2)_2$OH | FA: 500 |
| 530 | 3 | 3,5-diF-Ph | H | H | 4 | —NH—$(CH_2)_3$OH | FA: 514 |

TABLE 44

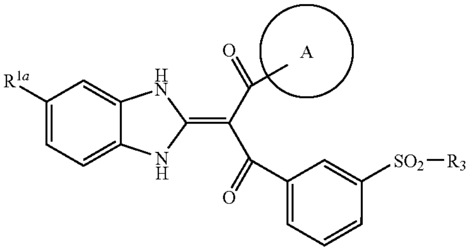

| Ex | Syn | A | $R^{1a}$ | $R^3$ | Dat |
|---|---|---|---|---|---|
| 534 | 16 | 3-F-Ph | H | 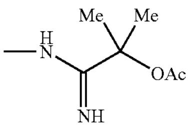 | 565: FA |

TABLE 44-continued

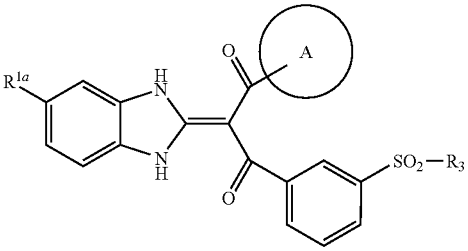

| Ex | Syn | A | $R^{1a}$ | $R^3$ | Dat |
|---|---|---|---|---|---|
| 535 | 1 | | | 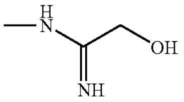 | 495: FA |

TABLE 44-continued

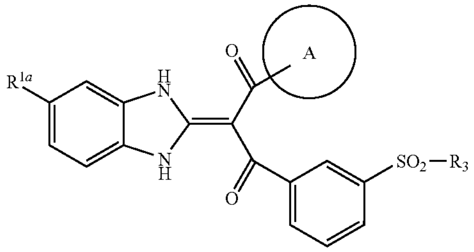

| Ex | Syn | A | $R^{1a}$ | $R^3$ | Dat |
|---|---|---|---|---|---|
| 536 | 16 | | | 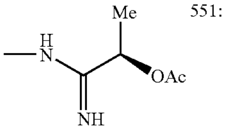 | 551: FA |
| 537 | 2 | | | —$NH(CH_2)_4OH$ | 510: ES+ |
| 538 | 2 | 3,5-diF-Ph | H | 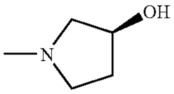 | 526: ES+ |
| 539 | 1 | 3-F-Ph | $CO_2Bn$ | 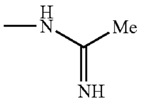 | 613: FA |
| 540 | 11 | | $CO_2H$ | 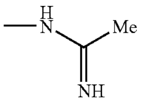 | 521: FN |

TABLE 45

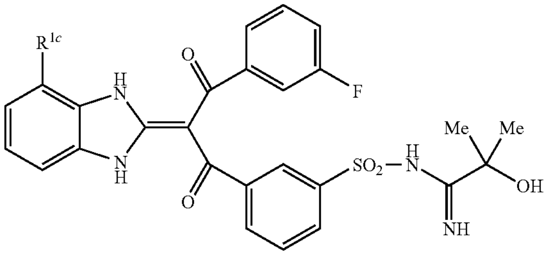

| Ex | Syn | $R^{1c}$ | Dat |
|---|---|---|---|
| 541 | 532 | Me | 537: FA |
| 542 | 532 | Cl | 557: FA |
| 543 | 532 | 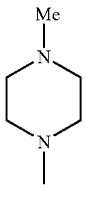 | 621: FA |
| 544 | 532 | —$CH_2OH$ | 553: FA |
| 545 | 532 | —$CO_2Bn$ | 657: FA |
| 546 | 11 | —$CO_2H$ | 567: ES+ |
| 547 | 9 | —$CONH_2$ | 566: FA |

TABLE 45-continued

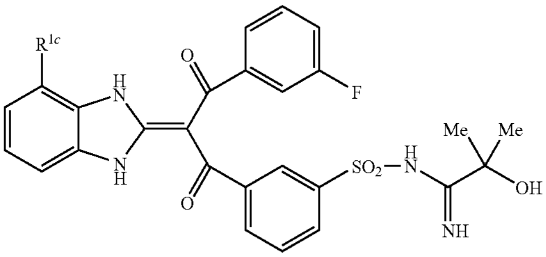

| Ex | Syn | $R^{1c}$ | Dat |
|---|---|---|---|
| 548 | 9 | 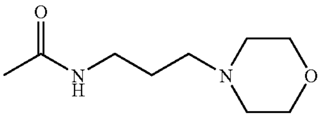 | 693: FA |

TABLE 46

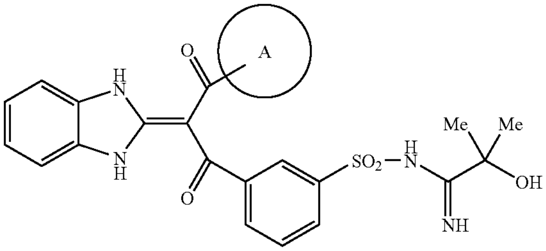

| Ex | Syn | A | Dat |
|---|---|---|---|
| 549 | 1 | 2-Cl-6-OMe-4Py | 570: FA |
| 550 | 1 | 2,4-diCl-5-F-Ph | 591: FA |
| 551 | 1 | 3-Cl-4,5-diF-Ph | 575: FA |
| 552 | 1 | 2-F-3-Cl-Ph | 557: FA |
| 553 | 1 | 3-F-5-Me-Ph | 537: FA |
| 554 | 1 | 2-F-5-Cl-Ph | 557: FA |
| 555 | 1 | 3-Cl-4-Me-Ph | 553: FA |
| 556 | 1 | 2-Me-5-Cl-Ph | 553: FA |
| 557 | 19 | 5-Cl-3-Py | 540: FA |
| 558 | 19 | 3Py | 506: FA |
| 559 | 1 | 2,4,5-triF-Ph | 559: FA |
| 560 | 1 | 2-Cl-6-Me-4Py | 554: FA |
| 561 | 19 | 2-Me-4Py | 520: FA |
| 562 | 1 | 2,5-diF-4-Cl-Ph | 575: FA |
| 563 | 1 | 2,5-diCl-4Py | 574: FA |
| 564 | 19 | 2-OMe-4Py | 536: FA |
| 533 | 533 | 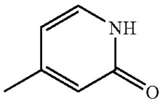 | 522: FA |
| 532 | 532 | 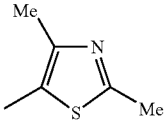 | 540: FA |
| 565 | 532 | 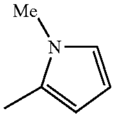 | 508: FA |

TABLE 46-continued

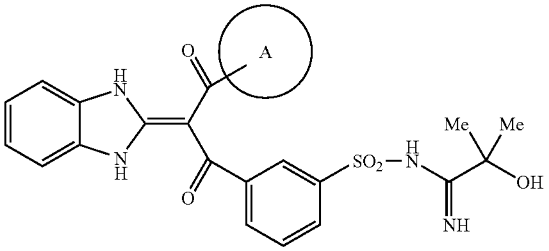

| Ex | Syn | A | Dat |
|---|---|---|---|
| 566 | 532 | 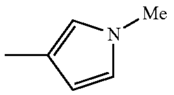 | 508: ES+ |
| 567 | 19 | 3-Cl-4Py | 540: FA |
| 568 | 19 | 4Py | 506: FA |
| 569 | 1 | 2,6-diCl-5-F-3Py | 592: FA |
| 570 | 1 | 2,4-diF-3-Cl-Ph | 575: FA |
| 571 | 1 | 2-Cl-3-F-4Py | 558: FA |
| 572 | 19 | 3-F-4Py | 524: FA |
| 573 | 532 | 2Py | 506: FA |
| 574 | 532 | 3THi | 511: FA |
| 575 | 532 | 2Thi | 511: FA |
| 576 | 532 | 5-Me-2Thi | 525: FA |
| 577 | 532 | 5-Me-2Fur | 509: FA |
| 578 | 532 | 4-Me-2Thi | 525: FA |
| 579 | 532 | 3-Me-2Thi | 525: FA |
| 580 | 1 | 5-Cl-2Thi | 545: FA |
| 581 | 1 | 2,3,4-triF-Ph | 559: FA |
| 582 | 532 | 2,6-diF-3-Me-Ph | 555: FA |
| 583 | 532 | 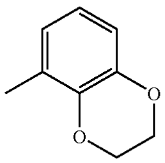 | 563: FA |
| 584 | 532 | 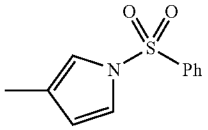 | 634: ES+ |
| 585 | 532 | 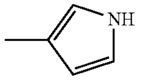 | 494: ES+ |

TABLE 47

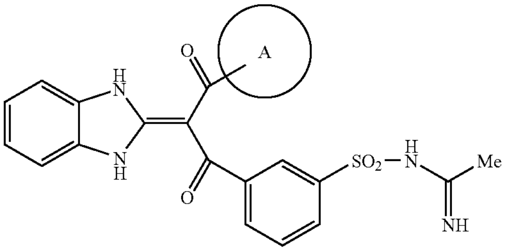

| Ex | Syn | A | Dat |
|---|---|---|---|
| 586 | 1 | 3-$CO_2$Me-Ph | 519: FA |
| 587 | 1 | 3-Cl-4,5-diF-Ph | 531: FA |
| 588 | 1 | 2,4-diCl-5-F-Ph | 547: FA |

TABLE 47-continued

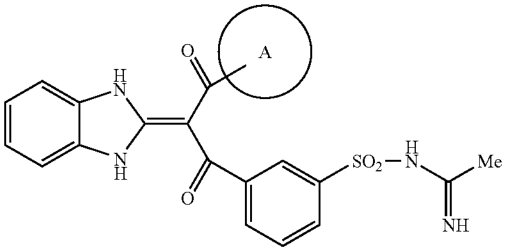

| Ex | Syn | A | Dat |
|---|---|---|---|
| 589 | 1 | 2-F-3-Cl-Ph | 513: FA |
| 590 | 1 | 3-F-5-Me-Ph | 493: FA |
| 591 | 1 | 2-F-5-Cl-Ph | 513: FA |
| 592 | 1 | 3-Cl-4-Me-Ph | 509: FA |
| 593 | 19 | 5-Cl-3Py | 496: FA |
| 594 | 1 | 2-Me-5-Cl-Ph | 509: FA |
| 595 | 1 | 2,4,5-triF-Ph | 515: FA |
| 596 | 1 | 2-Cl-6-Me-4Py | 510: FA |
| 597 | 19 | 2-Me-4Py | 476: FA |
| 598 | 1 | 2-Cl-6-OMe-4Py | 526: FA |
| 599 | 19 | 2-OMe-4Py | 492: FA |
| 600 | 1 | 2,5-diCl-4Py | 530: FA |
| 601 | 1 | 2,5-diF-4-Cl-Ph | 531: FA |

TABLE 48

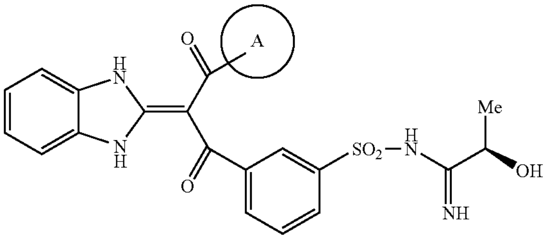

| Ex. | Syn | A | Dat |
|---|---|---|---|
| 602 | 1 | 2-Cl-6-OMe-4Py | 556: FA |
| 603 | 1 | 2,6-diCl-4Py | 560: FA |
| 604 | 1 | 2,4-diCl-5-F-Ph | 577: FA |
| 605 | 1 | 3-Cl-4,5-diF-Ph | 561: FA |
| 606 | 1 | 2-F-3-Cl-Ph | 543: FA |
| 607 | 1 | 2-F-5-Cl-Ph | 543: FA |
| 608 | 1 | 3-Cl-4-Me-Ph | 539: FA |
| 609 | 1 | 3-F-5-Me-Ph | 523: FA |
| 610 | 1 | 2,4,5-triF-Ph | 545: FA |
| 611 | 1 | 2-Me-5-Cl-Ph | 539: FA |
| 612 | 19 | 5-Cl-3-Py | 526: FA |
| 613 | 19 | 3Py | 492: FA |
| 614 | 1 | 2-Cl-6-Me-4Py | 540: FA |
| 615 | 19 | 2-Me-4Py | 506: FA |
| 616 | 1 | 2,5-diF-4-Cl-Ph | 561: FA |
| 617 | 19 | 2-OMe-4Py | 522: FA |
| 618 | 533 | 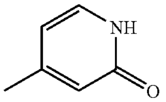 | 508: FA |
| 619 | 1 | 2,5-diCl-4Py | 560: FA |
| 620 | 19 | 3-Cl-4Py | 526: FA |
| 621 | 1 | 2,3,4-triF-Ph | 545: FA |
| 622 | 1 | 6-CN-3Py | 517: FA |
| 623 | 1 | 2,4-diF-3-Cl-Ph | 561: FA |
| 624 | 1 | 2-Cl-3-F-4Py | 544: FA |
| 625 | 19 | 3-F-4Py | 510: FA |

TABLE 48-continued

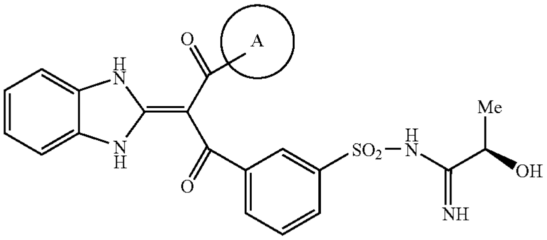

| Ex. | Syn | A | Dat |
|---|---|---|---|
| 626 | 532 | 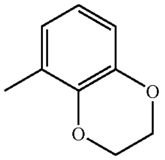 | 549: ES+ |
| 627 | 1 | 5-Cl-2Thi | 533: ES+ |

TABLE 49

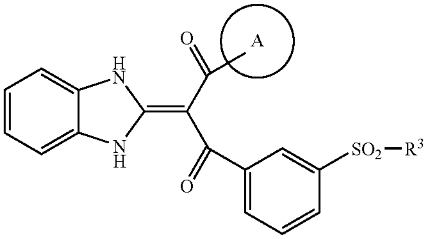

| Ex | Syn | A | $R^3$ | Dat |
|---|---|---|---|---|
| 628 | 2 | 2,5-diF-Ph | $—NH(CH_2)_2OH$ | 500: FA |
| 629 | 2 | 2,4-diCl-5-F-Ph | $—NH(CH_2)_2OH$ | 550: FA |
| 630 | 2 | | $—NH(CH_2)_3OH$ | 564: FA |
| 631 | 2 | 3-Cl-4,5-diF-Ph | $—NH(CH_2)_2OH$ | 534: FA |
| 632 | 2 | | $—NH(CH_2)_3OH$ | 548: FA |
| 633 | 2 | 2-F-3-Cl-Ph | $—NH(CH_2)_2OH$ | 516: FA |
| 634 | 2 | | $—NH(CH_2)_3OH$ | 530: FA |
| 635 | 2 | 3-F-5-Me-Ph | $—NH(CH_2)_3OH$ | 510: FA |
| 636 | 2 | 2-F-5-Cl-Ph | $—NH(CH_2)_2OH$ | 516: FA |
| 637 | 2 | | $—NH(CH_2)_3OH$ | 530: FA |
| 638 | 2 | 3-Cl-4-Me-Ph | $—NH(CH_2)_2OH$ | 512: FA |
| 639 | 2 | | $—NH(CH_2)_3OH$ | 526: FA |
| 640 | 16 | Ph | 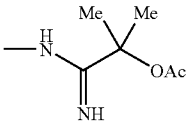 | 547: FA |
| 641 | 16 | 6-Cl-3Py | 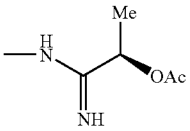 | 566: FN |
| 642 | 2 | | 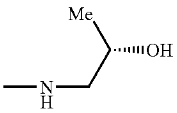 | 513: ES+ |
| 643 | 2 | 2-Me-5-Cl-Ph | $—NH(CH_2)_2OH$ | 512: FA |
| 644 | 2 | 5,6-diCl-3Py | $—NH(CH_2)_2OH$ | 533: ES+ |
| 645 | 19 | 5-Cl-3Py | $—NH(CH_2)_2OH$ | 499: FA |
| 646 | 19 | 3Py | $—NH(CH_2)_2OH$ | 465: FA |

TABLE 49-continued

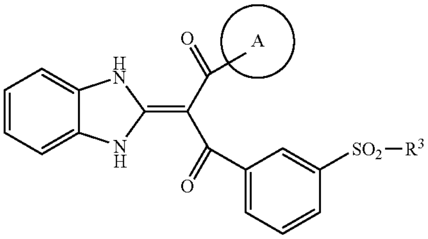

| Ex | Syn | A | $R^3$ | Dat |
|---|---|---|---|---|
| 647 | 2 | 2,3,4-triF-Ph | $—NH(CH_2)_2OH$ | 518: FA |
| 648 | 2 | 2,4,5-triF-Ph | $—NH(CH_2)_2OH$ | 518: ES+ |
| 649 | 2 | 3,4,5-triF-Ph | $—NH(CH_2)_3OH$ | 532: ES+ |

TABLE 50

| | | | | |
|---|---|---|---|---|
| 650 | 2 | 2,5-diF-4-Cl-Ph | $—NH(CH_2)_2OH$ | 534: FA |
| 651 | 19 | 2-Me-4Py | $—NH(CH_2)_2OH$ | 479: FA |
| 652 | 2 | 2-Cl-6-Me-4Py | $—NH(CH_2)_2OH$ | 511: ES− |
| 653 | 2 | 2-Cl-6-OMe-4Py | $—NH(CH_2)_2OH$ | 529: FA |
| 654 | 19 | 2-OMe-4Py | $—NH(CH_2)_2OH$ | 495: FA |
| 655 | 2 | 3-F-4-Me-Ph | 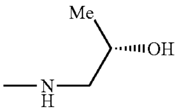 | 510: ES+ |
| 656 | 2 | | 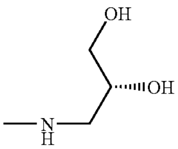 | 526: ES+ |
| 657 | 2 | 2,5-diF-Ph | $—NMe(CH_2)_2OH$ | 514: ES+ |
| 658 | 2 | | 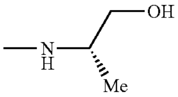 | 514: ES+ |
| 659 | 2 | | 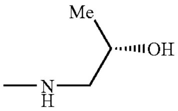 | 514: ES+ |
| 660 | 2 | | 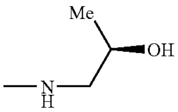 | 514: ES+ |
| 661 | 2 | | $—NH(CH_2)_3OH$ | 514: ES+ |

TABLE 51

(1)

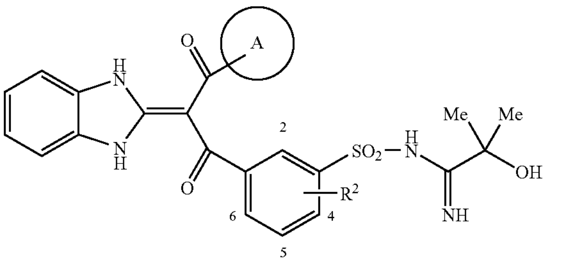

| Ex | Syn | A | $R^2$ | Dat |
|---|---|---|---|---|
| 662 | 696 | 3-F-Ph | 4-F | 541: FA; N1: 1.25 (6H, s), 5.83 (1H, m), 6.94 (1H, m), 7.04 (1H, m), 7.10 (3H, m), 7.32 (2H, m), 7.56 (1H, m), 7.76 (3H, m), 8.12 (1H, m), 8.22 (1H, m), 13.14 (2H, m) |
| 672 | 696 | 3,5-diF-Ph | 4-F | 559: FA; N1: 1.25 (6H, s), 5.82 (1H, s), 6.90-6.99 (3H, m), 7.15-7.20 (1H, m), 7.31-7.35 (2H, m), 7.60-7.64 (1H, m), 7.74-7.77 (3H, m), 8.15-8.17 (2H, m), 13.15 (2H, m) |
| 677 | 696 | 2,4,5-triF-Ph | 4-F | 577: FA; N1: 1.27 (6H, s), 5.84 (1H, s), 7.05 (1H, m), 7.19 (1H, m), 7.31-7.39 (3H, m), 7.63 (1H, m), 7.78 (3H, 1), 8.16 (1H, m), 8.25 (1H, m), 13.23 (2H, m) |
| 691 | 696 | 2,5-diF-Ph | 4-F | 559: FA; N1: 1.27 (6H, s), 5.83 (1H, m), 6.79 (1H, m), 6.95 (1H, m), 7.05 (1H, m), 7.13 (1H, m), 7.33 (2H, m), 7.60 (1H, m), 7.77 (3H, m), 8.13 (1H, m), 8.24 (1H, m), 13.21 (2H, m) |
| 695 | 696 | 5-Cl-2Thi | 4-F | 563: FA; N1: 1.27 (6H, s), 3.40-3.48 (1H, m), 5.85 (1H, s), 6.71 (1H, d, J = 4.0 Hz), 6.84 (1H, d, J = 4.0 Hz), 7.19-7.34 (3H, m), 7.61-7.75 (3H, m), 7.99-8.04 (1H, m), 8.13 (1H, br), 8.28 (1H, br), 13.01 (2H, s) |

TABLE 52

(2)

| Ex | Syn | A | $R^2$ | Dat |
|---|---|---|---|---|
| 663 | 1 | 3-F-Ph | 6-F | 541: FA |
| 664 | 1 | | 5-F | 541: FA |
| 665 | 1 | | 4-iPr | 565: FA |
| 666 | 1 | 6-Cl-3Py | 4-F | 558: FA |
| 667 | 1 | 2,5-diCl-4Py | 4-F | 592: FA |
| 668 | 19 | 3-Cl-4Py | 4-F | 558: FA |
| 669 | 19 | 4Py | 4-F | 524: FA |
| 670 | 1 | Ph | 4-F | 523: FA |
| 671 | 1 | 3-Me-Ph | 4-F | 537: FA |
| 673 | 1 | 2,4-diCl-5-F-Ph | 4-F | 609: FA |
| 674 | 1 | 2-Cl-6-OMe-4Py | 4-F | 588: FA |
| 675 | 19 | 2-OMe-4Py | 4-F | 554: ES+ |
| 676 | 1 | 3-Cl-Ph | 4-F | 557: ES+ |
| 678 | 1 | 4-Cl-Ph | 4-F | 557: FA |
| 679 | 1 | 3,4-diMe-Ph | 4-F | 551: FA |
| 680 | 1 | 3-Cl-4-Me-Ph | 4-F | 571: FA |
| 681 | 1 | 2-Me-3-F-Ph | 4-F | 555: FA |
| 682 | 1 | 2-Me-3-Cl-Ph | 4-F | 571: FA |
| 683 | 1 | 3-F-4-Me-Ph | 4-F | 555: FA |
| 684 | 1 | 3,4,5-triF-Ph | 4-F | 577: FA |
| 685 | 1 | 2-F-5-Cl-Ph | 4-F | 575: FA |
| 686 | 1 | 2-Me-5-F-Ph | 4-F | 555: FA |
| 687 | 1 | 2-Cl-5-F-Ph | 4-F | 575: FA |
| 688 | 1 | 3-F-5-Me-Ph | 4-F | 555: FA |

TABLE 52-continued (2)

| Ex | Syn | A | $R^2$ | Dat |
|---|---|---|---|---|
| 689 | 532 | 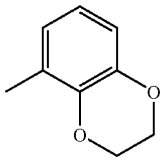 | 4-F | 581: ES+ |
| 690 | 1 | 2-Cl-3-Me-4Py | 4-F | 572: FA |
| 692 | 1 | 2-Cl-4,5-diF-Ph | 4-F | 593: FA |
| 693 | 1 | 2,5-diF-4-Cl-Ph | 4-F | 593: FA |
| 694 | 1 | 3-Cl-4,5-diF-Ph | 4-F | 593: FA |

TABLE 53

(1)

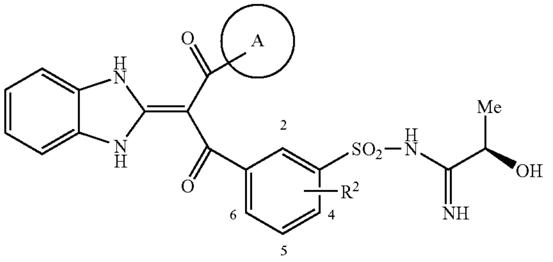

| Ex | Syn | A | $R^2$ | Dat |
|---|---|---|---|---|
| 696 | 696 | 3-F-Ph | 4-F | 527: FA; N1: 1.20 (3H, m), 4.13 (1H, m), 5.92 (1H, m), 6.94-7.12 (5H, m), 7.32 (2H, m), 7.56 (1H, m), 7.73-7.78 (3H, m), 8.16 (1H, m), 8.29 (1H, m), 13.13 (2H, m) |
| 704 | 696 | 3-Me-Ph | 4-F | 523: FA; N1: 1.20 (3H, m), 2.14 (3H, s), 4.12 (1H, m), 5.91 (1H, m), 6.90-7.08 (5H, m), 7.30 (2H, m), 7.48 (1H, m), 7.71-7.75 (3H, m), 8.14 (1H, m), 8.26 (1H, m), 13.13 (2H, m) |
| 706 | 696 | 3,5-diF-Ph | 4-F | 545: FA: N1: 1.20 (3H, d, J = 4.0 Hz), 4.11-4.13 (1H, m), 5.91 (1H, d, J = 4.0 Hz), 6.89-6.91 (2H, m), 6.97-7.02 (1H, m), 7.15-7.20 (1H, m), 7.31-7.34 (2H, m), 7.61-7.65 (1H, m), 7.73-7.77 (3H, m), 8.18 (1H, m), 8.24 (1H, m), 13.15 (2H, s) |
| 711 | 696 | 3-Cl-Ph | 4-F | 543: FA; N1: 1.20 (3H, m), 4.13 (1H, m), 5.91 (1H, m), 7.07-7.24 (5H, m), 7.31 (2H, m), 7.55 (1H, m), 7.75 (3H, m), 8.15 (1H, m), 8.29 (1H, m), 13.13 (2H, m) |
| 712 | 696 | 2,4,5-triF-Ph | 4-F | 563: FA; N1: 1.21 (3H, m), 4.13 (1H, m), 5.93 (1H, m), 7.05 (1H, m), 7.19 (1H, m), 7.28-7.37 (3H, m), 7.63 (1H, m), 7.75-7.78 (3H, m), 8.19 (1H, m), 8.31 (1H, m), 13.23 (2H, m) |
| 717 | 696 | 3-F-4-Me-Ph | 4-F | 541: FA; N1: 1.19 (3H, m), 2.07 (3H, s), 4.12 (1H, m), 5.93 (1H, m), 6.93-7.01 (3H, m), 7.10 (1H, m), 7.31 (2H, m), 7.55 (1H, m), 7.72-7.78 (3H, m), 8.16 (1H, m), 8.29 (1H, m), 13.11 (2H, m) |
| 726 | 696 | 2,5-diF-Ph | 4-F | 545: FA; N1: 1.22 (3H, m), 4.14 (1H, m), 5.93 (1H, m), 6.78 (1H, m), 6.97-7.13 (3H, m), 7.33 (2H, m), 7.59 (1H, m), 7.77 (3H, m), 8.16 (1H, m), 8.30 (1H, m), 13.21 (2H, m) |

TABLE 53-continued (1)

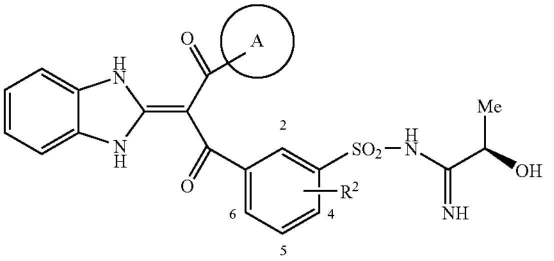

| Ex | Syn | A | $R^2$ | Dat |
|---|---|---|---|---|
| 730 | 696 | 5-Cl-2Thi | 4-F | 549: FA; N1: 1.20 (3H, d, J = 6.8 Hz), 4.10-4.18 (1H, m), 5.93 (1H, d, J = 5.2 Hz), 6.72 (1H, d, J = 4.0 Hz), 6.84 (1H, d, J = 4.0 Hz), 7.19-7.33 (3H, m), 7.62-7.75 (3H, m), 8.00-8.04 (1H, m), 8.16 (1H, brs), 8.37 (1H, brs), 13.00 (2H, s) |

TABLE 54

(2)

| Ex | Syn | A | $R^2$ | Dat |
|---|---|---|---|---|
| 697 | 1 | 3-F-Ph | 6-F | 527: FA |
| 698 | 1 | | 5-F | 527: FA |
| 699 | 1 | | 4-iPr | 551: FA |
| 700 | 1 | 6-Cl-3Py | 4-F | 544: ES+ |

TABLE 54-continued (2)

| Ex | Syn | A | $R^2$ | Dat |
|---|---|---|---|---|
| 701 | 19 | 3Py | 4-F | 510: ES+ |
| 702 | 1 | 2,5-diCl-4Py | 4-F | 578: FA |
| 703 | 1 | Ph | 4-F | 509: FA |
| 705 | 19 | 3-Cl-4Py | 4-F | 544: FA |
| 707 | 1 | 2,4-diCl-5-F-Ph | 4-F | 595: FA |
| 708 | 1 | 6-Cl-2Py | 4-F | 544: FA |
| 709 | 1 | 2-Cl-6-OMe-4Py | 4-F | 574: FA |
| 710 | 19 | 2-OMe-4Py | 4-F | 540: ES+ |
| 713 | 1 | 4-Cl-Ph | 4-F | 543: FA |
| 714 | 1 | 3,4-diMe-Ph | 4-F | 537: FA |
| 715 | 1 | 3-Cl-4-Me-Ph | 4-F | 557: FA |
| 716 | 1 | 2-Me-3-F-Ph | 4-F | 541: FA |
| 718 | 1 | 3,4,5-triF-Ph | 4-F | 563: FA |
| 719 | 1 | 2-F-5-Cl-Ph | 4-F | 561: FA |
| 720 | 1 | 2-Me-3-Cl-Ph | 4-F | 557: FA |
| 721 | 1 | 2-Me-5-F-Ph | 4-F | 541: FA |
| 722 | 1 | 2-Cl-5-F-Ph | 4-F | 559: FA |
| 723 | 1 | 3-F-5-Me-Ph | 4-F | 541: FA |
| 724 | 532 | 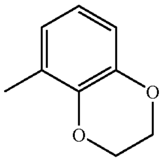 | 4-F | 567: ES+ |
| 725 | 1 | 2-Cl-3-Me-4Py | 4-F | 558: FA |
| 727 | 1 | 2-Cl-4,5-diF-Ph | 4-F | 579: FA |
| 728 | 1 | 2,5-diF-4-Cl-Ph | 4-F | 579: ES+ |
| 729 | 1 | 3-Cl-4,5-diF-Ph | 4-F | 579: FA |

TABLE 55

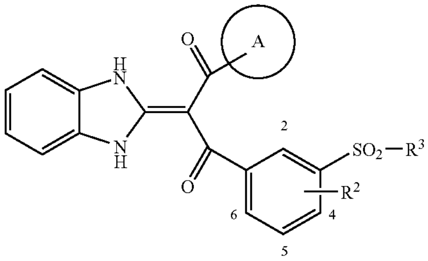

| Ex | Syn | A | $R^2$ | $R^3$ | Dat |
|---|---|---|---|---|---|
| 731 | 2 | 3-F-Ph | 4-F | $—NH(CH_2)_2OH$ | 500: FA |
| 732 | 2 | | | $—NH(CH_2)_3OH$ | 514: FA |
| 733 | 16 | | | 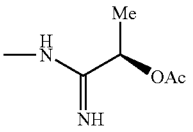 | 569: FA |
| 734 | 16 | | | 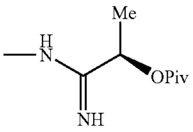 | 611: FA |

TABLE 55-continued
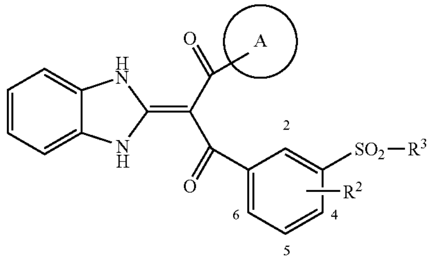
| Ex | Syn | A | $R^2$ | $R^3$ | Dat |
|---|---|---|---|---|---|
| 735 | 16 | | | 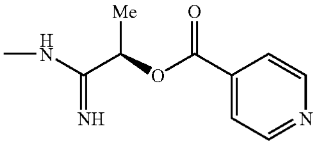 | 632: FA |
| 736 | 16 | | | 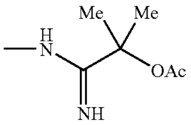 | 583: FA |
| 737 | 16 | | | 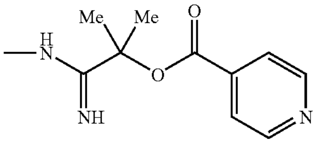 | 646: FA |
| 738 | 1 | | | 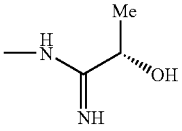 | 527: FA |
| 739 | 2 | | 4-iPr | $-NH(CH_2)_2OH$ | 524: FA |
| 740 | 1 | | | —NH—C(═NH)-Me | 521: FA |
| 741 | 1 | | 4-OMe | —NH—C(═NH)-Me | 509: FA |
| 742 | 1 | | 2-OMe | —NH—C(═NH)-Me | 509: FA |
| 743 | 1 | | | $-NH(CH_2)_2OH$ | 512: FA |
| 744 | 2 | 3-F-4-Me-Ph | 2-Me | $-NH(CH_2)_2OH$ | 510: FA |
| 745 | 2 | | | $-NH(CH_2)_3OH$ | 524: ES+ |
| 746 | 1 | 6-Cl-3Py | 4-F | —NH—C(═NH)-Me | 514: ES+ |
| 747 | 1 | 6-Cl-2Py | | —NH—C(═NH)-Me | 514: FA |
TABLE 56
| Ex | Syn | A | $R^2$ | $R^3$ | Dat |
|---|---|---|---|---|---|
| 748 | 2 | 3,5-diF-Ph | 4-F | $-NH(CH_2)_2OH$ | 518: FA |
| 749 | 1 | | | —NH—C(═NH)-Me | 515: FA |
| 750 | 1 | | | 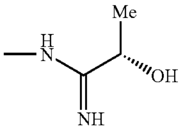 | 545: ES+ |
| 751 | 1 | 2,4-diCl-5-F-Ph | | —NH—C(═NH)-Me | 565: FA |
| 752 | 2 | | | $-NH(CH_2)_2OH$ | 568: FA |

TABLE 56-continued
| Ex | Syn | A | $R^2$ | $R^3$ | Dat |
|---|---|---|---|---|---|
| 753 | 16 | 3-Me-Ph | 4-F | 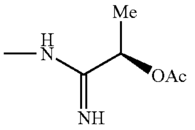 | 565: FA |
| 754 | 16 | | | 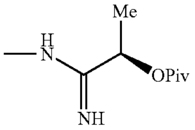 | 607: FA |
| 755 | 16 | | | 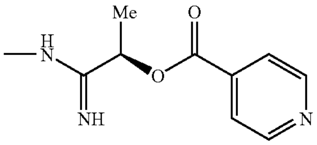 | 628: FA |
| 756 | 1 | | | 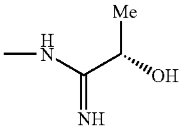 | 523: FA |
| 757 | 1 | 2,4,5-triF-Ph | 4-F | 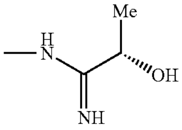 | 563: FA |
| 758 | 1 | 2,5-diF-Ph | 4-F | 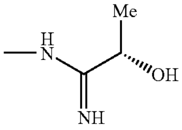 | 545: FA |
TABLE 57
| Ex | Syn | Str | Dat |
|---|---|---|---|
| 759 | 532 | 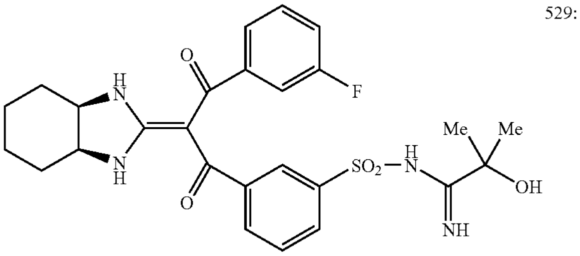 | 529: FA |
| 760 | 1 | 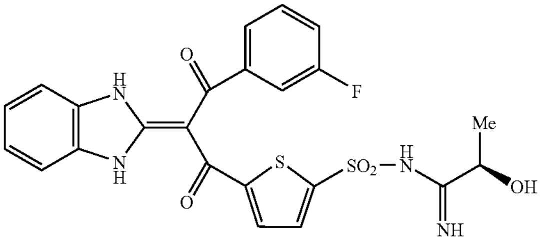 | 515: FA |

TABLE 57-continued
| Ex | Syn | Str | Dat |
|---|---|---|---|
| 761 | 1 | 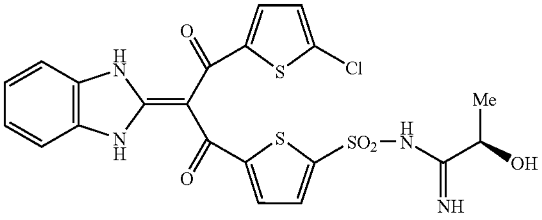 | 535: FN |
| 762 | 1 | 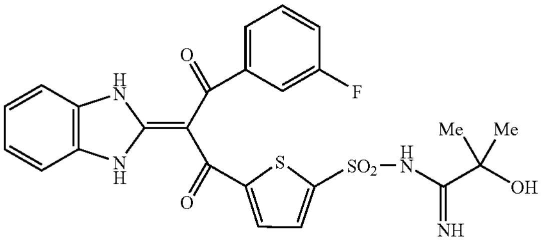 | 529: FA |
| 763 | 1 | 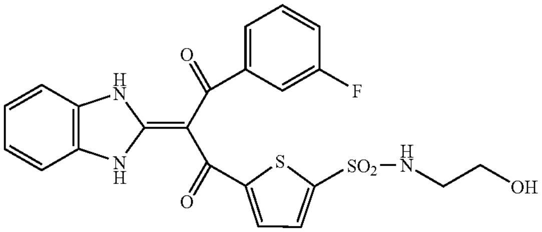 | 488: ES+ |
| 764 | 1 | 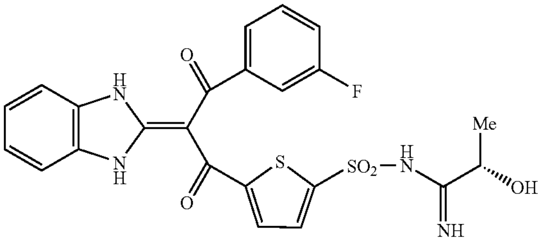 | 515: ES+ |
| 765 | 1 | 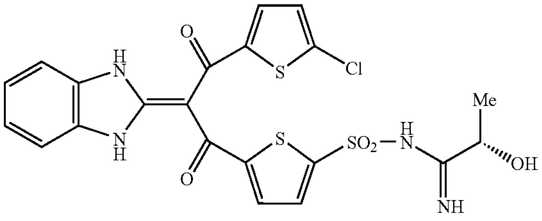 | 535: ES− |

TABLE 58

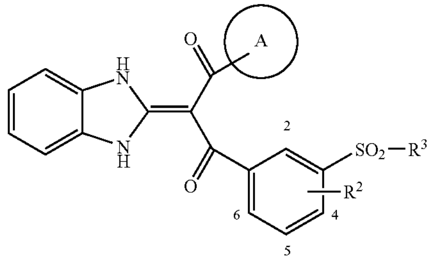

| No | A | $R^2$ | $R^3$ |
|---|---|---|---|
| 1 | 3-F-Ph | H | SM |
| 2 | 3-F-Ph | 2-Me | SM |
| 3 | 3-F-Ph | 2-Me | GN |
| 4 | 3-F-Ph | 4-Me | SM |
| 5 | 3-F-Ph | 4-Me | GN |
| 6 | 3-F-Ph | 6-Me | SM |
| 7 | 3-F-Ph | 6-Me | GN |
| 8 | 3-F-Ph | 4-F | GN |
| 9 | 3-F-Ph | 2-Cl | SM |
| 10 | 3-F-Ph | 2-Cl | DM |
| 11 | 3-F-Ph | 2-Cl | C2 |
| 12 | 3-F-Ph | 2-Cl | C3 |
| 13 | 3-F-Ph | 2-Cl | GN |
| 14 | 3-F-Ph | 4-Cl | SM |
| 15 | 3-F-Ph | 4-Cl | GN |
| 16 | 3-Cl-Ph | H | SM |
| 17 | 3-Cl-Ph | H | GN |
| 18 | 3-Cl-Ph | 2-Me | SM |
| 19 | 3-Cl-Ph | 2-Me | C3 |
| 20 | 3-Cl-Ph | 2-Me | GN |
| 21 | 3-Cl-Ph | 4-Me | SM |
| 22 | 3-Cl-Ph | 4-Me | C2 |
| 23 | 3-Cl-Ph | 4-Me | C3 |
| 24 | 3-Cl-Ph | 4-Me | GN |
| 25 | 3-Cl-Ph | 6-Me | RM |
| 26 | 3-Cl-Ph | 6-Me | SM |
| 27 | 3-Cl-Ph | 6-Me | DM |
| 28 | 3-Cl-Ph | 6-Me | C2 |
| 29 | 3-Cl-Ph | 6-Me | C3 |
| 30 | 3-Cl-Ph | 6-Me | GN |
| 31 | 3-Cl-Ph | 4-F | SM |
| 32 | 3-Cl-Ph | 4-F | C2 |
| 33 | 3-Cl-Ph | 4-F | C3 |
| 34 | 3-Cl-Ph | 4-F | GN |
| 35 | 3-Cl-Ph | 2-Cl | RM |
| 36 | 3-Cl-Ph | 2-Cl | SM |
| 37 | 3-Cl-Ph | 2-Cl | DM |
| 38 | 3-Cl-Ph | 2-Cl | C2 |
| 39 | 3-Cl-Ph | 2-Cl | C3 |
| 40 | 3-Cl-Ph | 2-Cl | GN |
| 41 | 3-Cl-Ph | 4-Cl | RM |
| 42 | 3-Cl-Ph | 4-Cl | SM |
| 43 | 3-Cl-Ph | 4-Cl | DM |
| 44 | 3-Cl-Ph | 4-Cl | C2 |
| 45 | 3-Cl-Ph | 4-Cl | C3 |
| 46 | 3-Cl-Ph | 4-Cl | GN |
| 47 | 3-Me-Ph | H | C3 |
| 48 | 3-Me-Ph | H | GN |
| 49 | 3-Me-Ph | 2-Me | SM |
| 50 | 3-Me-Ph | 2-Me | GN |
| 51 | 3-Me-Ph | 4-Me | SM |
| 52 | 3-Me-Ph | 4-Me | C2 |
| 53 | 3-Me-Ph | 4-Me | C3 |
| 54 | 3-Me-Ph | 4-Me | GN |
| 55 | 3-Me-Ph | 6-Me | SM |
| 56 | 3-Me-Ph | 6-Me | C2 |
| 57 | 3-Me-Ph | 6-Me | C3 |
| 58 | 3-Me-Ph | 6-Me | GN |
| 59 | 3-Me-Ph | 4-F | C2 |
| 60 | 3-Me-Ph | 4-F | C3 |
| 61 | 3-Me-Ph | 4-F | GN |
| 62 | 3-Me-Ph | 2-Cl | SM |
| 63 | 3-Me-Ph | 2-Cl | DM |
| 64 | 3-Me-Ph | 2-Cl | C2 |

TABLE 58-continued

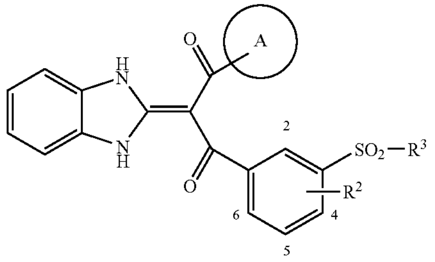

| No | A | $R^2$ | $R^3$ |
|---|---|---|---|
| 65 | 3-Me-Ph | 2-Cl | C3 |
| 66 | 3-Me-Ph | 2-Cl | GN |
| 67 | 3-Me-Ph | 4-Cl | RM |
| 68 | 3-Me-Ph | 4-Cl | SM |
| 69 | 3-Me-Ph | 4-Cl | DM |
| 70 | 3-Me-Ph | 4-Cl | C2 |
| 71 | 3-Me-Ph | 4-Cl | C3 |
| 72 | 3-Me-Ph | 4-Cl | GN |
| 73 | 3-F-4-Me-Ph | H | SM |
| 74 | 3-F-4-Me-Ph | H | GN |
| 75 | 3-F-4-Me-Ph | 2-Me | RM |
| 76 | 3-F-4-Me-Ph | 2-Me | SM |
| 77 | 3-F-4-Me-Ph | 2-Me | DM |
| 78 | 3-F-4-Me-Ph | 2-Me | GN |
| 79 | 3-F-4-Me-Ph | 4-Me | RM |
| 80 | 3-F-4-Me-Ph | 4-Me | SM |
| 81 | 3-F-4-Me-Ph | 4-Me | DM |
| 82 | 3-F-4-Me-Ph | 4-Me | C2 |
| 83 | 3-F-4-Me-Ph | 4-Me | C3 |
| 84 | 3-F-4-Me-Ph | 4-Me | GN |
| 85 | 3-F-4-Me-Ph | 6-Me | RM |
| 86 | 3-F-4-Me-Ph | 6-Me | SM |
| 87 | 3-F-4-Me-Ph | 6-Me | DM |

TABLE 59

| No | A | $R^2$ | $R^3$ |
|---|---|---|---|
| 88 | 3-F-4-Me-Ph | 6-Me | C2 |
| 89 | 3-F-4-Me-Ph | 6-Me | C3 |
| 90 | 3-F-4-Me-Ph | 6-Me | GN |
| 91 | 3-F-4-Me-Ph | 4-F | SM |
| 92 | 3-F-4-Me-Ph | 4-F | C2 |
| 93 | 3-F-4-Me-Ph | 4-F | C3 |
| 94 | 3-F-4-Me-Ph | 4-F | GN |
| 95 | 3-F-4-Me-Ph | 2-Cl | RM |
| 96 | 3-F-4-Me-Ph | 2-Cl | SM |
| 97 | 3-F-4-Me-Ph | 2-Cl | DM |
| 98 | 3-F-4-Me-Ph | 2-Cl | C2 |
| 99 | 3-F-4-Me-Ph | 2-Cl | C3 |
| 100 | 3-F-4-Me-Ph | 2-Cl | GN |
| 101 | 3-F-4-Me-Ph | 4-Cl | RM |
| 102 | 3-F-4-Me-Ph | 4-Cl | SM |
| 103 | 3-F-4-Me-Ph | 4-Cl | DM |
| 104 | 3-F-4-Me-Ph | 4-Cl | C2 |
| 105 | 3-F-4-Me-Ph | 4-Cl | C3 |
| 106 | 3-F-4-Me-Ph | 4-Cl | GN |
| 107 | 2,5-diF-Ph | H | SM |
| 108 | 2,5-diF-Ph | H | GN |
| 109 | 2,5-diF-Ph | 2-Me | SM |
| 110 | 2,5-diF-Ph | 2-Me | DM |
| 111 | 2,5-diF-Ph | 2-Me | C2 |
| 112 | 2,5-diF-Ph | 2-Me | C3 |
| 113 | 2,5-diF-Ph | 2-Me | GN |
| 114 | 2,5-diF-Ph | 4-Me | RM |
| 115 | 2,5-diF-Ph | 4-Me | SM |
| 116 | 2,5-diF-Ph | 4-Me | DM |
| 117 | 2,5-diF-Ph | 4-Me | C2 |
| 118 | 2,5-diF-Ph | 4-Me | C3 |
| 119 | 2,5-diF-Ph | 4-Me | GN |
| 120 | 2,5-diF-Ph | 6-Me | RM |
| 121 | 2,5-diF-Ph | 6-Me | SM |

TABLE 59-continued

| No | A | $R^2$ | $R^3$ |
|---|---|---|---|
| 122 | 2,5-diF-Ph | 6-Me | DM |
| 123 | 2,5-diF-Ph | 6-Me | C2 |
| 124 | 2,5-diF-Ph | 6-Me | C3 |
| 125 | 2,5-diF-Ph | 6-Me | GN |
| 126 | 2,5-diF-Ph | 4-F | C2 |
| 127 | 2,5-diF-Ph | 4-F | C3 |
| 128 | 2,5-diF-Ph | 4-F | GN |
| 129 | 2,5-diF-Ph | 2-Cl | RM |
| 130 | 2,5-diF-Ph | 2-Cl | SM |
| 131 | 2,5-diF-Ph | 2-Cl | DM |
| 132 | 2,5-diF-Ph | 2-Cl | C2 |
| 133 | 2,5-diF-Ph | 2-Cl | C3 |
| 134 | 2,5-diF-Ph | 2-Cl | GN |
| 135 | 2,5-diF-Ph | 4-Cl | RM |
| 136 | 2,5-diF-Ph | 4-Cl | SM |
| 137 | 2,5-diF-Ph | 4-Cl | DM |
| 138 | 2,5-diF-Ph | 4-Cl | C2 |
| 139 | 2,5-diF-Ph | 4-Cl | C3 |
| 140 | 2,5-diF-Ph | 4-Cl | GN |
| 141 | 3,5-diF-Ph | 2-Me | SM |
| 142 | 3,5-diF-Ph | 2-Me | GN |
| 143 | 3,5-diF-Ph | 4-Me | SM |
| 144 | 3,5-diF-Ph | 4-Me | GN |
| 145 | 3,5-diF-Ph | 6-Me | SM |
| 146 | 3,5-diF-Ph | 6-Me | GN |
| 147 | 3,5-diF-Ph | 4-F | C3 |
| 148 | 3,5-diF-Ph | 4-F | GN |
| 149 | 3,5-diF-Ph | 2-Cl | SM |
| 150 | 3,5-diF-Ph | 2-Cl | DM |
| 151 | 3,5-diF-Ph | 2-Cl | C2 |
| 152 | 3,5-diF-Ph | 2-Cl | C3 |
| 153 | 3,5-diF-Ph | 2-Cl | GN |
| 154 | 3,5-diF-Ph | 4-Cl | RM |
| 155 | 3,5-diF-Ph | 4-Cl | SM |
| 156 | 3,5-diF-Ph | 4-Cl | DM |
| 157 | 3,5-diF-Ph | 4-Cl | C2 |
| 158 | 3,5-diF-Ph | 4-Cl | C3 |
| 159 | 3,5-diF-Ph | 4-Cl | GN |
| 160 | 2,4,5-triF-Ph | H | SM |
| 161 | 2,4,5-triF-Ph | H | C3 |
| 162 | 2,4,5-triF-Ph | H | GN |
| 163 | 2,4,5-triF-Ph | 2-Me | RM |
| 164 | 2,4,5-triF-Ph | 2-Me | SM |
| 165 | 2,4,5-triF-Ph | 2-Me | DM |
| 166 | 2,4,5-triF-Ph | 2-Me | C2 |
| 167 | 2,4,5-triF-Ph | 2-Me | C3 |
| 168 | 2,4,5-triF-Ph | 2-Me | GN |
| 169 | 2,4,5-triF-Ph | 4-Me | RM |
| 170 | 2,4,5-triF-Ph | 4-Me | SM |
| 171 | 2,4,5-triF-Ph | 4-Me | DM |
| 172 | 2,4,5-triF-Ph | 4-Me | C2 |
| 173 | 2,4,5-triF-Ph | 4-Me | C3 |
| 174 | 2,4,5-triF-Ph | 4-Me | GN |
| 175 | 2,4,5-triF-Ph | 6-Me | RM |
| 176 | 2,4,5-triF-Ph | 6-Me | SM |
| 177 | 2,4,5-triF-Ph | 6-Me | DM |
| 178 | 2,4,5-triF-Ph | 6-Me | C2 |
| 179 | 2,4,5-triF-Ph | 6-Me | C3 |
| 180 | 2,4,5-triF-Ph | 6-Me | GN |
| 181 | 2,4,5-triF-Ph | 4-F | C2 |
| 182 | 2,4,5-triF-Ph | 4-F | C3 |
| 183 | 2,4,5-triF-Ph | 4-F | GN |
| 184 | 2,4,5-triF-Ph | 2-Cl | RM |
| 185 | 2,4,5-triF-Ph | 2-Cl | SM |
| 186 | 2,4,5-triF-Ph | 2-Cl | DM |
| 187 | 2,4,5-triF-Ph | 2-Cl | C2 |
| 188 | 2,4,5-triF-Ph | 2-Cl | C3 |
| 189 | 2,4,5-triF-Ph | 2-Cl | GN |
| 190 | 2,4,5-triF-Ph | 4-Cl | RM |
| 191 | 2,4,5-triF-Ph | 4-Cl | SM |
| 192 | 2,4,5-triF-Ph | 4-Cl | DM |
| 193 | 2,4,5-triF-Ph | 4-Cl | C2 |
| 194 | 2,4,5-triF-Ph | 4-Cl | C3 |
| 195 | 2,4,5-triF-Ph | 4-Cl | GN |

TABLE 60

| No | A | $R^2$ | $R^3$ |
|---|---|---|---|
| 196 | 4-F-2Thi | H | RM |
| 197 | 4-F-2Thi | H | SM |
| 198 | 4-F-2Thi | H | DM |
| 199 | 4-F-2Thi | H | C2 |
| 200 | 4-F-2Thi | H | C3 |
| 201 | 4-F-2Thi | H | GN |
| 202 | 4-F-2Thi | 2-Me | RM |
| 203 | 4-F-2Thi | 2-Me | SM |
| 204 | 4-F-2Thi | 2-Me | DM |
| 205 | 4-F-2Thi | 2-Me | C2 |
| 206 | 4-F-2Thi | 2-Me | C3 |
| 207 | 4-F-2Thi | 2-Me | GN |
| 208 | 4-F-2Thi | 4-Me | RM |
| 209 | 4-F-2Thi | 4-Me | SM |
| 210 | 4-F-2Thi | 4-Me | DM |
| 211 | 4-F-2Thi | 4-Me | C2 |
| 212 | 4-F-2Thi | 4-Me | C3 |
| 213 | 4-F-2Thi | 4-Me | GN |
| 214 | 4-F-2Thi | 6-Me | RM |
| 215 | 4-F-2Thi | 6-Me | SM |
| 216 | 4-F-2Thi | 6-Me | DM |
| 217 | 4-F-2Thi | 6-Me | C2 |
| 218 | 4-F-2Thi | 6-Me | C3 |
| 219 | 4-F-2Thi | 6-Me | GN |
| 220 | 4-F-2Thi | 4-F | RM |
| 221 | 4-F-2Thi | 4-F | SM |
| 222 | 4-F-2Thi | 4-F | DM |
| 223 | 4-F-2Thi | 4-F | C2 |
| 224 | 4-F-2Thi | 4-F | C3 |
| 225 | 4-F-2Thi | 4-F | GN |
| 226 | 4-F-2Thi | 2-Cl | RM |
| 227 | 4-F-2Thi | 2-Cl | SM |
| 228 | 4-F-2Thi | 2-Cl | DM |
| 229 | 4-F-2Thi | 2-Cl | C2 |
| 230 | 4-F-2Thi | 2-Cl | C3 |
| 231 | 4-F-2Thi | 2-Cl | GN |
| 232 | 4-F-2Thi | 4-Cl | RM |
| 233 | 4-F-2Thi | 4-Cl | SM |
| 234 | 4-F-2Thi | 4-Cl | DM |
| 235 | 4-F-2Thi | 4-Cl | C2 |
| 236 | 4-F-2Thi | 4-Cl | C3 |
| 237 | 4-F-2Thi | 4-Cl | GN |
| 238 | 5-F-2Thi | H | RM |
| 239 | 5-F-2Thi | H | SM |
| 240 | 5-F-2Thi | H | DM |
| 241 | 5-F-2Thi | H | C2 |
| 242 | 5-F-2Thi | H | C3 |
| 243 | 5-F-2Thi | H | GN |
| 244 | 5-F-2Thi | 2-Me | RM |
| 245 | 5-F-2Thi | 2-Me | SM |
| 246 | 5-F-2Thi | 2-Me | DM |
| 247 | 5-F-2Thi | 2-Me | C2 |
| 248 | 5-F-2Thi | 2-Me | C3 |
| 249 | 5-F-2Thi | 2-Me | GN |
| 250 | 5-F-2Thi | 4-Me | RM |
| 251 | 5-F-2Thi | 4-Me | SM |
| 252 | 5-F-2Thi | 4-Me | DM |
| 253 | 5-F-2Thi | 4-Me | C2 |
| 254 | 5-F-2Thi | 4-Me | C3 |
| 255 | 5-F-2Thi | 4-Me | GN |
| 256 | 5-F-2Thi | 6-Me | RM |
| 257 | 5-F-2Thi | 6-Me | SM |
| 258 | 5-F-2Thi | 6-Me | DM |
| 259 | 5-F-2Thi | 6-Me | C2 |
| 260 | 5-F-2Thi | 6-Me | C3 |
| 261 | 5-F-2Thi | 6-Me | GN |
| 262 | 5-F-2Thi | 4-F | RM |
| 263 | 5-F-2Thi | 4-F | SM |
| 264 | 5-F-2Thi | 4-F | DM |
| 265 | 5-F-2Thi | 4-F | C2 |
| 266 | 5-F-2Thi | 4-F | C3 |
| 267 | 5-F-2Thi | 4-F | GN |
| 268 | 5-F-2Thi | 2-Cl | RM |
| 269 | 5-F-2Thi | 2-Cl | SM |
| 270 | 5-F-2Thi | 2-Cl | DM |
| 271 | 5-F-2Thi | 2-Cl | C2 |
| 272 | 5-F-2Thi | 2-Cl | C3 |
| 273 | 5-F-2Thi | 2-Cl | GN |

TABLE 60-continued

| No | A | $R^2$ | $R^3$ |
|---|---|---|---|
| 274 | 5-F-2Thi | 4-Cl | RM |
| 275 | 5-F-2Thi | 4-Cl | SM |
| 276 | 5-F-2Thi | 4-Cl | DM |
| 277 | 5-F-2Thi | 4-Cl | C2 |
| 278 | 5-F-2Thi | 4-Cl | C3 |
| 279 | 5-F-2Thi | 4-Cl | GN |
| 280 | 5-Cl-2Thi | H | SM |
| 281 | 5-Cl-2Thi | H | C2 |
| 282 | 5-Cl-2Thi | H | C3 |
| 283 | 5-Cl-2Thi | H | GN |
| 284 | 5-Cl-2Thi | 2-Me | RM |
| 285 | 5-Cl-2Thi | 2-Me | SM |
| 286 | 5-Cl-2Thi | 2-Me | DM |
| 287 | 5-Cl-2Thi | 2-Me | C2 |
| 288 | 5-Cl-2Thi | 2-Me | C3 |
| 289 | 5-Cl-2Thi | 2-Me | GN |
| 290 | 5-Cl-2Thi | 4-Me | RM |
| 291 | 5-Cl-2Thi | 4-Me | SM |
| 292 | 5-Cl-2Thi | 4-Me | DM |
| 293 | 5-Cl-2Thi | 4-Me | C2 |
| 294 | 5-Cl-2Thi | 4-Me | C3 |
| 295 | 5-Cl-2Thi | 4-Me | GN |
| 296 | 5-Cl-2Thi | 6-Me | RM |
| 297 | 5-Cl-2Thi | 6-Me | SM |
| 298 | 5-Cl-2Thi | 6-Me | DM |
| 299 | 5-Cl-2Thi | 6-Me | C2 |
| 300 | 5-Cl-2Thi | 6-Me | C3 |
| 301 | 5-Cl-2Thi | 6-Me | GN |
| 302 | 5-Cl-2Thi | 4-F | SM |
| 303 | 5-Cl-2Thi | 4-F | C2 |

TABLE 61

| No | A | $R^2$ | $R^3$ |
|---|---|---|---|
| 304 | 5-Cl-2Thi | 4-F | C3 |
| 305 | 5-Cl-2Thi | 4-F | GN |
| 306 | 5-Cl-2Thi | 2-Cl | RM |
| 307 | 5-Cl-2Thi | 2-Cl | SM |
| 308 | 5-Cl-2Thi | 2-Cl | DM |
| 309 | 5-Cl-2Thi | 2-Cl | C2 |
| 310 | 5-Cl-2Thi | 2-Cl | C3 |
| 311 | 5-Cl-2Thi | 2-Cl | GN |
| 312 | 5-Cl-2Thi | 4-Cl | RM |
| 313 | 5-Cl-2Thi | 4-Cl | SM |
| 314 | 5-Cl-2Thi | 4-Cl | DM |
| 315 | 5-Cl-2Thi | 4-Cl | C2 |
| 316 | 5-Cl-2Thi | 4-Cl | C3 |
| 317 | 5-Cl-2Thi | 4-Cl | GN |

TABLE 62

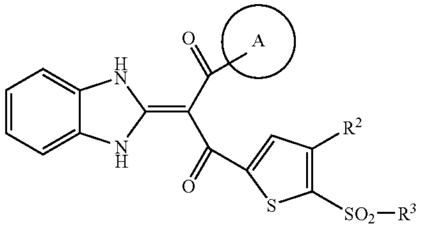

| No. | A | $R^2$ | $R^3$ |
|---|---|---|---|
| 318 | 3-F-Ph | H | C3 |
| 319 | 3-F-Ph | H | GN |
| 320 | 3-F-Ph | Me | RM |
| 321 | 3-F-Ph | Me | SM |
| 322 | 3-F-Ph | Me | DM |
| 323 | 3-F-Ph | Me | C2 |
| 324 | 3-F-Ph | Me | C3 |

TABLE 62-continued

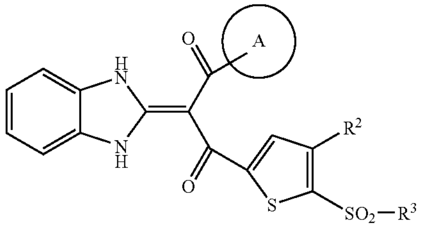

| No. | A | $R^2$ | $R^3$ |
|---|---|---|---|
| 325 | 3-F-Ph | Me | GN |
| 326 | 3-Cl-Ph | H | RM |
| 327 | 3-Cl-Ph | H | SM |
| 328 | 3-Cl-Ph | H | DM |
| 329 | 3-Cl-Ph | H | C2 |
| 330 | 3-Cl-Ph | H | C3 |
| 331 | 3-Cl-Ph | H | GN |
| 332 | 3-Cl-Ph | Me | RM |
| 333 | 3-Cl-Ph | Me | SM |
| 334 | 3-Cl-Ph | Me | DM |
| 335 | 3-Cl-Ph | Me | C2 |
| 336 | 3-Cl-Ph | Me | C3 |
| 337 | 3-Cl-Ph | Me | GN |
| 338 | 3-Me-Ph | H | RM |
| 339 | 3-Me-Ph | H | SM |
| 340 | 3-Me-Ph | H | DM |
| 341 | 3-Me-Ph | H | C2 |
| 342 | 3-Me-Ph | H | C3 |
| 343 | 3-Me-Ph | H | GN |
| 344 | 3-Me-Ph | Me | RM |
| 345 | 3-Me-Ph | Me | SM |
| 346 | 3-Me-Ph | Me | DM |
| 347 | 3-Me-Ph | Me | C2 |
| 348 | 3-Me-Ph | Me | C3 |
| 349 | 3-Me-Ph | Me | GN |
| 350 | 3-F-4-Me-Ph | H | RM |
| 351 | 3-F-4-Me-Ph | H | SM |
| 352 | 3-F-4-Me-Ph | H | DM |
| 353 | 3-F-4-Me-Ph | H | C2 |
| 354 | 3-F-4-Me-Ph | H | C3 |
| 355 | 3-F-4-Me-Ph | H | GN |
| 356 | 3-F-4-Me-Ph | Me | RM |
| 357 | 3-F-4-Me-Ph | Me | SM |
| 358 | 3-F-4-Me-Ph | Me | DM |
| 359 | 3-F-4-Me-Ph | Me | C2 |
| 360 | 3-F-4-Me-Ph | Me | C3 |
| 361 | 3-F-4-Me-Ph | Me | GN |
| 362 | 2,5-diF-Ph | H | RM |
| 363 | 2,5-diF-Ph | H | SM |
| 364 | 2,5-diF-Ph | H | DM |
| 365 | 2,5-diF-Ph | H | C2 |
| 366 | 2,5-diF-Ph | H | C3 |
| 367 | 2,5-diF-Ph | H | GN |
| 368 | 2,5-diF-Ph | Me | RM |
| 369 | 2,5-diF-Ph | Me | SM |
| 370 | 2,5-diF-Ph | Me | DM |
| 371 | 2,5-diF-Ph | Me | C2 |
| 372 | 2,5-diF-Ph | Me | C3 |
| 373 | 2,5-diF-Ph | Me | GN |
| 374 | 3,5-diF-Ph | H | RM |
| 375 | 3,5-diF-Ph | H | SM |
| 376 | 3,5-diF-Ph | H | DM |
| 377 | 3,5-diF-Ph | H | C2 |
| 378 | 3,5-diF-Ph | H | C3 |
| 379 | 3,5-diF-Ph | H | GN |
| 380 | 3,5-diF-Ph | Me | RM |
| 381 | 3,5-diF-Ph | Me | SM |
| 382 | 3,5-diF-Ph | Me | DM |
| 383 | 3,5-diF-Ph | Me | C2 |

TABLE 63

| No | A | $R^2$ | $R^3$ |
|---|---|---|---|
| 384 | 3,5-diF-Ph | Me | C3 |
| 385 | 3,5-diF-Ph | Me | GN |
| 386 | 2,4,5-triF-Ph | H | RM |
| 387 | 2,4,5-triF-Ph | H | SM |
| 388 | 2,4,5-triF-Ph | H | DM |
| 389 | 2,4,5-triF-Ph | H | C2 |
| 390 | 2,4,5-triF-Ph | H | C3 |
| 391 | 2,4,5-triF-Ph | H | GN |
| 392 | 2,4,5-triF-Ph | Me | RM |
| 393 | 2,4,5-triF-Ph | Me | SM |
| 394 | 2,4,5-triF-Ph | Me | DM |
| 395 | 2,4,5-triF-Ph | Me | C2 |
| 396 | 2,4,5-triF-Ph | Me | C3 |
| 397 | 2,4,5-triF-Ph | Me | GN |
| 398 | 4-F-2Thi | H | RM |
| 399 | 4-F-2Thi | H | SM |
| 400 | 4-F-2Thi | H | DM |
| 401 | 4-F-2Thi | H | C2 |
| 402 | 4-F-2Thi | H | C3 |
| 403 | 4-F-2Thi | H | GN |
| 404 | 4-F-2Thi | Me | RM |
| 405 | 4-F-2Thi | Me | SM |
| 406 | 4-F-2Thi | Me | DM |
| 407 | 4-F-2Thi | Me | C2 |
| 408 | 4-F-2Thi | Me | C3 |
| 409 | 4-F-2Thi | Me | GN |
| 410 | 5-F-2Thi | H | RM |
| 411 | 5-F-2Thi | H | SM |
| 412 | 5-F-2Thi | H | DM |
| 413 | 5-F-2Thi | H | C2 |
| 414 | 5-F-2Thi | H | C3 |
| 415 | 5-F-2Thi | H | GN |
| 416 | 5-F-2Thi | Me | RM |
| 417 | 5-F-2Thi | Me | SM |
| 418 | 5-F-2Thi | Me | DM |
| 419 | 5-F-2Thi | Me | C2 |
| 420 | 5-F-2Thi | Me | C3 |
| 421 | 5-F-2Thi | Me | GN |
| 422 | 5-Cl-2Thi | H | DM |
| 423 | 5-Cl-2Thi | H | C2 |
| 424 | 5-Cl-2Thi | H | C3 |
| 425 | 5-Cl-2Thi | H | GN |
| 426 | 5-Cl-2Thi | Me | RM |
| 427 | 5-Cl-2Thi | Me | SM |
| 428 | 5-Cl-2Thi | Me | DM |
| 429 | 5-Cl-2Thi | Me | C2 |
| 430 | 5-Cl-2Thi | Me | C3 |
| 431 | 5-Cl-2Thi | Me | GN |

TABLE 64

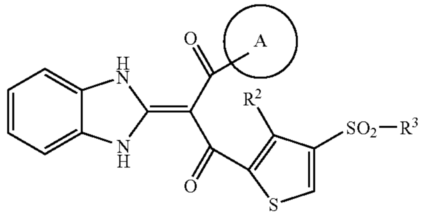

| No | A | $R^2$ | $R^3$ |
|---|---|---|---|
| 432 | 3-F-Ph | H | RM |
| 433 | 3-F-Ph | H | SM |
| 434 | 3-F-Ph | H | DM |
| 435 | 3-F-Ph | H | C2 |
| 436 | 3-F-Ph | H | C3 |
| 437 | 3-F-Ph | H | GN |
| 438 | 3-F-Ph | Me | RM |
| 439 | 3-F-Ph | Me | SM |
| 440 | 3-F-Ph | Me | DM |
| 441 | 3-F-Ph | Me | C2 |
| 442 | 3-F-Ph | Me | C3 |

TABLE 64-continued

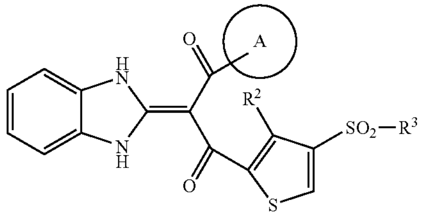

| No | A | $R^2$ | $R^3$ |
|---|---|---|---|
| 443 | 3-F-Ph | Me | GN |
| 444 | 3-Cl-Ph | H | RM |
| 445 | 3-Cl-Ph | H | SM |
| 446 | 3-Cl-Ph | H | DM |
| 447 | 3-Cl-Ph | H | C2 |
| 448 | 3-Cl-Ph | H | C3 |
| 449 | 3-Cl-Ph | H | GN |
| 450 | 3-Cl-Ph | Me | RM |
| 451 | 3-Cl-Ph | Me | SM |
| 452 | 3-Cl-Ph | Me | DM |
| 453 | 3-Cl-Ph | Me | C2 |
| 454 | 3-Cl-Ph | Me | C3 |
| 455 | 3-Cl-Ph | Me | GN |
| 456 | 3-Me-Ph | H | RM |
| 457 | 3-Me-Ph | H | SM |
| 458 | 3-Me-Ph | H | DM |
| 459 | 3-Me-Ph | H | C2 |
| 460 | 3-Me-Ph | H | C3 |
| 461 | 3-Me-Ph | H | GN |
| 462 | 3-Me-Ph | Me | RM |
| 463 | 3-Me-Ph | Me | SM |
| 464 | 3-Me-Ph | Me | DM |

TABLE 65

| No | A | $R^2$ | $R^3$ |
|---|---|---|---|
| 465 | 3-Me-Ph | Me | C2 |
| 466 | 3-Me-Ph | Me | C3 |
| 467 | 3-Me-Ph | Me | GN |
| 468 | 3-F-4-Me-Ph | H | RM |
| 469 | 3-F-4-Me-Ph | H | SM |
| 470 | 3-F-4-Me-Ph | H | DM |
| 471 | 3-F-4-Me-Ph | H | C2 |
| 472 | 3-F-4-Me-Ph | H | C3 |
| 473 | 3-F-4-Me-Ph | H | GN |
| 474 | 3-F-4-Me-Ph | Me | RM |
| 475 | 3-F-4-Me-Ph | Me | SM |
| 476 | 3-F-4-Me-Ph | Me | DM |
| 477 | 3-F-4-Me-Ph | Me | C2 |
| 478 | 3-F-4-Me-Ph | Me | C3 |
| 479 | 3-F-4-Me-Ph | Me | GN |
| 480 | 2,5-diF-Ph | H | RM |
| 481 | 2,5-diF-Ph | H | SM |
| 482 | 2,5-diF-Ph | H | DM |
| 483 | 2,5-diF-Ph | H | C2 |
| 484 | 2,5-diF-Ph | H | C3 |
| 485 | 2,5-diF-Ph | H | GN |
| 486 | 2,5-diF-Ph | Me | RM |
| 487 | 2,5-diF-Ph | Me | SM |
| 488 | 2,5-diF-Ph | Me | DM |
| 489 | 2,5-diF-Ph | Me | C2 |
| 490 | 2,5-diF-Ph | Me | C3 |
| 491 | 2,5-diF-Ph | Me | GN |
| 492 | 3,5-diF-Ph | H | RM |
| 493 | 3,5-diF-Ph | H | SM |
| 494 | 3,5-diF-Ph | H | DM |
| 495 | 3,5-diF-Ph | H | C2 |
| 496 | 3,5-diF-Ph | H | C3 |
| 497 | 3,5-diF-Ph | H | GN |
| 498 | 3,5-diF-Ph | Me | RM |
| 499 | 3,5-diF-Ph | Me | SM |
| 500 | 3,5-diF-Ph | Me | DM |
| 501 | 3,5-diF-Ph | Me | C2 |

TABLE 65-continued

| No | A | $R^2$ | $R^3$ |
|---|---|---|---|
| 502 | 3,5-diF-Ph | Me | C3 |
| 503 | 3,5-diF-Ph | Me | GN |
| 504 | 2,4,5-triF-Ph | H | RM |
| 505 | 2,4,5-triF-Ph | H | SM |
| 506 | 2,4,5-triF-Ph | H | DM |
| 507 | 2,4,5-triF-Ph | H | C2 |
| 508 | 2,4,5-triF-Ph | H | C3 |
| 509 | 2,4,5-triF-Ph | H | GN |
| 510 | 2,4,5-triF-Ph | Me | RM |
| 511 | 2,4,5-triF-Ph | Me | SM |
| 512 | 2,4,5-triF-Ph | Me | DM |
| 513 | 2,4,5-triF-Ph | Me | C2 |
| 514 | 2,4,5-triF-Ph | Me | C3 |
| 515 | 2,4,5-triF-Ph | Me | GN |
| 516 | 4-F-2Thi | H | RM |
| 517 | 4-F-2Thi | H | SM |
| 518 | 4-F-2Thi | H | DM |
| 519 | 4-F-2Thi | H | C2 |
| 520 | 4-F-2Thi | H | C3 |
| 521 | 4-F-2Thi | H | GN |
| 522 | 4-F-2Thi | Me | RM |
| 523 | 4-F-2Thi | Me | SM |
| 524 | 4-F-2Thi | Me | DM |
| 525 | 4-F-2Thi | Me | C2 |
| 526 | 4-F-2Thi | Me | C3 |
| 527 | 4-F-2Thi | Me | GN |
| 528 | 5-F-2Thi | H | RM |
| 529 | 5-F-2Thi | H | SM |
| 530 | 5-F-2Thi | H | DM |
| 531 | 5-F-2Thi | H | C2 |
| 532 | 5-F-2Thi | H | C3 |
| 533 | 5-F-2Thi | H | GN |
| 534 | 5-F-2Thi | Me | RM |
| 535 | 5-F-2Thi | Me | SM |
| 536 | 5-F-2Thi | Me | DM |
| 537 | 5-F-2Thi | Me | C2 |
| 538 | 5-F-2Thi | Me | C3 |
| 539 | 5-F-2Thi | Me | GN |
| 540 | 5-Cl-2Thi | H | RM |
| 541 | 5-Cl-2Thi | H | SM |
| 542 | 5-Cl-2Thi | H | DM |
| 543 | 5-Cl-2Thi | H | C2 |
| 544 | 5-Cl-2Thi | H | C3 |
| 545 | 5-Cl-2Thi | H | GN |
| 546 | 5-Cl-2Thi | Me | RM |
| 547 | 5-Cl-2Thi | Me | SM |
| 548 | 5-Cl-2Thi | Me | DM |
| 549 | 5-Cl-2Thi | Me | C2 |
| 550 | 5-Cl-2Thi | Me | C3 |
| 551 | 5-Cl-2Thi | Me | GN |

TABLE 66

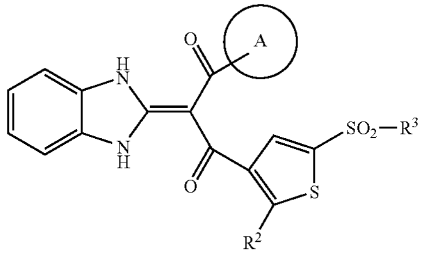

| No | A | $R^2$ | $R^3$ |
|---|---|---|---|
| 552 | 3-F-Ph | H | RM |
| 553 | 3-F-Ph | H | SM |
| 554 | 3-F-Ph | H | DM |
| 555 | 3-F-Ph | H | C2 |
| 556 | 3-F-Ph | H | C3 |
| 557 | 3-F-Ph | H | GN |
| 558 | 3-F-Ph | Cl | RM |
| 559 | 3-F-Ph | Cl | SM |

TABLE 66-continued

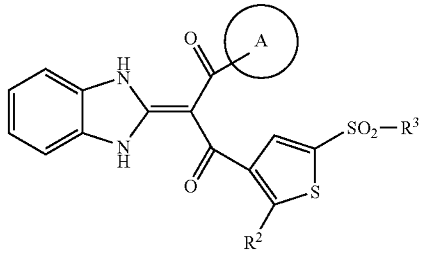

| No | A | $R^2$ | $R^3$ |
|---|---|---|---|
| 560 | 3-F-Ph | Cl | DM |
| 561 | 3-F-Ph | Cl | C2 |
| 562 | 3-F-Ph | Cl | C3 |
| 563 | 3-F-Ph | Cl | GN |
| 564 | 3-Cl-Ph | H | RM |
| 565 | 3-Cl-Ph | H | SM |
| 566 | 3-Cl-Ph | H | DM |
| 567 | 3-Cl-Ph | H | C2 |
| 568 | 3-Cl-Ph | H | C3 |
| 569 | 3-Cl-Ph | H | GN |
| 570 | 3-Cl-Ph | Cl | RM |
| 571 | 3-Cl-Ph | Cl | SM |
| 572 | 3-Cl-Ph | Cl | DM |
| 573 | 3-Cl-Ph | Cl | C2 |
| 574 | 3-Cl-Ph | Cl | C3 |
| 575 | 3-Cl-Ph | Cl | GN |
| 576 | 3-Me-Ph | H | RM |
| 577 | 3-Me-Ph | H | SM |
| 578 | 3-Me-Ph | H | DM |
| 579 | 3-Me-Ph | H | C2 |
| 580 | 3-Me-Ph | H | C3 |
| 581 | 3-Me-Ph | H | GN |
| 582 | 3-Me-Ph | Cl | RM |
| 583 | 3-Me-Ph | Cl | SM |
| 584 | 3-Me-Ph | Cl | DM |
| 585 | 3-Me-Ph | Cl | C2 |
| 586 | 3-Me-Ph | Cl | C3 |
| 587 | 3-Me-Ph | Cl | GN |
| 588 | 3-F-4-Me-Ph | H | RM |
| 589 | 3-F-4-Me-Ph | H | SM |
| 590 | 3-F-4-Me-Ph | H | DM |
| 591 | 3-F-4-Me-Ph | H | C2 |
| 592 | 3-F-4-Me-Ph | H | C3 |
| 593 | 3-F-4-Me-Ph | H | GN |
| 594 | 3-F-4-Me-Ph | Cl | RM |
| 595 | 3-F-4-Me-Ph | Cl | SM |
| 596 | 3-F-4-Me-Ph | Cl | DM |
| 597 | 3-F-4-Me-Ph | Cl | C2 |
| 598 | 3-F-4-Me-Ph | Cl | C3 |
| 599 | 3-F-4-Me-Ph | Cl | GN |
| 600 | 2,5-diF-Ph | H | RM |
| 601 | 2,5-diF-Ph | H | SM |
| 602 | 2,5-diF-Ph | H | DM |
| 603 | 2,5-diF-Ph | H | C2 |
| 604 | 2,5-diF-Ph | H | C3 |
| 605 | 2,5-diF-Ph | H | GN |
| 606 | 2,5-diF-Ph | Cl | RM |
| 607 | 2,5-diF-Ph | Cl | SM |
| 608 | 2,5-diF-Ph | Cl | DM |
| 609 | 2,5-diF-Ph | Cl | C2 |
| 610 | 2,5-diF-Ph | Cl | C3 |
| 611 | 2,5-diF-Ph | Cl | GN |
| 612 | 3,5-diF-Ph | H | RM |
| 613 | 3,5-diF-Ph | H | SM |
| 614 | 3,5-diF-Ph | H | DM |
| 615 | 3,5-diF-Ph | H | C2 |
| 616 | 3,5-diF-Ph | H | C3 |
| 617 | 3,5-diF-Ph | H | GN |
| 618 | 3,5-diF-Ph | Cl | RM |
| 619 | 3,5-diF-Ph | Cl | SM |
| 620 | 3,5-diF-Ph | Cl | DM |
| 621 | 3,5-diF-Ph | Cl | C2 |
| 622 | 3,5-diF-Ph | Cl | C3 |
| 623 | 3,5-diF-Ph | Cl | GN |
| 624 | 2,4,5-triF-Ph | H | RM |

TABLE 66-continued

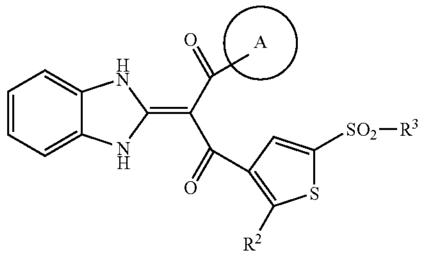

| No | A | $R^2$ | $R^3$ |
|---|---|---|---|
| 625 | 2,4,5-triF-Ph | H | SM |
| 626 | 2,4,5-triF-Ph | H | DM |
| 627 | 2,4,5-triF-Ph | H | C2 |
| 628 | 2,4,5-triF-Ph | H | C3 |
| 629 | 2,4,5-triF-Ph | H | GN |
| 630 | 2,4,5-triF-Ph | Cl | RM |
| 631 | 2,4,5-triF-Ph | Cl | SM |
| 632 | 2,4,5-triF-Ph | Cl | DM |
| 633 | 2,4,5-triF-Ph | Cl | C2 |
| 634 | 2,4,5-triF-Ph | Cl | C3 |
| 635 | 2,4,5-triF-Ph | Cl | GN |
| 636 | 4-F-2Thi | H | RM |
| 637 | 4-F-2Thi | H | SM |
| 638 | 4-F-2Thi | H | DM |
| 639 | 4-F-2Thi | H | C2 |
| 640 | 4-F-2Thi | H | C3 |
| 641 | 4-F-2Thi | H | GN |

TABLE 67

| No | A | $R^2$ | $R^3$ |
|---|---|---|---|
| 642 | 4-F-2Thi | Cl | RM |
| 643 | 4-F-2Thi | Cl | SM |
| 644 | 4-F-2Thi | Cl | DM |
| 645 | 4-F-2Thi | Cl | C2 |
| 646 | 4-F-2Thi | Cl | C3 |
| 647 | 4-F-2Thi | Cl | GN |
| 648 | 5-F-2Thi | H | RM |
| 649 | 5-F-2Thi | H | SM |
| 650 | 5-F-2Thi | H | DM |
| 651 | 5-F-2Thi | H | C2 |
| 652 | 5-F-2Thi | H | C3 |
| 653 | 5-F-2Thi | H | GN |
| 654 | 5-F-2Thi | Cl | RM |
| 655 | 5-F-2Thi | Cl | SM |
| 656 | 5-F-2Thi | Cl | DM |
| 657 | 5-F-2Thi | Cl | C2 |
| 658 | 5-F-2Thi | Cl | C3 |
| 659 | 5-F-2Thi | Cl | GN |
| 660 | 5-Cl-2Thi | H | RM |
| 661 | 5-Cl-2Thi | H | SM |
| 662 | 5-Cl-2Thi | H | DM |
| 663 | 5-Cl-2Thi | H | C2 |
| 664 | 5-Cl-2Thi | H | C3 |
| 665 | 5-Cl-2Thi | H | GN |
| 666 | 5-Cl-2Thi | Cl | RM |
| 667 | 5-Cl-2Thi | Cl | SM |
| 668 | 5-Cl-2Thi | Cl | DM |
| 669 | 5-Cl-2Thi | Cl | C2 |
| 670 | 5-Cl-2Thi | Cl | C3 |
| 671 | 5-Cl-2Thi | Cl | GN |

TABLE 68

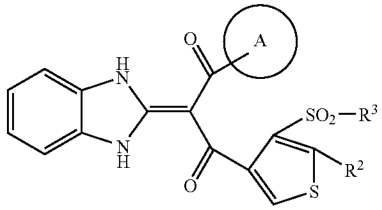

| No | A | $R^2$ | $R^3$ |
|---|---|---|---|
| 672 | 3-F-Ph | H | RM |
| 673 | 3-F-Ph | H | SM |
| 674 | 3-F-Ph | H | DM |
| 675 | 3-F-Ph | H | C2 |
| 676 | 3-F-Ph | H | C3 |
| 677 | 3-F-Ph | H | GN |
| 678 | 3-F-Ph | Cl | RM |
| 679 | 3-F-Ph | Cl | SM |
| 680 | 3-F-Ph | Cl | DM |
| 681 | 3-F-Ph | Cl | C2 |
| 682 | 3-F-Ph | Cl | C3 |
| 683 | 3-F-Ph | Cl | GN |
| 684 | 3-F-Ph | Me | RM |
| 685 | 3-F-Ph | Me | SM |
| 686 | 3-F-Ph | Me | DM |
| 687 | 3-F-Ph | Me | C2 |
| 688 | 3-F-Ph | Me | C3 |
| 689 | 3-F-Ph | Me | GN |
| 690 | 3-Cl-Ph | H | RM |
| 691 | 3-Cl-Ph | H | SM |
| 692 | 3-Cl-Ph | H | DM |
| 693 | 3-Cl-Ph | H | C2 |
| 694 | 3-Cl-Ph | H | C3 |
| 695 | 3-Cl-Ph | H | GN |
| 696 | 3-Cl-Ph | Cl | RM |
| 697 | 3-Cl-Ph | Cl | SM |
| 698 | 3-Cl-Ph | Cl | DM |
| 699 | 3-Cl-Ph | Cl | C2 |
| 700 | 3-Cl-Ph | Cl | C3 |
| 701 | 3-Cl-Ph | Cl | GN |
| 702 | 3-Cl-Ph | Me | RM |
| 703 | 3-Cl-Ph | Me | SM |
| 704 | 3-Cl-Ph | Me | DM |
| 705 | 3-Cl-Ph | Me | C2 |
| 706 | 3-Cl-Ph | Me | C3 |
| 707 | 3-Cl-Ph | Me | GN |
| 708 | 3-Me-Ph | H | RM |
| 709 | 3-Me-Ph | H | SM |
| 710 | 3-Me-Ph | H | DM |
| 711 | 3-Me-Ph | H | C2 |
| 712 | 3-Me-Ph | H | C3 |
| 713 | 3-Me-Ph | H | GN |
| 714 | 3-Me-Ph | Cl | RM |
| 715 | 3-Me-Ph | Cl | SM |
| 716 | 3-Me-Ph | Cl | DM |
| 717 | 3-Me-Ph | Cl | C2 |
| 718 | 3-Me-Ph | Cl | C3 |
| 719 | 3-Me-Ph | Cl | GN |
| 720 | 3-Me-Ph | Me | RM |
| 721 | 3-Me-Ph | Me | SM |
| 722 | 3-Me-Ph | Me | DM |

TABLE 69

| No | A | $R^2$ | $R^3$ |
|---|---|---|---|
| 723 | 3-Me-Ph | Me | C2 |
| 724 | 3-Me-Ph | Me | C3 |
| 725 | 3-Me-Ph | Me | GN |
| 726 | 3-F-4-Me-Ph | H | RM |
| 727 | 3-F-4-Me-Ph | H | SM |
| 728 | 3-F-4-Me-Ph | H | DM |
| 729 | 3-F-4-Me-Ph | H | C2 |
| 730 | 3-F-4-Me-Ph | H | C3 |
| 731 | 3-F-4-Me-Ph | H | GN |

TABLE 69-continued

| No | A | $R^2$ | $R^3$ |
|---|---|---|---|
| 732 | 3-F-4-Me-Ph | Cl | RM |
| 733 | 3-F-4-Me-Ph | Cl | SM |
| 734 | 3-F-4-Me-Ph | Cl | DM |
| 735 | 3-F-4-Me-Ph | Cl | C2 |
| 736 | 3-F-4-Me-Ph | Cl | C3 |
| 737 | 3-F-4-Me-Ph | Cl | GN |
| 738 | 3-F-4-Me-Ph | Me | RM |
| 739 | 3-F-4-Me-Ph | Me | SM |
| 740 | 3-F-4-Me-Ph | Me | DM |
| 741 | 3-F-4-Me-Ph | Me | C2 |
| 742 | 3-F-4-Me-Ph | Me | C3 |
| 743 | 3-F-4-Me-Ph | Me | GN |
| 744 | 2,5-diF-Ph | H | RM |
| 745 | 2,5-diF-Ph | H | SM |
| 746 | 2,5-diF-Ph | H | DM |
| 747 | 2,5-diF-Ph | H | C2 |
| 748 | 2,5-diF-Ph | H | C3 |
| 749 | 2,5-diF-Ph | H | GN |
| 750 | 2,5-diF-Ph | Cl | RM |
| 751 | 2,5-diF-Ph | Cl | SM |
| 752 | 2,5-diF-Ph | Cl | DM |
| 753 | 2,5-diF-Ph | Cl | C2 |
| 754 | 2,5-diF-Ph | Cl | C3 |
| 755 | 2,5-diF-Ph | Cl | GN |
| 756 | 2,5-diF-Ph | Me | RM |
| 757 | 2,5-diF-Ph | Me | SM |
| 758 | 2,5-diF-Ph | Me | DM |
| 759 | 2,5-diF-Ph | Me | C2 |
| 760 | 2,5-diF-Ph | Me | C3 |
| 761 | 2,5-diF-Ph | Me | GN |
| 762 | 2,5-diF-Ph | H | RM |
| 763 | 3,5-diF-Ph | H | SM |
| 764 | 3,5-diF-Ph | H | DM |
| 765 | 3,5-diF-Ph | H | C2 |
| 766 | 3,5-diF-Ph | H | C3 |
| 767 | 3,5-diF-Ph | H | GN |
| 768 | 3,5-diF-Ph | Cl | RM |
| 769 | 3,5-diF-Ph | Cl | SM |
| 770 | 3,5-diF-Ph | Cl | DM |
| 771 | 3,5-diF-Ph | Cl | C2 |
| 772 | 3,5-diF-Ph | Cl | C3 |
| 773 | 3,5-diF-Ph | Cl | GN |
| 774 | 3,5-diF-Ph | Me | RM |
| 775 | 3,5-diF-Ph | Me | SM |
| 776 | 3,5-diF-Ph | Me | DM |
| 777 | 3,5-diF-Ph | Me | C2 |
| 778 | 3,5-diF-Ph | Me | C3 |
| 779 | 3,5-diF-Ph | Me | GN |
| 780 | 2,4,5-triF-Ph | H | RM |
| 781 | 2,4,5-triF-Ph | H | SM |
| 782 | 2,4,5-triF-Ph | H | DM |
| 783 | 2,4,5-triF-Ph | H | C2 |
| 784 | 2,4,5-triF-Ph | H | C3 |
| 785 | 2,4,5-triF-Ph | H | GN |
| 786 | 2,4,5-triF-Ph | Cl | RM |
| 787 | 2,4,5-triF-Ph | Cl | SM |
| 788 | 2,4,5-triF-Ph | Cl | DM |
| 789 | 2,4,5-triF-Ph | Cl | C2 |
| 790 | 2,4,5-triF-Ph | Cl | C3 |
| 791 | 2,4,5-triF-Ph | Cl | GN |
| 792 | 2,4,5-triF-Ph | Me | RM |
| 793 | 2,4,5-triF-Ph | Me | SM |
| 794 | 2,4,5-triF-Ph | Me | DM |
| 795 | 2,4,5-triF-Ph | Me | C2 |
| 796 | 2,4,5-triF-Ph | Me | C3 |
| 797 | 2,4,5-triF-Ph | Me | GN |
| 798 | 4-F-2Thi | H | RM |
| 799 | 4-F-2Thi | H | SM |
| 800 | 4-F-2Thi | H | DM |
| 801 | 4-F-2Thi | H | C2 |
| 802 | 4-F-2Thi | H | C3 |
| 803 | 4-F-2Thi | H | GN |
| 804 | 4-F-2Thi | Cl | RM |
| 805 | 4-F-2Thi | Cl | SM |
| 806 | 4-F-2Thi | Cl | DM |
| 807 | 4-F-2Thi | Cl | C2 |
| 808 | 4-F-2Thi | Cl | C3 |
| 809 | 4-F-2Thi | Cl | GN |
| 810 | 4-F-2Thi | Me | RM |
| 811 | 4-F-2Thi | Me | SM |
| 812 | 4-F-2Thi | Me | DM |
| 813 | 4-F-2Thi | Me | C2 |
| 814 | 4-F-2Thi | Me | C3 |
| 815 | 4-F-2Thi | Me | GN |
| 816 | 5-F-2Thi | H | RM |
| 817 | 5-F-2Thi | H | SM |
| 818 | 5-F-2Thi | H | DM |
| 819 | 5-F-2Thi | H | C2 |
| 820 | 5-F-2Thi | H | C3 |
| 821 | 5-F-2Thi | H | GN |
| 822 | 5-F-2Thi | Cl | RM |
| 823 | 5-F-2Thi | Cl | SM |
| 824 | 5-F-2Thi | Cl | DM |
| 825 | 5-F-2Thi | Cl | C2 |
| 826 | 5-F-2Thi | Cl | C3 |
| 827 | 5-F-2Thi | Cl | GN |
| 828 | 5-F-2Thi | Me | RM |
| 829 | 5-F-2Thi | Me | SM |
| 830 | 5-F-2Thi | Me | DM |

TABLE 70

| No | A | $R^2$ | $R^3$ |
|---|---|---|---|
| 831 | 5-F-2Thi | Me | C2 |
| 832 | 5-F-2Thi | Me | C3 |
| 833 | 5-F-2Thi | Me | GN |
| 834 | 5-Cl-2Thi | H | RM |
| 835 | 5-Cl-2Thi | H | SM |
| 836 | 5-Cl-2Thi | H | DM |
| 837 | 5-Cl-2Thi | H | C2 |
| 838 | 5-Cl-2Thi | H | C3 |
| 839 | 5-Cl-2Thi | H | GN |
| 840 | 5-Cl-2Thi | Cl | RM |
| 841 | 5-Cl-2Thi | Cl | SM |
| 842 | 5-Cl-2Thi | Cl | DM |
| 843 | 5-Cl-2Thi | Cl | C2 |
| 844 | 5-Cl-2Thi | Cl | C3 |
| 845 | 5-Cl-2Thi | Cl | GN |
| 846 | 5-Cl-2Thi | Me | RM |
| 847 | 5-Cl-2Thi | Me | SM |
| 848 | 5-Cl-2Thi | Me | DM |
| 849 | 5-Cl-2Thi | Me | C2 |
| 850 | 5-Cl-2Thi | Me | C3 |
| 851 | 5-Cl-2Thi | Me | GN |

INDUSTRIAL APPLICABILITY

The compounds of the present invention have a potent GnRH receptor antagonistic effect and additionally an excellent oral activity, and therefore are useful as pharmaceuticals for sex hormone-dependent diseases, especially GnRH-related diseases, for example, prostate cancer, benign prostatic hyperplasia, breast cancer, endometriosis, uterine fibroid, etc.

The invention claimed is:

1. A propane-1,3-dione derivative represented by the general formula (I) or a pharmaceutically acceptable salt thereof:

(I)

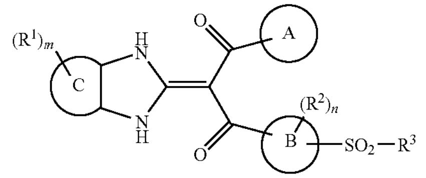

wherein the symbols in the formula have the following meanings:

ring A: optionally substituted aryl or optionally substituted heteroaryl, ring B: benzene ring or thiophene ring, ring C: benzene ring or 5- to 7-membered aliphatic hydrocarbon ring optionally having a double bond in the ring, $R^1$: the same or different, each representing halogen, optionally substituted hydrocarbon group, —O-(optionally substituted hydrocarbon group), optionally substituted heterocyclic group, —S-(optionally substituted hydrocarbon group), —CO-(optionally substituted hydrocarbon group), —$CO_2$-(optionally substituted hydrocarbon group), —O—CO-(optionally substituted hydrocarbon group), —SO-(optionally substituted hydrocarbon group), —$SO_2$— (optionally substituted hydrocarbon group), —$NO_2$, —CN, —$CO_2H$, optionally substituted carbamoyl, optionally substituted sulfamoyl, or optionally substituted amino group, $R^2$: the same or different, each representing halogen, $R^0$, —O—$R^0$ or halogen lower alkyl, m, n: the same or different, each indicating 0, 1 or 2, $R^3$: $R^0$, —OH, —O-optionally substituted heteroaryl, —$N(R^{51})(R^{52})$, —$N(R^{73})$-$N(R^{74})(R^{75})$,

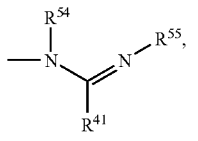 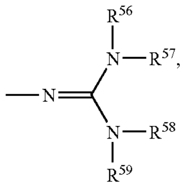

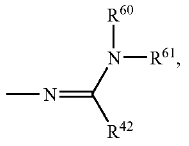 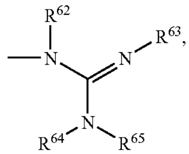

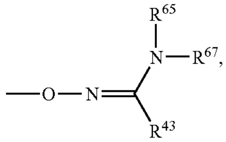 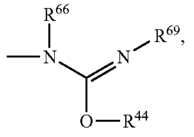

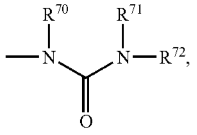 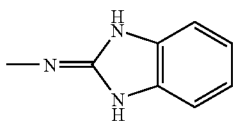,

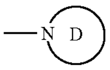, or, taken together with $R^2$, —N═C($R^{45}$)—NH— or —NH—C($R^{45}$)═N—, ring D: optionally substituted heterocyclic ring selected from the following group:

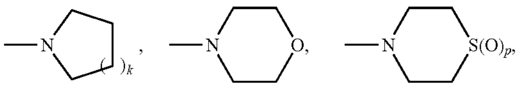

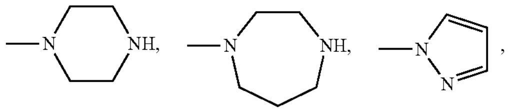

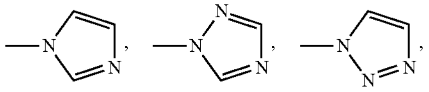

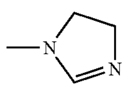 and 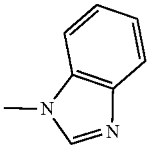, $R^0$: the same or different, each representing lower alkyl, $R^{00}$: the same or different, each representing lower alkylene, k: 1, 2, 3, or 4, p: 0, 1 or 2, $R^{41}$, $R^{42}$ and $R^{43}$: the same or different, each representing H, optionally substituted lower alkyl, —CHO, —CO-(optionally substituted lower alkyl), optionally substituted cycloalkyl, —$CO_2H$, —$CO_2$—$R^0$, —$CONH_2$, —CO—NH($R^0$—CO—N($R^0$)$_2$, —$R^{00}$—CONH($R^0$), —$R^{00}$—CON($R^0$)$_2$, optionally substituted aryl, optionally substituted heterocyclic group, —$R^{00}$—O-aryl, —$R^{00}$—SO—$R^0$—O—$R^{00}$—$SO_2$—$R^0$, —$R^{00}$—N(OH)—$R^0$ or —$R^{00}$—N(O—$R^0$)—$R^0$, $R^{44}$ and $R^{45}$: the same or different, each representing $R^0$ or —$R^{00}$-aryl, $R^{51}$ and $R^{52}$: the same or different, each representing H, optionally substituted lower alkyl, —$R^{00}$-(optionally substituted cycloalkyl), —$R^{00}$-(optionally substituted aryl), optionally substituted heteroaryl, —CO—$R^0$, —$CO_2$—$R^0$, —OH, —O—$R^0$, —O-benzyl, —$R^{00}$—O—$R^{00}$—OH or optionally substituted cycloalkyl, $R^{54}$, $R^{55}$, $R^{57}$, $R^{58}$, $R^{61}$, $R^{64}$, $R^{67}$, $R^{68}$, $R^{70}$, $R^{72}$, $R^{73}$ and $R^{74}$: the same or different, each representing H or $R^0$, $R^{56}$, $R^{59}$, $R^{66}$, $R^{69}$, and $R^{71}$: the same or different, each representing H, $R^0$ or —CO—$R^0$, $R^{60}$: H, $R^0$, —$R^{00}$—OH or —CO—$R^0$, $R^{62}$: H, $R^0$, —O—$R^0$ or —O-benzyl, $R^{63}$: H, $R^0$, —$NH_2$ or —CO—$R^0$, $R^{65}$: H, $R^0$, —$R^{00}$—OH—$CONH_2$ or —CO—$R^0$, $R^{75}$: H, $R^0$, —$R^{00}$-aryl, aryl or heteroaryl, or $R^{54}$ and $R^{41}$, $R^{57}$ and $R^{58}$, $R^{61}$ and $R^{42}$, $R^{68}$ and $R^{44}$, $R^{62}$ and $R^{63}$, $R^{62}$ and $R^{65}$, and $R^{63}$ and $R^{65}$, each taken together, may form lower alkylene optionally substituted with oxo group;

provided that, when ring A is phenyl substituted with —CH(OH)—$CH_2$—OH, and when m and n are both 0, then $R^3$ means a group except —$N(CH_3)_2$).

2. The compound according to claim 1, wherein the ring C is benzene ring, or a pharmaceutically acceptable salt thereof.

3. The compound according to claim 2, wherein the ring B is benzene ring, or a pharmaceutically acceptable salt thereof.

4. The compound according to claim 3, wherein ring A is optionally substituted phenyl, optionally substituted naphthyl, optionally substituted thienyl, optionally substituted pyridyl, optionally substituted thiazolyl, or benzofuranyl, or a pharmaceutically acceptable salt thereof.

5. The compound according to claim 4, wherein $R^3$ is —$N(R^{51})(R^{52})$ or a group selected from the following group, or a pharmaceutically acceptable salt thereof:

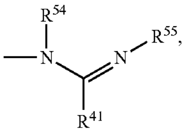

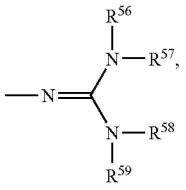

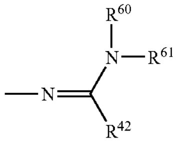

and

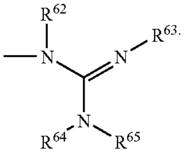

6. The compound according to claim 5, wherein m is 0 or a pharmaceutically acceptable salt thereof.

7. A propane-1,3-dione derivative of the general formula (Ia) or a pharmaceutically acceptable salt thereof:

(Ia)

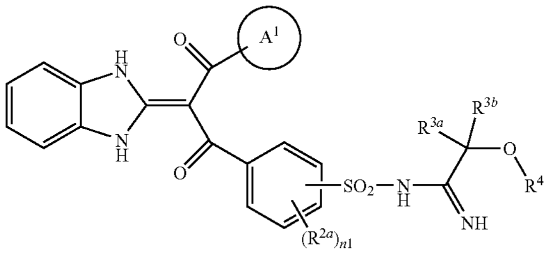

wherein the symbols in the formula have the following meanings:

ring $A^1$: phenyl or thienyl, each of which is optionally substituted with the same or different one to three substituents selected from the following group G:

Group G: halogen, lower alkyl and —O-lower alkyl, $R^{2a}$: halogen, lower alkyl or —O-lower alkyl, $R^{3a}$, $R^{3b}$: the same or different, each representing H or lower alkyl, $R^4$: H, —C(═O)-lower alkyl or —C(═O)-heteroaryl, n1: 0 or 1.

8. The compound according to claim 1, selected from the following group, or a pharmaceutically acceptable salt thereof:

(2R)-N-({3-[2-(1,3-dihydro-2H-benzimidazol-2-ylidene)-3-(3-fluorophenyl)-3-oxopropanoyl]phenyl}sulfonyl)-2-hydroxypropanimidamide, N-({3-[2-(1,3-dihydro-2H-benzimidazol-2-ylidene)-3-(3-fluorophenyl)-3-oxopropanoyl]phenyl}sulfonyl)-2-hydroxy-2-methylpropanimidamide, N-({5-[2-(1,3-dihydro-2H-benzimidazol-2-ylidene)-3-(3-fluorophenyl)-3-oxopropanoyl]-2-fluorophenyl}sulfonyl)-2-hydroxy-2-methylpropanimidamide, (2R)-N-({5-[2-(1,3-dihydro-2H-benzimidazol-2-ylidene)-3-(3-fluorophenyl)-3-oxopropanoyl]-2-fluorophenyl}sulfonyl)-2-hydroxypropanimidamide, (2R)-N-({5-[2-(1,3-dihydro-2H-benzimidazol-2-ylidene)-3-(3-methylphenyl)-3-oxopropanoyl]-2-fluorophenyl}sulfonyl)-2-hydroxypropanimidamide, N-({5-[3-(3,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide, (2R)-N-({5-[3-(3,5-difluorophenyl)-2-(1,3-dihydro-2H-benzimidazol-2-ylidene)-3-oxopropanoyl]-2-fluorophenyl}sulfonyl)-2-hydroxypropanimidamide, (2R)-N-({5-[3-(3-chlorophenyl)-2-(1,3-dihydro-2H-benzimidazol-2-ylidene)-3-oxopropanoyl]-2-fluorophenyl}sulfonyl)-2-hydroxypropanimidamide, N-({5-[2-(1,3-dihydro-2H-benzimidazol-2-ylidene)-3-oxo-3-(2,4,5-trifluorophenyl)propanoyl]-2-fluorophenyl}sulfonyl)-2-hydroxy-2-methylpropanimidamide, (2R)-N-({5-[1,3-dihydro-2H-benzimidazol-2-ylidene)-3-oxo-3-(2,4,5-trifluorophenyl)propanoyl]-2-fluorophenyl}sulfonyl)-2-hydroxypropanimidamide, (2R)-N-({5-[2-(1,3-dihydro-2H-benzimidazol-2-ylidene)-3-(3-fluoro-4-methylphenyl)-3-oxopropanoyl]-2-fluorophenyl}sulfonyl)-2-hydroxypropanimidamide, (2R)-N-({5-[3-(2,5-difluorophenyl)-2-(1,3-dihydro-2H-benzimidazol-2-ylidene)-3-oxopropanoyl]-2-fluorophenyl}sulfonyl)-2-hydroxypropanimidamide, N-({5-[3-(2,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide, (2R)-N-({5-[3-(5-chloro-2-thienyl)-2-(1,3-dihydro-2H-benzimidazol-2-ylidene)-3-oxopropanoyl]-2-fluorophenyl}sulfonyl)-2-hydroxypropanimidamide, and N-({5-[3-(5-chloro-2-thienyl)-2-(1,3-dihydro-2H-benzimidazol-2-ylidene)-3-oxopropanoyl]-2-fluorophenyl}sulfonyl)-2-hydroxy-2-methylpropanimidamide.

9. A pharmaceutical composition comprising the compound of claim 1 or a pharmaceutically acceptable salt thereof as an active ingredient.

10. A method for treating prostate cancer, benign prostatic hyperplasia, breast cancer, endometriosis and/or uterine fibroid, comprising administering a therapeutically effective amount of the compound of claim 1 or a pharmaceutically acceptable salt thereof to a patient in need thereof.

11. The compound according to claim 1, which is the following compound, or a pharmaceutically acceptable salt thereof:

(2R)-N-({3-[2-(1,3-dihydro-2H-benzimidazol-2-ylidene)-3-(3-fluorophenyl)-3-oxopropanoyl]phenyl}sulfonyl)-2-hydroxypropanimidamide.

12. The compound according to claim 1, which is the following compound, or a pharmaceutically acceptable salt thereof:

N-({3-[2-(1,3-dihydro-2H-benzimidazol-2-ylidene)-3-(3-fluorophenyl)-3-oxopropanoyl]phenyl}sulfonyl)-2-hydroxy-2-methylpropanimidamide.

13. The compound according to claim 1, which is the following compound, or a pharmaceutically acceptable salt thereof:

N-({5-[2-(1,3-dihydro-2H-benzimidazol-2-ylidene)-3-(3-fluorophenyl)-3-oxopropanoyl]-2-fluorophenyl}sulfonyl)-2-hydroxy-2-methylpropanimidamide.

14. The compound according to claim 1, which is the following compound, or a pharmaceutically acceptable salt thereof:

(2R)-N-({5-[2-(1,3-dihydro-2H-benzimidazol-2-ylidene)-3-(3-fluorophenyl)-3-oxopropanoyl]-2-fluorophenyl}sulfonyl)-2-hydroxypropanimidamide.

15. The compound according to claim 1, which is the following compound, or a pharmaceutically acceptable salt thereof:

N-({5-[3-(3,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide.

16. The compound according to claim 1, which is the following compound, or a pharmaceutically acceptable salt thereof:

(2R)-N-({5-[3-(3,5-difluorophenyl)-2-(1,3-dihydro-2H-benzimidazol-2-ylidene)-3-oxopropanoyl]-2-fluorophenyl}sulfonyl)-2-hydroxypropanimidamide.

17. The compound according to claim 1, which is the following compound, or a pharmaceutically acceptable salt thereof:

(2R)-N-({5-[3-(3-chlorophenyl)-2-(1,3-dihydro-2H-benzimidazol-2-ylidene)-3-oxopropanoyl]-2-fluorophenyl}sulfonyl)-2-hydroxypropanimidamide.

18. The compound according to claim 1, which is the following compound, or a pharmaceutically acceptable salt thereof:

(2R)-N-({5-[3-(2,5-difluorophenyl)-2-(1,3-dihydro-2H-benzimidazol-2-ylidene)-3-oxopropanoyl]-2-fluorophenyl}sulfonyl)-2-hydroxypropanimidamide.

19. The compound according to claim 1, which is the following compound, or a pharmaceutically acceptable salt thereof:

N-({5-[3-(2,5-difluorophenyl)-2-(1,3-dihydro-2H-benzimidazol-2-ylidene)-3-oxopropanoyl]-2-fluorophenyl}sulfonyl)-2-hydroxy-2-methylpropanimidamide.

* * * * *